(12) United States Patent
Kaminski et al.

(10) Patent No.: US 8,846,341 B2
(45) Date of Patent: Sep. 30, 2014

(54) MARKER PANELS FOR IDIOPATHIC PULMONARY FIBROSIS DIAGNOSIS AND EVALUATION

(75) Inventors: Naftali Kaminski, Pittsburgh, PA (US); Kevin F. Gibson, Gibsonia, PA (US); Bernadette R. Gochuico, Potomac, MD (US); Thomas J. Richards, Pittsburgh, PA (US); Ivan Rosas, Boston, MA (US); Kazuhisa Konishi, Kyoto (JP); Moises Selman, Mexico City (MX); Jose David Herazo-Maya, Pittsburgh, PA (US); Imre Noth, Chicago, IL (US)

(73) Assignees: University of Pittsburgh—of the Commonwealth System of Higher Education, Pittsburg, PA (US); The University of Chicago, Chicago, IL (US); Instituto Nacional de Enfermedades Respiratorias Ismael Cosio Villegas—D.F., Mexico City (MX)

(*) Notice: Subject to any disclaimer, the term of this patent is extended or adjusted under 35 U.S.C. 154(b) by 0 days.

(21) Appl. No.: 13/039,989

(22) Filed: Mar. 3, 2011

(65) Prior Publication Data

US 2012/0035067 A1 Feb. 9, 2012

Related U.S. Application Data

(63) Continuation of application No. PCT/US2009/056085, filed on Sep. 4, 2009.

(60) Provisional application No. 61/094,725, filed on Sep. 5, 2008.

(51) Int. Cl.
*C12P 21/06* (2006.01)
*A23J 1/00* (2006.01)
*C07K 1/00* (2006.01)
*C07K 14/00* (2006.01)
*C07K 16/00* (2006.01)
*C07K 17/00* (2006.01)
*C12P 19/34* (2006.01)
*C07H 21/04* (2006.01)

(52) U.S. Cl.
USPC ...... 435/69.1; 530/412; 435/91.2; 536/24.31; 536/24.33

(58) Field of Classification Search
None
See application file for complete search history.

(56) References Cited

U.S. PATENT DOCUMENTS

| | | | |
|---|---|---|---|
| 6,087,107 A * | 7/2000 | Sheffield et al. | 435/6.16 |
| 2002/0052308 A1 | 5/2002 | Rosen et al. | |
| 2004/0137538 A1* | 7/2004 | Bradford | 435/7.23 |
| 2005/0256072 A1 | 11/2005 | Aronin et al. | |
| 2007/0092488 A1* | 4/2007 | Strieter et al. | 424/85.6 |

(Continued)

OTHER PUBLICATIONS

Rasas et al., MMP1 and MMP7 as Potential Peripheral Blood Biomarkers in Idiopathic Pulmonary Fibrosis, PLoS Medicine, Apr. 2008, vol. 5, Issue 4, e93.*

(Continued)

*Primary Examiner* — Jim Ketter
*Assistant Examiner* — Reza Ghafoorian
(74) *Attorney, Agent, or Firm* — Baker Botts, L.L.P.

(57) ABSTRACT

The present invention relates to the discovery that of a panel of serum or plasma markers may be used to diagnose Idiopathic Pulmonary Fibrosis ("IPF") and distinguish this condition from other lung ailments. It further relates to the identification of markers associated with IPF disease progression.

16 Claims, 41 Drawing Sheets

(56) References Cited

U.S. PATENT DOCUMENTS

Figure 1A:
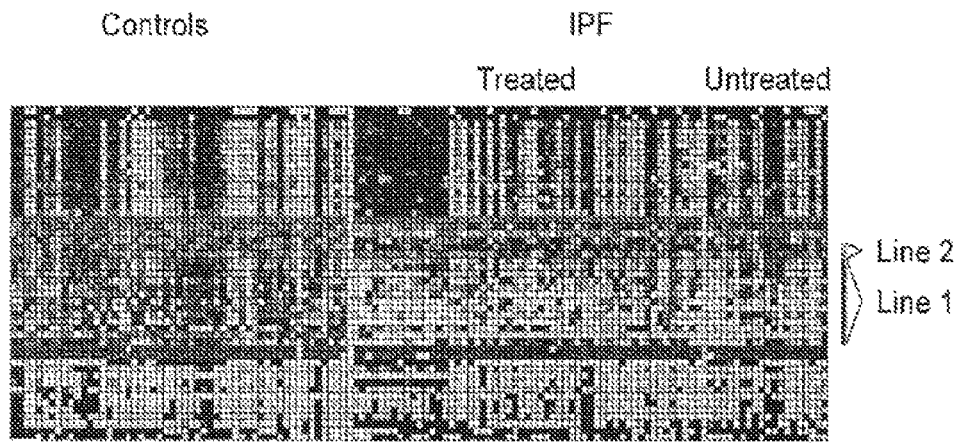

2007/0275925 A1 11/2007 Woodruff et al.
2008/0182245 A1 7/2008 Brown et al.
2012/0045395 A1 2/2012 Kaminski et al.

OTHER PUBLICATIONS

Mukae et al., Raised plasma concentrations of alpha-defensins in patients with idiopathic pulmonary fibrosis, Thorax 2002;57:623-628.*
Morbini et al., The receptor for advanced glycation end products and its ligands: a new inflammatory pathway in lung disease?, Modern Pathology (2006) 19, 1437-1445.*
Tsoutsou et al., Cytokine levels in the sera of patients with idiopathic pulmonary fibrosis, Respiratory Medicine (2006) 100, 938-945.*
Walter et al., Current Perspectives on the Treatment of Idiopathic Pulmonary Fibrosis, Proc Am Thorac Soc vol. 3. pp. 330-338, 2006.*
Mendoza et al., High-Throughput Microarray-Based Enzyme-Linked Immunosorbent Assay (ELISA), BioTechniques 27:778-788 (Oct. 1999).*
International Search Report for International Patent Application No. PCT/US2009/056085.
Rosas et al. MMP1 and MMP7 as Potential Peripheral Blood Biomarkers in Idiopathic Pulmonary Fibrosis. PLoS Medicine Apr. 2008, 5(4-e93):623-633.
Mackay et al. Pulmonary fibrosis: rate of disease progression as a trigger for referral for lung transplantation. Thorax Dec. 2007, 62(12):1069-1073.
International Search Report and Written Opinion for PCT/US2009/057897, dated Jun. 8, 2010.
Ebashir, et al., "Functional anatomy of siRNAs for mediating efficient RNAi in *Drosophila melanogaster* embryo lysate", *The EMBO Journal*, 20(23):6877-6888 (2001).
U.S. Appl. No. 13/052,854, filed Mar. 21, 2011.
U.S. Appl. No. 13/052,854, Jul. 20, 2012 Non-Final Office Action.
The American Thoracic Society and European Respiratory Society, "Idiopathic Pulmonary Fibrosis: Diagnosis and Treatment", *American Journal of Respiratory and Critical Care Medicine*, 161:646-664 (2000).
Acloque, et al., "Epithelial-mesenchymal transitions: the importance of changing cell state in development and disease", *J. Clin. Invest.*, 119(6):1438-1449 (2009).
Akira, et al., "CT findings during phase of accelerated deterioration in patients with idiopathic pulmonary fibrosis", *AJR American Journal of Roentgenology*, 168(1):79-83 (1997).
Andrews, et al., "A rapid micropreparation technique for extraction of DNA-binding proteins from limiting numbers pf mammalian cells", *Nucleic Acids Research*, 19(9):2499 (1991).
Ashitani, et al., High concentrations of α-defensins in plasma and bronchoalveolar lavage fluid of patients with acute respiratory distress syndrome, *Life Sciences*, 75(9):1123-1134 (2004).
Bartel, "MicroRNAs: Genomics, Biogenesis, Mechanism, and Function", *Cell*, 116:281-297 (2004).
Baskerville, et al., "Microarray Profiling of MicroRNAs Reveals Frequent Coexpression with Neighboring miRNAs and Host Genes", *RNA*, 11:241-247 (2005).
Boman, "Peptide antibiotics and their role in innate immunity",*Annu. Rev. Immunol.*, 13:61-92 (1995).
Brueckner, et al., "The Human *let-7a-3* Locus Contains an Epigenetically Regulated MicroRNA Gene with Oncogenic Function" *Cancer Research*, 67(4):1419-1423 (2007).
Burk, et al., "A reciprocal repression between ZEB1 and members of the miR-200 family promotes EMT and invasion in cancer cells", *EMBO Reports*, 9(6):582-589 (2008).
Bustos, et al., "Local and circulating microchimerism is associated with hypersensitivity pneumonitis", *American Journal of Respiratory and Critical Care Medicine*, 176:90-95 (2007).
Calin, et al., "Human microRNA genes are frequently located at fragile sites and genomic regions involved in cancers", *Proceedings of the National Academy of Sciences of the United States of America*, 101(9):2999-3004 (2004).

Chilosi, et al, "Aberrant Wnt/β-Catenin pathway activation ion idiopathic pulmonary fibrosis", *American Journal of Pathology*, 162(5):1495-1502 (2003).
Chilosi, et al., "Migratory marker expression in fibroblast foci of idiopathic pulmonary fibrosis", *Respiratory Research*, 7:95 (2006).
Chomczynski, et al., "Single-Step method of RNA isolation by acid guanidinium thicyanate-phenol-chloroform extraction", *Analytical Biochemistry*, 162:156-159 (1987).
Churg, et al., "Chronic hypersensitivity pneumonitis", *Am J. Surg. Pathol.*, 30(2):201-208 (2006).
Collard, et al., "Acute exacerbations of idiopathic pulmonary fibrosis", *American Journal of Respiratory and Critical Care Medicine*, 176(7):636-643 (2007).
Corcoran, et al., "Features of mammalian microRNA promoters emerge from polymerase II chromatin immunoprecipitation data", *PLoS ONE*, 4(4):e5279 (2009).
Corcoran, et al., "Footer: A quantitative comparative genomics method for efficient recognition of *cis*-regulatory elements", *Genome Research*, 15:840-847 (2005).
Cosgrove, et al., "Pigment epithelium-derived factor in idiopathic pulmonary fibrosis: A role in aberrant angiogenesis", *American Journal of Respiratory and Critical Care Medicine*, 170(3):242-251 (2004).
Cosgrove, et al., "Overexpression of matrix metalloproteinase-7 in pulmonary fibrosis", *Chest*, 121:25S-26S (2002).
Costabel, et al., "ATS/ERS/WASOG statement on sarcoidosis. Sarcoidosis Statement Committee. American Thoricic Society. European Respiratory Society. World Association for Sarcoidosis and other Granulomatous Disorders", *European Respiratory Journal*, 14:735-737 (1999).
Dave, et al., "Analysis of microarray experiments for pulmonary fibrosis", *Methods Mol. Med.*, 117:333-358 (2005).
Demedts, et al., "ATS/ERS international multidisciplinary consensus classification of the idiopathic interstitial pneumonias", *European Respiratory Journal*, 19(5):794-796 (2002).
Englert, et al., "A role for the receptor for advanced glycation end products in idiopathic pulmonary fibrosis", *The American Journal of Pathology*, 172(3):583-591 (2008).
Fukuda, et al., "Localization of matrix metalloproteinases-1, 2, and -9 and tissue inhibitor of metalloproteinase-2 in interstitial lung diseases", *Lab. Invest.*, 78:687-698 (1998).
Gadek, et al., "Collagenase in the lower respiratory tract of patients with idiopathic pulmonary fibrosis", *New England Journal of Medicine*, 301(14):737-742 (1979).
Gibson, et al., "The mechanisms of idiopathic pulmonary fibrosis: can we see the elephant?", *Drug Discovery Today: Disease Mechanisms*, 1:117-122 (2004).
Gomori, "A rapid one-step trichrome stain", *American Journal of Clinical Pathology*, 20(7):661-664 (1950).
Gong, et al., "Cyclin A2 regulates nuclear envelope breakdown and the nuclear accumulation of cyclin B1", *Curr. Biol.*, 17(1):85-91 (2007).
Gorelik, et al., "Multiplexed immunobead-based cytokine profiling for early detection of ovarian cancer", *Cancer Epidemiol Biomarkers Prev.*, 14:981-987 (2005).
Greene, et al., "Serum surfactant proteins-A and -D as biomarkers in idiopathic pulmonary fibrosis", *European Respiratory Journal*, 19:439-446 (2002).
Gregory, et al., "The miR-200 family and miR-205 regulate epithelial to mesenchymal transition by targeting ZEB1 and SIP1", *Nature Cell Biology*, 10:593-601 (2008).
Gross, et al., "Idiopathic pulmonary fibrosis", *The New England Journal of Medicine*, 345(7):517-525 (2001).
Henry, et al., "Matrix metalloproteinase and tissue inhibitor of metalloproteinase-1 in sarcoidosis and IPF", *European Respiratory Journal*, 20:1220-1227 (2002).
Hubbard, et al., "Lung Cancer and Cryptogenic Fibrosing Alveolitis", *American Journal of Respiratory and Critical Care Medicine*, 161:5-8 (2000).
Hunninghake, et al., Statement of sarcoidosis. Joint Statement of the American Thoracic Society (ATS), the European Respiratory Society (ERS) and the World Association of Sarcoidosis and Other Granulomatous Disorders (WASOG) adopted by the ATS Board of

(56) References Cited

OTHER PUBLICATIONS

Directors and by the ERS Executive Committee, *American Journal of Respiratory Critical Care Medicine*, 160:736-755 (1999).
Ihaka, et al., "R: A language for data analysis and graphics", *Journal of Computational and Graphical Statistics*, 5(3):299-314 (1996).
Iorio, et al., "MicroRNA Gene Expression Deregulation in Human Breast Cancer", *Cancer Research*, 65(16):7065-7070 (2005).
Iorio, et al., "MicroRNA Signatures in Human Ovarian Cancer", *Cancer Research*, 67(18):8699-8707 (2007).
Iwano, et al., "Evidence that Fibroblasts Derive from Epithelium During Tissue Fibrosis", *The Journal of Clinical Investigation*, 110:341-350 (2002).
Jain, et al., "Endothelin-1 Induces Alveolar Epithelial-Mesenchymal Transition through Endothelin Type A Receptor-Mediated Production of TGF-β1", *Am. J. Respir. Cell Mol. Biol.*, 37:38-47 (2007).
Johnson, et al., "*RAS* Is Regulated by the *let-7* MicroRNA Family", *Cell*, 120:635-647 (2005).
Johnson, et al., "The *let-7* MicroRNA Represses Cell Proliferation Pathways in Human Cells", *Cancer Research*, 67(16):7713-7722 (2007).
Kadota, et al, "High plasma concentrations of osteopontin in patients with interstitial pneumonia", *Respir. Med.*, 99:111-117 (2005).
Kalluri, et al., "The Basics of Epithelial-Mesenchymal Transition", *J. Clin. Invest.*, 119(6):1420-1428 (2009).
Kaminski, et al,, "Global analysis of gene expression in pulmonary fibrosis reveals distinct programs regulating lung inflammation and fibrosis", *PNAS*, 97(4):1778-1783 (2000).
Kaminski, et al., "Gene expression profiling as a window into idiopathic pulmonary fibrosis pathogenesis: can we identify the right target genes?" *Proc. Am. Thorac. Soc.*, 3(4):339-344 (2006).
Katzenstein, et al., "Idiopathic pulmonary fibrosis: clinical relevance of pathologic classification", *American Journal of Respiratory and Critical Care Medicine*, 157:1301-1315 (1998).
Katzenstein, et al., American Thoracic Society/European Respiratory Society International Multidisciplinary Consensus Classification of the Idiopathic Interstitial Pneumonias. This joint statement of the American Thoracic Society (ATS), and the European Respiratory Society (ERS) was adopted by the ATS board of directors, Jun. 2001 and by the ERS Executive Committee, Jun. 2011., *American Journal of Respiratory and Critical Care Medicine*, 165:277-304 (2001).
Keane, et al., "Mechanisms and mediators of pulmonary fibrosis", *Crit. Rev. Immunol.*, 25(6):429-463 (2005).
Kent, et al., "The human genome browser at UCSC", *Genome Research*, 12:996-1006 (2002).
Kim, et al., "Alveolar epithelial cell mesenchyma; transition develops in vivo during pulmonary fibrosis and is regulated by the extracellular matrix", *Proceedings of the National Academy of Sciences of the United States of America*, 103(35):13180-13185 (2006).
King, et al., "Predicting survival in idiopathic pulmonary fibrosis: scoring system and survival model", *American Journal of Respiratory and Critical Care Medicine*, 164(7):1171-1181 (2001).
Königshoff, et al., "Functional Wnt signaling is increased in idiopathic pulmonary fibrosis", *PloS ONE*, 3(5):e2142 (2008).
Königshoff, et al., "WNT 1-Inducible Signaling Protein-1 Mediates Pulmonary Fibrosis in Mice and is Upregulated in Humans with Idiopathic Pulmonary Fibrosis", *J. Clin. Invest*; 119(4):772-787 (2009).
Konishi, et al., "Gene Expression Profiles of Acute Exacerbations of Idiopathic Pulmonary Fibrosis", *American Journal of Respiratory and Critical Care Medicine*, 180:167-175 (2009).
Korpal, et al., "The miR-200 family inhibits epithelial-mesenchymal transition and cancer cell migration by direct targeting of E-cadherin transcriptional repressors ZEB1 and ZEB2", *The Journal of Biological Chemistry*, 283(22):14910-14914 (2008).
Krek, et al., "Combinatorial microRNA target predictions", *Nature Genetics*, 37:495-500 (2005).
Krutzfeldt, et al., "Silencing of microRNAs in vivo with antagomirs", *Nature*, 438:685-689 (2005).

Kuwano, et al., "Increased circulating levels of soluble Fas ligand are correlated with disease activity in patients with fibrosing lung diseases", *Respirology*, 7:15-21 (2002).
Lau, et al., "An abundant class of tiny RNAs with probable regulatory roles in *Caenorhabditis elegans*", *Science*, 294:858-862 (2001).
Lee, et al., "Transcriptional Regulatory Networks in *Saccharomyces cerevisiae*", *Science*, 298:799-804 (2002).
Lee, et al., "MicroRNA genes are transcribed by RNA polymerase II", *The EMBO Journal*, 23:4051-4060 (2004).
Li, et al., "Matrilysin shedding of syndecan-1 regulates chemokine mobilization and transepithelial efflux of neutrophils in acute lung injury", *Cell*, 111:635-646 (2002).
Lindell, et al., "Lessons from our patients: Development of a warm autopsy program", *PLoS Medicine*, 3(7):e234 (2006).
Mahony, et al., "Regulatory conservation of protein coding and microRNA genes in vertebrates: lessons from the opossum genome", *Genome Biology*, 8(5):R84.1-R84.18 (2007).
Mandal, et al., "Epithelial to mesenchymal transition in head and neck squamous carcinoma", *Cancer*, 112:2088-2100 (2008).
Marson, et al., "Connecting microRNA Genes to the Core Transcriptional Regulatory Circuitry of Embryonic Stem Cells", *Cell*, 134:521-533 (2008).
Mayr, et al., "Disrupting the pairing between *let-7* and Hmga2 enhances oncogenic transformation", *Science*, 315:1576-1579 (2007).
McGuire, et al., "Matrilysin (Matrix Metalloproteinase-7) mediates E-cadherin ectodomain shedding in injured lung epithelium", *The American Journal of Pathology*, 162(6):1831-1843 (2003).
McMillan, et al., "Exacerbation of established pulmonary fibrosis in a murine model by gammaherpesvirus", *American Journal of Respiratory and Critical Care Medicine*, 177(7):771-780 (2008).
Moeller, et al., "Circulating fibrocytes are an indicator of poor prognosis in idiopathic pulmonary fibrosis", *American Journal of Respiratory and Critical Care Medicine*, 179:588-594 (2009).
Mott, et al., "Mir-29 regulates Mc1-1 protein expression and apoptosis", *Oncogene*, 26(4):6133-6140 (2007).
Mukae, et al, "Elevated BALF concentrations of α- and β-defensins in patients with pulmonary alveolar proteinosis", *Respiratory Medicine*, 101:715-721 (2007).
Murakami, et al., "Comprehensive analysis of microRNA expression patterns in hepatocellular carcinoma and non-tumorous tissues", *Oncogene*, 25:2537-2545 (2006).
Nana-Sinkam, et al., "Integrating the MicroRNome into the Study of Lung Disease", *American Journal of Respiratory and Critical Care Medicine*, 179:4-10 (2009).
Narita, et al., "A Novel Role for High-Mobility Group A Proteins in Cellular Senescence and Heterochromatin Formation", *Cell*, 126:503-514 (2006).
Nawshad, et al., "Transforming growth factor-β signaling during epithelial-mesenchymal transformation: implications for embryogenesis and tumor metastasis", *Cells Tissues Organs*, 179(1-2):11-23 (2005).
Nelsestuen, et al., "Proteomic identification of human neutrophil alpha-defensins in chronic lung allograft rejection", *Proteomics*, 5:1705-1713 (2005).
Novershtern, et al., "A functional and regulatory map of asthma", *American Journal of Respiratory Cell and Molecular Biology*, 38(3):324-336 (2008).
Ohtani, et al., "Chronic bird fancier's lung: Histopathological and clinical correlation. An application of the 2002 ATS/ERS consensus classification of the idiopathic interstitial pneumonias", *Thorax*, 60(8):665-671 (2005).
Olson, et al., "Mortality from Pulmonary Fibrosis Increased in the United States from 1992 to 2003", *American Journal of Respiratory and Critical Care Medicine*, 176:277-284 (2007).
Pardo, et al.,"Up-Regulation and profibrotic role of osteopontin in human idiopathic pulmonary fibrosis", *PloS Medicine*, 2(9):e251 (2005).
Pardo, et al., "Matrix metalloproteases in aberrant fibrotic tissue remodeling", *Proc. Am. Thorac Soc.*, 3:383-388 (2006).
Pardo, et al., "Approaching the degradome in idiopathic pulmonary fibrosis", *The International Journal of Biochemistry & Cell Biology.*, 40(6-7):1141-1155 (2008).

(56) References Cited

OTHER PUBLICATIONS

Pasquinelli, et al., "Conservation of the sequence and temporal expression of *let-7* heterochronic regulatory RNA", *Nature*, 408:86-89 (2000).
Park, et al., "The miR-200 family determines the epithelial phenotype of cancer cells by targeting the E-cadherin repressors ZEB1 and ZEB2", *Genes & Development*, 22:894-907 (2008).
Pauwels, et al., "Global strategy for the diagnosis, management, and prevention of chronic obstructive pulmonary disease. NHLBI/WHO Global Initiative for Chronic Obstructive Lung Disease (GOLD) Workshop Summary", *American Journal of Respiratory and Critical Care medicine*, 163:1256-1276 (2001).
Perez-Padilla, et al., "Mortality in Mexican patients with chronic pigeon breeder's lung compared with those with usual interstitial pneumonia", *Am. Rev. Respir. Dis.*, 148(1):49-53 (1993).
Plataki, et al., "Expression of Apoptotic and Antiapoptotic Markers in Epithelial Cells in Idiopathic Pulmonary Fibrosis", *Chest*, 127:266-274 (2005).
Prohaszka, et al., "Defensins purified from human granulocytes bind $C1_q$ and activate the classical complement pathway like the transmembrane glycoprotein $_{gp}41$ of HIV-1" *Molecular Immunology*, 34:809-816 (1997).
Reinhart, et al., "The 21-nucleotide *let-7* RNA regulates development timing in *Caenorhanditis elegans*", *Nature*, 403:901-906 (2000).
Ren, et al., "Impairment of alveolar macrophage transcription in idiopathic pulmonary fibrosis", *American Journal of Respiratory and Critical Care Medicine*, 175(11):1151-1157 (2007).
Rosas, et al., "When it comes to genes—IPF or NSIP, familial or sporadic—They're all the same", *American Journal of Respiratory and Critical Care Medicine*, 175(1):5-6 (2007).
Rosas, et al., "Early interstitial lung disease in familial pulmonary fibrosis", *American Journal of respiratory and Critical Care Medicine*, 176(7):698-705 (2007).
Sakamoto, et al., "Differential effects of α- and β-defensin on cytokine production by cultured human bronchial epithelial cells", *American Journal of Physiology Lung Cellular and Molecular Physiology*, 288(3):L508-L513 (2005).
Saydain, et al., "Outcome of patients with idiopathic pulmonary fibrosis admitted to the intensive care unit", *American Journal of Respiratory Critical Care Medicine*, 166:839-842 (2002).
Segal, et al., "From signatures to models: understanding cancer using microarrays", *Nature Genetics*, 36(10):S38-S45 (2005).
Segal, et al., "A module map showing conditional activity of expression modules in cancer", *Nature Genetics*, 36(10):1090-1098 (2004).
Selman, et al., "Idiopathic Pulmonary Fibrosis: Prevailing and evolving hypotheses about its pathogenesis and implications for therapy", *Annals of Internal Medicine*, 134:136-151 (2001).
Selman, et al., "Role of epithelial cells in idiopathic pulmonary fibrosis from innocent targets to serial killers", *Proceedings of the American Thoracic Society*, 3:364-372 (2006).
Selman, et al., "Idiopathic pulmonary fibrosis: Aberrant recapitulation of developmental programs?", *PloS Medicine*, 5(3):e62 (2008).
Selman, et al., "TIMP-1, -2, -3, and -4 in idiopathic pulmonary fibrosis. A prevailing nondegradative lung microenviroment?", *American Journal of Physiology*, 279:L562-574 (2000).
Selman, et al., "Idiopathic Pulmonary Fibrosis: Diagnosis and Treatment", *American Journal of Respiratory and Critical Care Medicine*, 161:646-664 (2000).
Selman, et al., "Accelerated variant of idiopathic pulmonary fibrosis: clinical behavior and gene expression patterns", *PloS One*, 2(5):e482 (2007).
Selman, et al., "Gene expression profiles distinguish idiopathic pulmonary fibrosis from hypersensitivity pneumonitis", *American Journal of Respiratory and Critical Care medicine*, 173(2):188-198 (2006).
Shell, et al., "Let-7 expression defines two differentiation stages of cancer", *Proceedings of the National Academy of Sciences of the United States of America*, 104:11400-11405 (2007).
Spencer, et al., "Role of human neutrophil peptides in lung inflammation associated with alpha1-antitrypsin deficiency", *American Journal of Physiology*, 286(3):L514-L520 (2004).
Steele, et al., "Clinical and pathologic features of familial interstitial pneumonia", *American Journal of Respiratory and Critical Care medicine*, 172(9):1146-1152 (2005).
Suga, et al., "Clinical significance of MCP-1 levels in BALF and serum in patients with interstitial lung diseases", *European Respiratory Journal*, 14:376-382 (1999).
Suga, et al., "Characteristic elevation of matrix metalloproteinase activity in idiopathic interstitial pneumonias", *American Journal of Respiratory and Critical Care Medicine*, 162:1949-1956 (2000).
Tajima, et al., "The increase in serum soluble ST2 protein upon acute exacerbation of idiopathic pulmonary fibrosis", *Chest*, 124:1206-1214 (2003).
Thomson, et al., "Extensive post-transcriptional regulation of microRNAs and its implications for cancer", *Genes & Development*, 20:2202-2207 (2006).
Thuault, et al., "Transforming growth factor-β employs HMGA2 to elicit epithelial-mesenchymal transition", *The Journal of cell Biology*, 174:175-183 (2006).
Thum, et al., "MicroRNAs in the human heart: A clue to fetal gene reprogramming in heart failure", *Circulation*, 116:258-267 (2007).
Tomioka, et al., "Acute exacerbation of idiopathic pulmonary fibrosis: role of *Chlamydophila pneumoniae* infection", *Respirology*, 12:700-706 (2007).
Turley, et al., "Mechanisms of Disease: epithelial-mesenchymal transition—does cellular plasticity fuel neoplastic progression?", *Nat. Clin. Pract. Oncol.*, 5(5):280-290 (2008).
Tusher, et al., "Significance analysis of microarrays applied to the ionizing radiation response", *PNAS*, 98(9):5116-5121 (2001).
Tzouvelekis, et al., "Comparative Expression Profiling in Pulmonary Fibrosis Suggests a Role of Hypoxia-Inducible Factor-1α in Disease Pathogenesis", *Am. J. Respir. Crit. Care Med.*, 176:1108-1119 (2007).
Uchida, et al., "Receptor for advanced glycation end-products is a marker of type I cell injury in acute lung injury", *American Journal of Respiratory and Critical Care medicine*, 173(9):1008-1015 (2006).
van den Berg, et al., "Inhibition of activation of the classical pathway of complement by human neutrophil defensisn", *Blood*, 92:3898-3903 (1998).
Vuga, et al., "WNT5A Is a Regulator of Fibroblast Proliferation and Resistance to Apoptosis", *Am J. Respir. Cel Mol. Biol.*, 41:583-589 (2009).
Vuorinen, et al., "Elevated matrilysin levels in bronchoalveolar lavage fluid do not distinguish idiopathic pulmonary fibrosis from other interstitial lung diseases", *APMIS*, 115(8):969-75 (2007).
Wang, et al., "Caveolin-1: A critical regulator of lung fibrosis in idiopathic pulmonary fibrosis", *J. Exp. Med.*, 203(13):2895-2906 (2006).
Willis, et al., "Induction of epithelial-mesenchymal transition in alveolar epithelial cells by transforming growth factor-β1", *The American Journal of Pathology*, 166:1321-1332 (2005).
Willis, et al., "TGF-β-induced EMT: mechanisms and implications for fibrotic lung disease", *American Journal of Physiology*, 293:L525-534 (2007).
Wu, et al., "MicroRNAs in the Pathogenesis of Lung Cancer", *Journal of. Thoracic Oncology*, 4(8):1028-1037 (2009).
Wu, et al., "Comparison of normalization methods for CodeLink Bioarray data", *BMC Bioinformatics*, 6:309 (2005).
Yang, et al., "Epithelial-Mesenchymal Transition: At the Crossroads of Development and Tumor Metastasis", *Development Cell*, 14:818-829 (2008).
Yang, et al., "Gene expression profiling of familial and sporadic interstitial pneumonia", *American Journal of Respiratory and Critical Care Medicine*, 175(1):45-54 (2007).
Yokoyama, et al., "Circulating KL-6 predicts the outcome of rapidly progressive idiopathic pulmonary fibrosis", *American Journal of Respiratory and Critical Care Medicine*, 158(5 Pt. 1):1680-1684 (1998).

(56) References Cited

OTHER PUBLICATIONS

Yoshioka, et al., "Alpha-defensin enhances expression of HSP47 and collagen-1 in human lung fibroblasts", *Life Science*, 80(20):1839-1845 (2007).

Zahurak, et al., "Pre-processing Agilent microarray data", *BMC Bioinformatics*, 8:142 (2007).

Zasloff, "Antimicrobial peptides of multicellular organisms", *Nature*, 415:389-395 (2002).

Zavadil, et al., "Genetic programs of epithelial cell plasticity directed by transforming growth factor-β", *Proceedings of the National Academy of Sciences of the United States of America*, 98(12):6686-6691 (2001).

Zeisberg, et al., "The role of epithelial-to-mesenchymal transition in renal fibrosis", *Journal of Molecular Medicine*, 85:175-181 (2004).

Zhang, et al., "An extensible application for assembling annotation for genomic data", *Bioinformatics Applications Note*, 19(1):155-156 (2003).

Zhou, et al., "Mutation responsible for the mouse pygmy phenotype in the decelopmentally regulated factor HMGI-C", *Nature*, 376:771-774 (1995).

Ziegenhagen, et al., "Serum level of interleukin 8 is elevated in idiopathic pulmonary fibrosis and indicates disease activity", *American Journal of Respiratory and Critical Care Medicine*, 157(3):762-768 (1998).

Zuo, et al., "Gene expression analysis reveals matrilysin as a key regulator of pulmonary fibrosis in mice and humans", *PNAS*, 99(9):6292-6297 (2002).

\* cited by examiner

| Cluster 1: 496 genes | | |
|---|---|---|
| Number of genes in category | P-value | GO names |
| 29 | 1.9e-10 | iron ion binding |
| 51 | 1.7e-08 | oxidoreductase activity |
| 21 | 9.8e-07 | response to wounding |
| 33 | 1.1e-06 | endoplasmic reticulum |
| 83 | 1.3e-06 | developmental process |
| 24 | 8.3e-06 | response to external stimulus |
| 66 | 9.4e-06 | plasma membrane |
| 60 | 1e-05 | multicellular organismal developpment |
| 34 | 1.1e-05 | positive regulation of biological process |
| 76 | 4.4e-05 | response to stimulus |
| 57 | 4.7e-05 | plasma membrane part |
| 22 | 4.8e-05 | defense response |

| Cluster 3: 363 genes | | |
|---|---|---|
| Number of genes in category | P-value | GO names |
| 62 | 2.8e-14 | anatomical structure developpment |
| 67 | 5.9e-14 | multicellular organismal development |
| 83 | 2.4e-13 | developmental process |
| 47 | 1.2e-11 | calcium ion binding |
| 36 | 1.3e-10 | cell adhesion |
| 35 | 2.8e-09 | anatomical structure morphogensis |
| 40 | 1.1e-08 | intrinsic to plasma membrane |
| 35 | 3.3e-08 | organ development |
| 42 | 2.1e-06 | cell differentiation |
| 33 | 1.3e-05 | ion transmembrane transporter activity |
| 35 | 2.2e-05 | transcription factor activity |
| 35 | 3.2e-05 | substrate-specific transmembrane transporter activity |

FIG.10

US 8,846,341 B2

MARKER PANELS FOR IDIOPATHIC PULMONARY FIBROSIS DIAGNOSIS AND EVALUATION

CROSS REFERENCE TO RELATED APPLICATIONS

This application is a continuation of International Application No. PCT/US2009/056085, filed Sep. 4, 2009, which claims priority to U.S. Provisional Application Ser. No. 61/094,725, filed Sep. 5, 2008, both of which are hereby incorporated by reference in their entireties, and from which priority is claimed.

The subject matter disclosed herein was developed at least in part under grants HL073745, HL0793941, HL0894932, and HL095397 from the National Institutes of Health, so that the United States Government has certain rights herein.

1. INTRODUCTION

The present invention relates to the discovery that of a panel of serum or plasma markers may be used to diagnose Idiopathic Pulmonary Fibrosis ("IPF") and distinguish this condition from other lung ailments. It further relates to the identification of markers associated with IPF disease progression.

2. BACKGROUND OF THE INVENTION

Idiopathic pulmonary fibrosis (IPF), a progressive fibrotic interstitial lung disease (ILD) with median survival of 2.5-3 years, is largely unaffected by currently available medical therapies (Kim D S et al., 2006). The disease is characterized by alveolar epithelial cell injury and activation, fibroblast/myofibroblast foci formation, and exaggerated accumulation of extracellular matrix in the lung parenchyma. Recent studies employing high-throughput genomic technologies to analyze samples from IPF patients or genetically modified animals have highlighted the complexity of the pathways involved in the disease (Kaminski N and Rosas I O, 2006; Gibson K F and Kaminski N, 2004; Keane M P et al., 2005). While these studies have improved the understanding of the molecular mechanisms underlying lung fibrosis, they did not translate well into the clinical arena.

Identification of peripheral blood biomarkers may facilitate the diagnosis and follow-up of patients with IPF as well as the implementation of new therapeutic interventions. Currently, establishing a diagnosis of IPF may require surgical lung biopsy in patients with atypical clinical presentations or high-resolution computed tomography (HRCT) scans. Patients with IPF are often evaluated by serial pulmonary physiology measurements and repeated radiographic examinations. These studies provide a general assessment of the extent of disease, but do not provide information about disease activity on a molecular level. Higher plasma concentrations of surfactant proteins (Greene K E et al., 2002), KL-6 (Yokoyama A et al., 1998), FASL (Kuwano K et al., 2002), CCL-2 Suga M et al., 1999), α-defensins (Mukae H et al., 2002), and most recently SPP1 (Kadota J et al., 2005) have been reported in patients with IPF and other ILDs but most of these studies were modest in size and assayed only a single or a few protein markers simultaneously. Matirx metalloproteinase-8 ("MMP8") has been implicated as playing a role in tissue remodeling in IPF, but also in sarcoidosis (Henry, M T et al., (2002), making it a non-specific marker of IPF. Similarly, matrix metalloproteinase-7 ("MMP7") was reported to be elevated in bronchoalveolar fluid from both IPF patients as well as patients suffering from cryptogenic organizing pneumonia ("COP"; Huh, J W et al., 2008).

3. SUMMARY OF THE INVENTION

The present invention relates to panels of markers and their use in diagnosing and evaluating the severity and/or progression of IPF. It is based, at least in part, on the discovery that identifying increases in the plasma levels of MMP7, MMP1 and MMP8, as well as IGFBP1 and/or TNFRSF1A, indicates a diagnosis of IPF with a high degree of sensitivity and specificity. Identifying a decrease in the plasma level of AGER further confirms the IPF diagnosis. Further markers which indicate a diagnosis of IPF include an increase in plasma levels of SFTPD, MEG3 and/or ID-1 and/or a decrease in serum levels of IL-4, ICOS, and/or CCR7. Accordingly, in various embodiments, the present invention provides for methods of diagnosis as well as diagnostic kits.

The invention is further based, in part, on the discovery that certain markers are associated with and predictive of progression of IPF. Such markers include, but are not limited to, increases in plasma levels of MMP7, DEFA-1, DEFA-2, DEFA-3, S100A12, CCNA2, and IL12P40. In various embodiments, the present invention provides for methods of evaluating the progression of disease as well as kits for this purpose.

4. BRIEF DESCRIPTION OF THE DRAWINGS

Figure 1B:
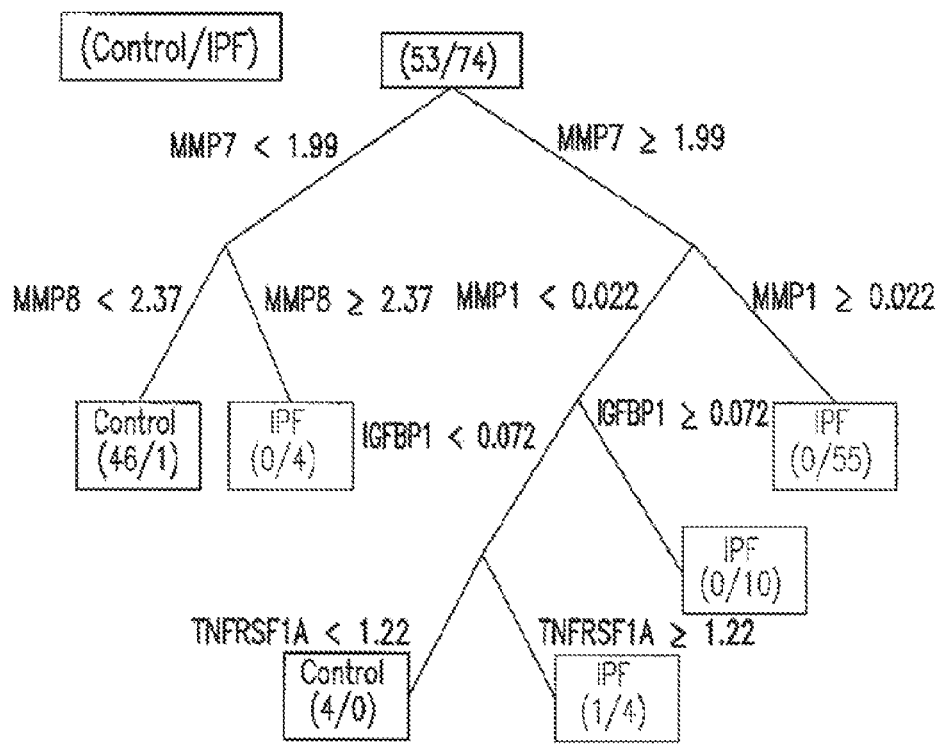
Figure 1C:
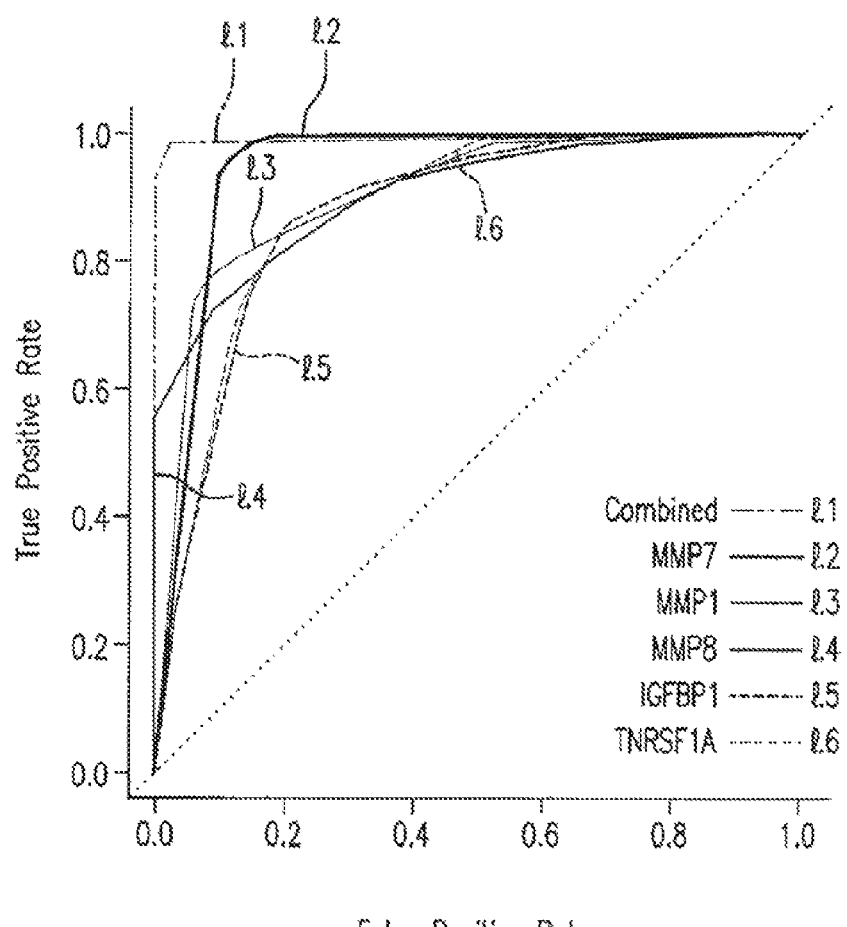

FIG. 1A-C. (A) Heatmap of proteins measured in the plasma of IPF and control patients. Individual patients are represented in columns, and proteins are represented in rows. Every protein level was divided by the geometric mean of values for the same proteins for all patients and log based 2 transformed. Increasing shades of yellow—increased. Increased shades of purple—decreased. Gray—unchanged. Proteins were clustered using Genomica. Vertical Line 1 indicates the cluster of proteins increased in IPF. Vertical Line 2 indicates the cluster of proteins decreased in IPF. (B) Classification tree obtained by CART applied to plasma protein concentration data from IPF patients and controls. Boxes identify a terminal node as Control or IPF. All counts are listed as Control/IPF. Concentrations are in ng/ml. In the subgroup with high MMP7 concentration but low MMP1 concentration (14 IPF samples, 5 control samples), splitting on IGFBP1 and TNFRSF1A improves classification, while in the subgroup with low MMP7, MMP8 improves classification. (C) ROC curves for using each of five markers, or their combination, to classify samples as IPF or control. Sensitivity, or true positive rate, is plotted on the y-axis and false positive rate, or 1 minus specificity, on the x-axis. The area under each ROC curve is equivalent to the numerator of the Mann-Whitney U statistic comparing the marker distributions between IPF and control samples. The magenta line labeled "Combined" is for the combinatorial classifier using all five markers. The identity line at 45 degrees represents a marker that performed no better than classifying samples as IPF or Control by flipping a fair coin.

Figure 2A:
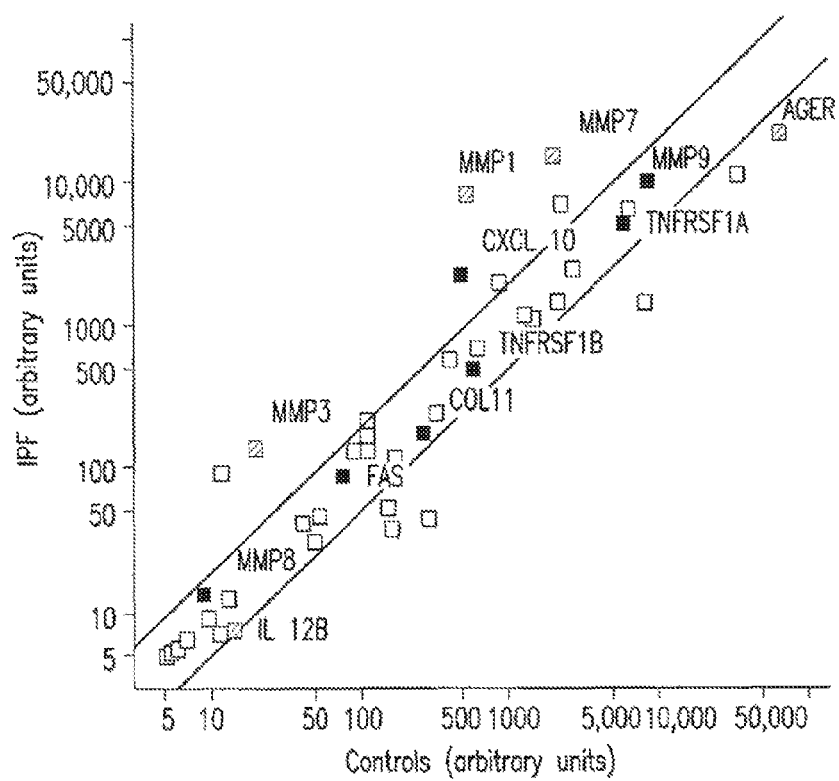
Figure 2B:
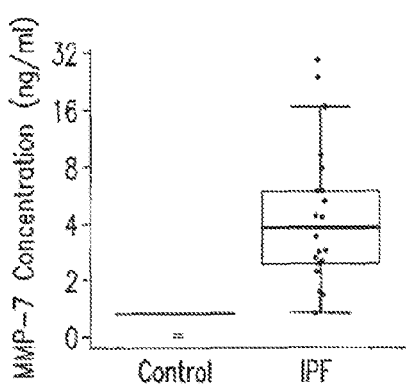
Figure 2C:
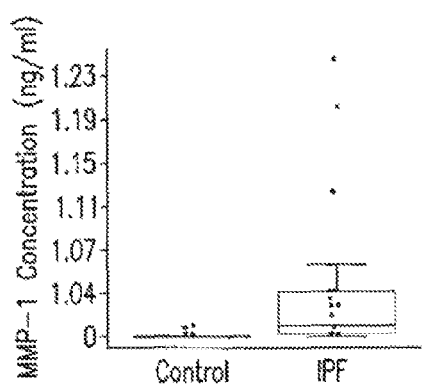

FIG. 2A-C. MMP7 and MMP1 gene and protein levels were significantly increased in the lungs of patients with IPF. (A) Average gene expression levels (log scale) measured using gene expression microarrays of genes that encode the 49 protein markers in IPF lungs (y axis) compared to control lungs (x axis). Colored squares (black or dark grey) are genes that encode proteins that changed significantly in plasma. Genes marked by an asterisk (*) are genes that changed significantly (SAM Q value<5%) in gene expression data and that encode proteins measured in peripheral blood. Oblique lines denote 2-fold change. MMP7 (B) and MMP1 (C) concentrations (ng/ml) were significantly (p<0.00001 and p=0.018 respectively) higher in BAL fluid of patients with IPF (n=22) compared to control subjects (n=10).

FIG. 3. MMP7 and MMP1 plasma concentrations were high in IPF, but not sarcoidosis or COPD. Concentrations (ng/ml) of MMP7 (A) and MMP1 (B) were significantly higher in patients with IPF (n=74; p<0.00001 and p=0.018 respectively), compared to controls (n=53), but not sarcoidosis (n=47; p=0.78 and p=0.28, respectively) compared to controls (n=53) or COPD (n=73; p=0.21 and 0.85, respectively, stratified by GOLD class, as 0-I, II, and III-IV).

FIG. 4A-E. MMP7 and MMP1 plasma concentrations were higher in IPF, compared to HP. Concentrations (ng/ml) of MMP7 (A) and MMP1 (B) in the blood were significantly higher in patients with IPF (n=34), than in patients with HP (n=41). (C) Average gene expression levels (log scale) in IPF samples (y axis) compared to HP (x axis) measured by gene expression microarrays. Gray circles—all genes on the array. Circles with asterisk (*) indicate MMP1 and MMP7. Oblique lines denote 2 fold change. (D) Combinations of plasma MMP7 (y axis) and MMP1 concentrations (x axis) in IPF (closed circles) and HP patients (open circles). Corners represent points in which the trade-off between positive predictive value (PPV) and negative predictive value (NPV) are optimal for ruling out IPF (i) or concluding IPF (ii) based on MMP1 and MMP7 concentrations. (E) ROC curves for using MMP1, or MMP7, or their combination, to classify samples as IPF or HP. Sensitivity, or true positive rate, is plotted on the y-axis and false positive rate, or 1 minus the specificity, on the x-axis. The identity line at 45 degrees represents a marker that performed no better than classifying samples as IPF or HP by flipping a fair coin.

FIG. 5A-D. MMP7 concentrations significantly distinguished control from sub-clinical ILD, familial or sporadic IPF (A). Dark solid lines show median concentrations in each group. The interquartile range (IR), or middle 50%, of concentrations is delimited by a box. Data are expressed on a log base 2 scale. (B) ROC curves for using MMP1 or MMP7, or their combination, to classify samples as IPF (sporadic or familial) or control in validation cohort. Plasma MMP concentrations moderately correlated with decreases in FVC % predicted (C) and DLCO % predicted (D). Linear regressions and 95% confidence inversely related MMP7 concentration (ng/ml) to FVC %, and DLCO %. * represents p<0.05;  represents p<0.01; and * represents p<0.001.

Figure 6:
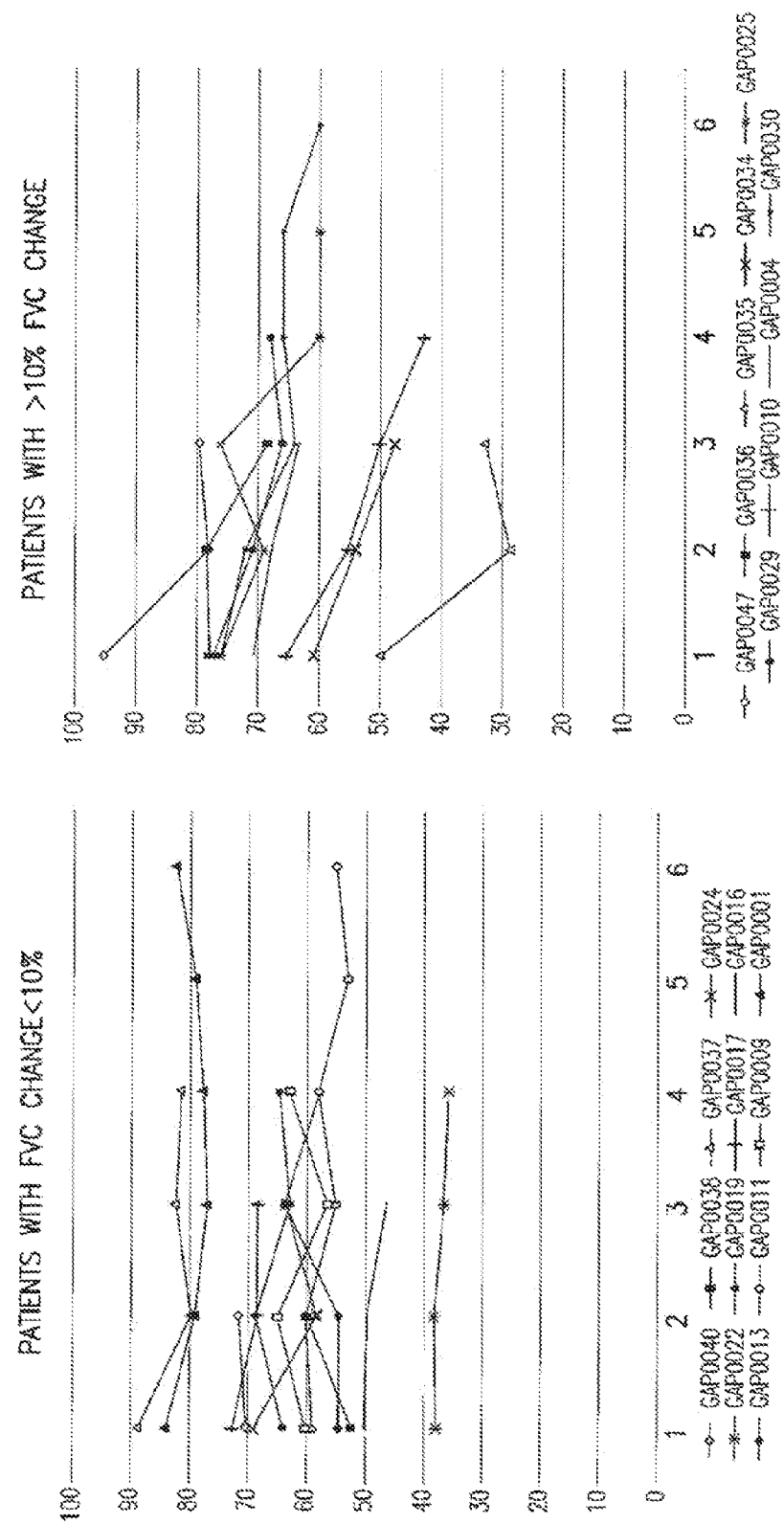

FIG. 6. Change in pulmonary function tests (PFT) over time. The number on the ordinate indicates the number of the FVC % measurement, first through sixth. Average time between visits was 100 days.

Figure 7:
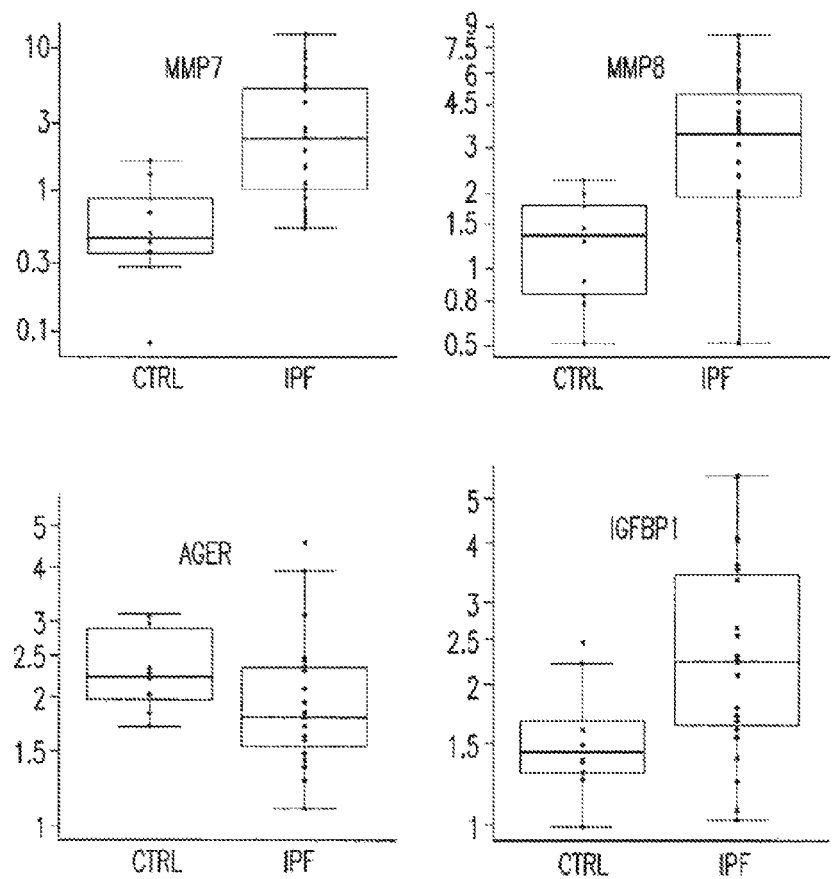

FIG. 7. Plasma protein levels of IPF versus controls new cohort (28 IPF, 10 controls).

Figure 8:
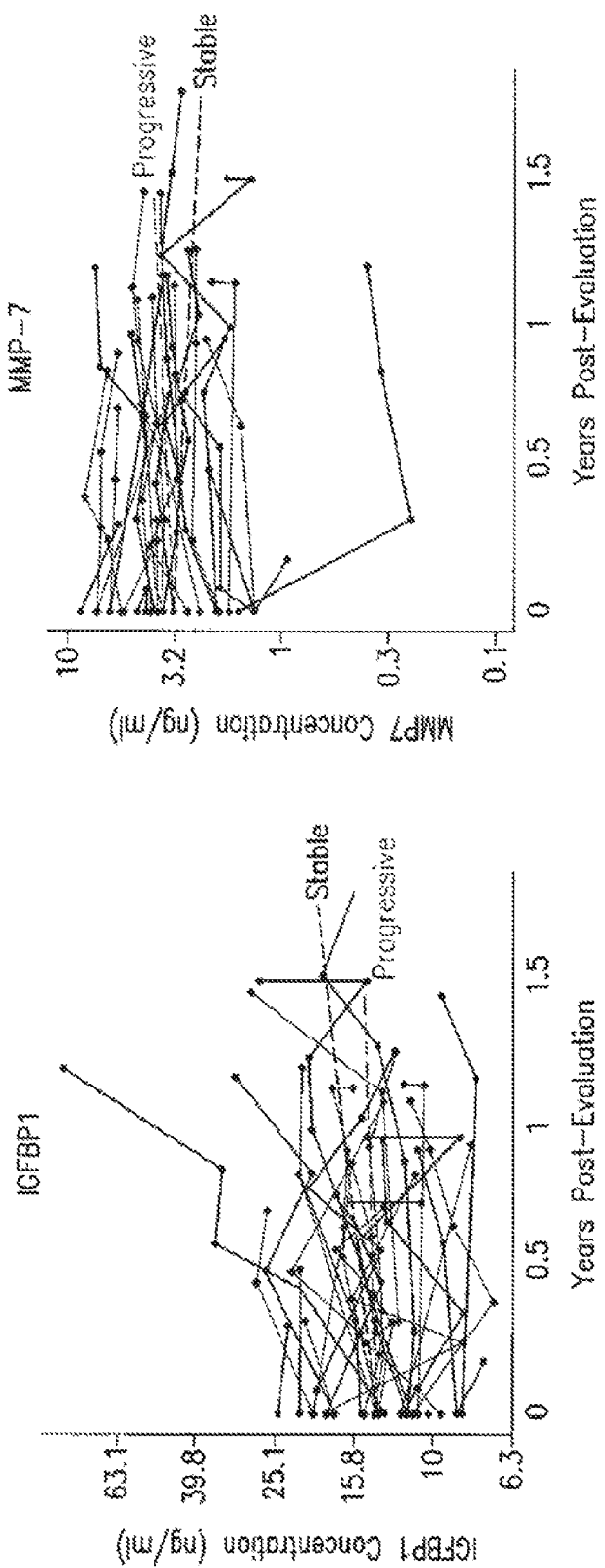

FIG. 8. Trend in IFGFBP1 and MMP7 concentrations.

Figure 9:
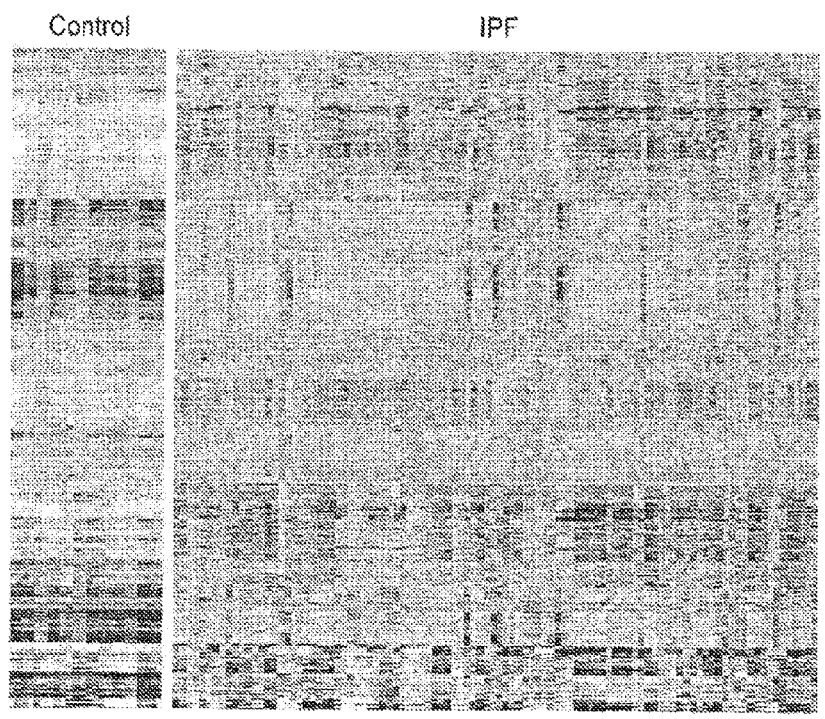

FIG. 9. Heatmap of gene expression patterns in Peripheral Blood Mononuclear Cells (PBMC) obtained from IPF patients and controls.

FIG. 10. Functional theme analysis of genes changed during disease progression.

Figure 11:
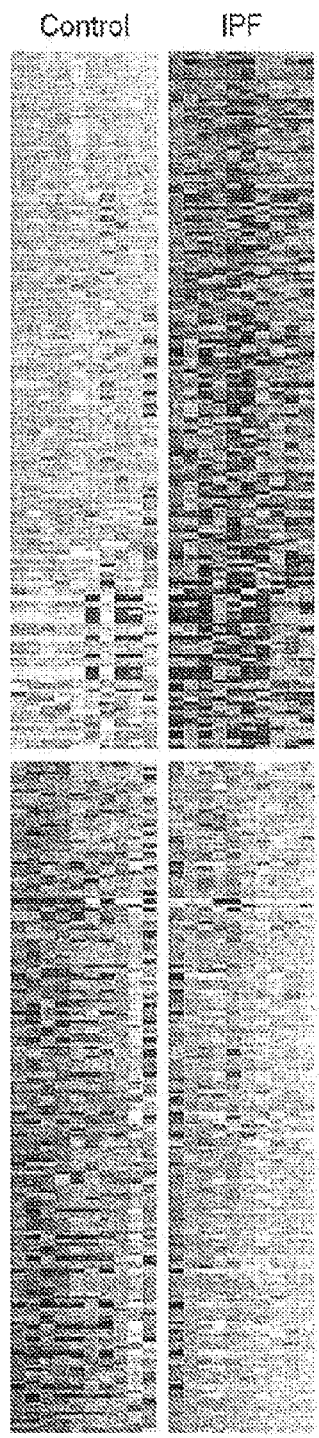

FIG. 11. Heatmap of the top 318 genes having a fold change>2 and FDR<5%. A comparison between 10 IPF patients and 10 Controls from the University of Pittsburgh cohort showed a difference of 1019 genes with FDR<5%, if a Fold change>2 is added, the difference is reduced to 162 up-regulated genes and 156 down-regulated genes.

Figure 12:
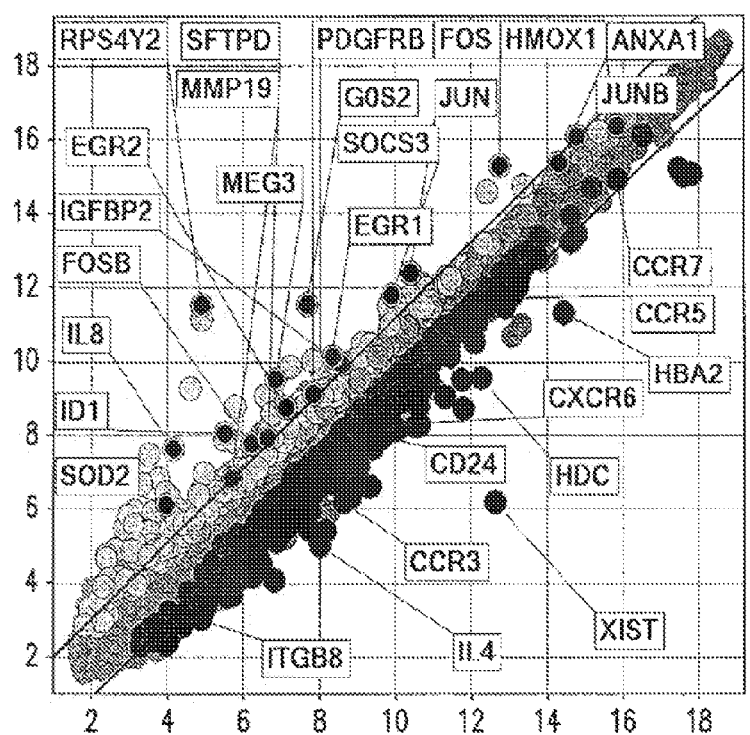

FIG. 12. Selected genes that distinguished IPF from Controls. Representation of the genes that differentiated IPF from control in the cohort of IPF patients from the University of Pittsburgh. ID1, SFTPD and MEG3 were among the up-regulated genes, and CCR7 and IL4 were among the down-regulated genes FIG. 13. Comparison of commonly expressed genes between University of Pittsburgh and University of Chicago IPF cohorts. The genes in the right upper part are the commonly expressed up-regulated genes in the two cohorts, the commonly expressed down-regulated genes are represented in the left lower part. The gene expression between the two IPF cohorts showed very similar patterns.

FIG. 14. A. Ingenuity Tox list analysis of the top up-regulated genes showed enrichment for annotations related to oxidative stress, TGF-B signaling pathway and acute phase response proteins. A Tax list by Ingenuity of the top up-regulated genes in IPF showed gene enrichment for known mechanisms involved in the disease such as the TGF-B signaling and oxidative stress pathways. These genes were also enriched with annotations related to cellular growth proliferation and morphology. B. Ingenuity analysis of the top down-regulated genes in IPF showed enrichment in annotations related to cellular development and antigen presentation. The enrichment analysis of the top down regulated genes in IPF showed annotations related to cellular development, antigen presentation and cell death. The Tox list didn't show enrichment in this group.

Figure 15:
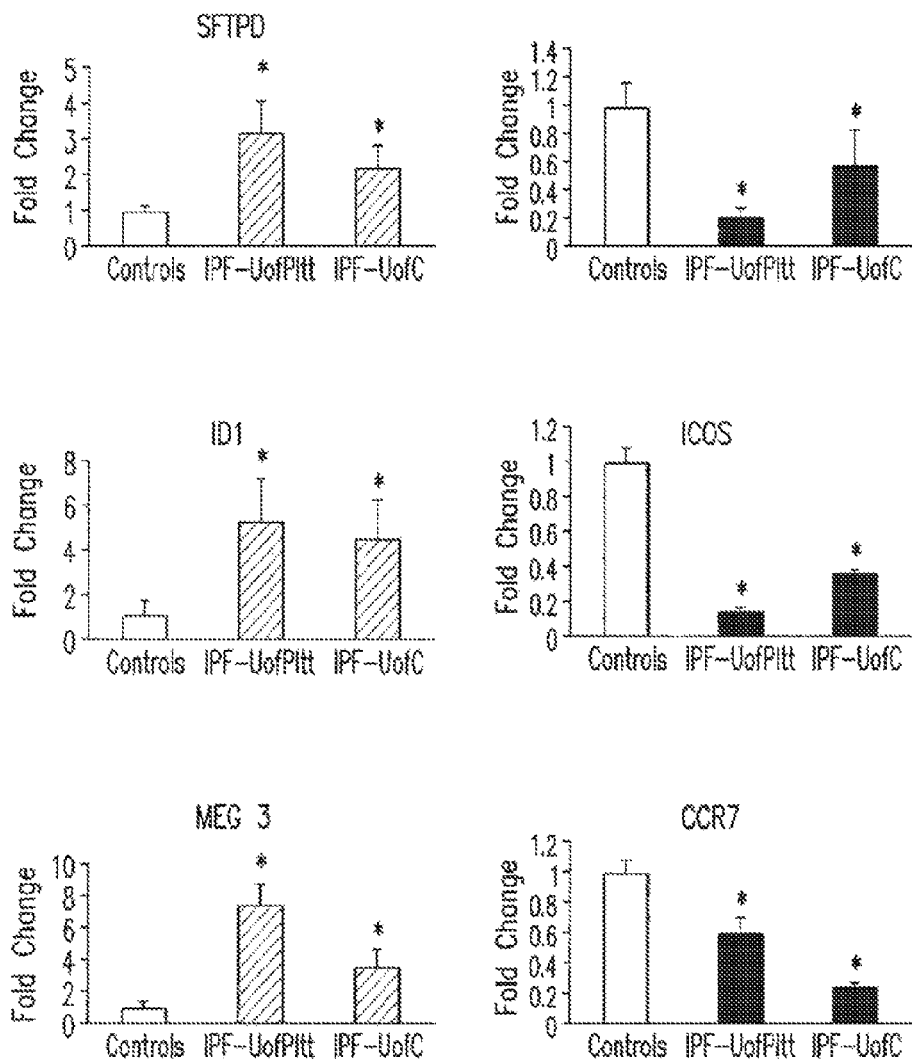

FIG. 15. qRT-PCR showed similar gene expression in the two independent cohorts (University of Pittsburgh and University of Chicago) of patients with IPF. Validation was performed in commonly expressed genes in the two cohorts by microarray (ID1, IL4, CCR7, ICOS), and in the differentially expressed genes with probes unique to the Agilent microarray platform (SFTPD and MEG3). Similar values were found for all the validated genes in the two independent cohorts with statistically significant difference when compare to controls.

Figure 16:
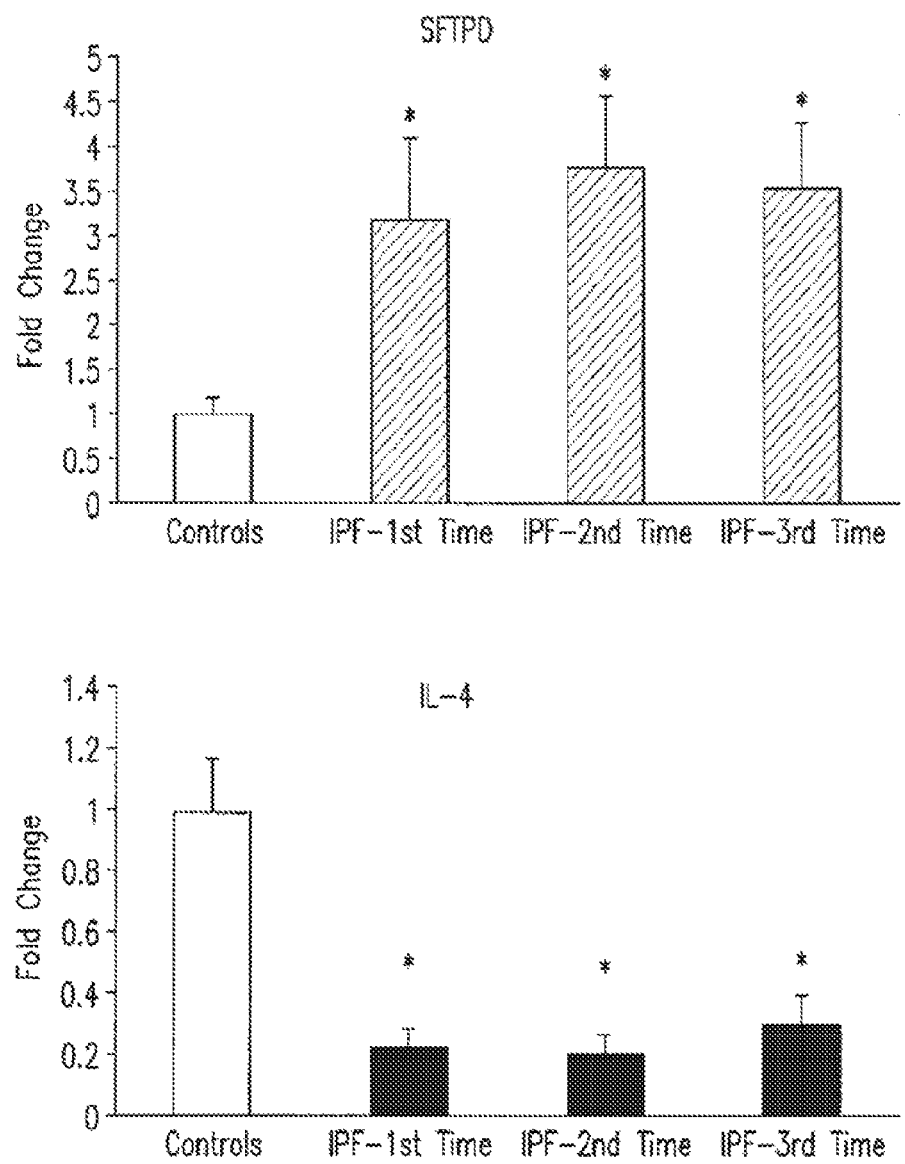

FIG. 16. Time course analysis by qRT-PCR of SFTPD and IL-4 in 20 IPF patients showed consistent values. A biomarker filter performed of the top up-regulated and down-regulated genes by Ingenuity showed SFTPD and IL-4 as candidate biomarkers in PBMC. 20 patients with IPF were followed during a period of 10 months with an average interval of five months between visits. qRT-PCR average showed consistent increase of SFTPD at each time point with statistically significant values when compare to controls, the opposite phenomenon was found with the expression of IL-4.

Figure 17:
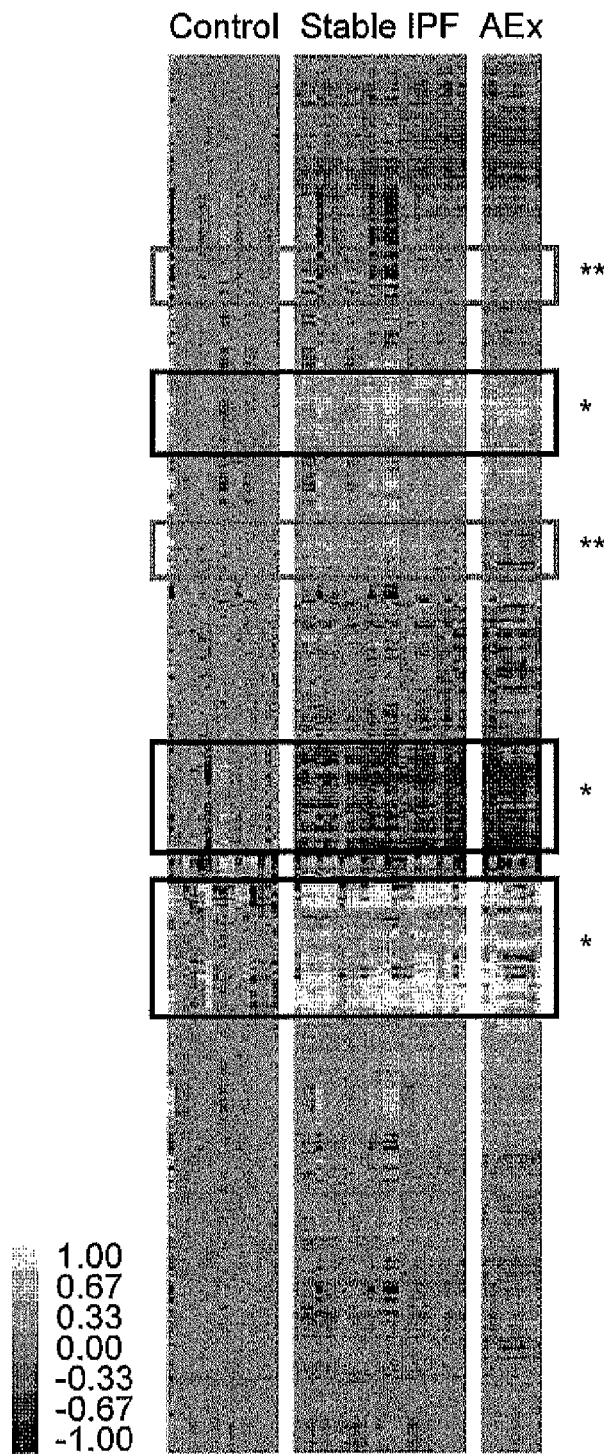
Figure 18C:
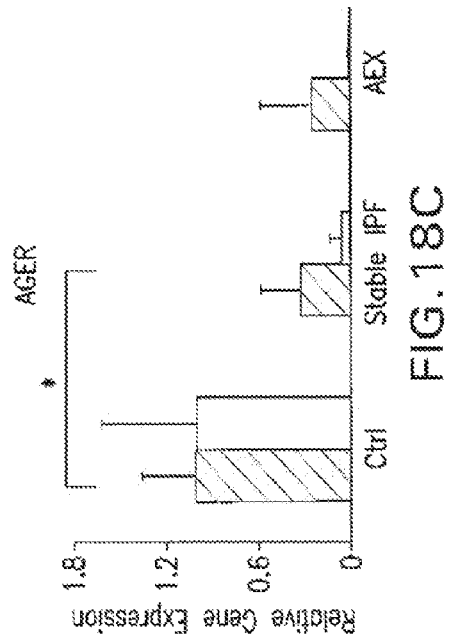
Figure 18D:
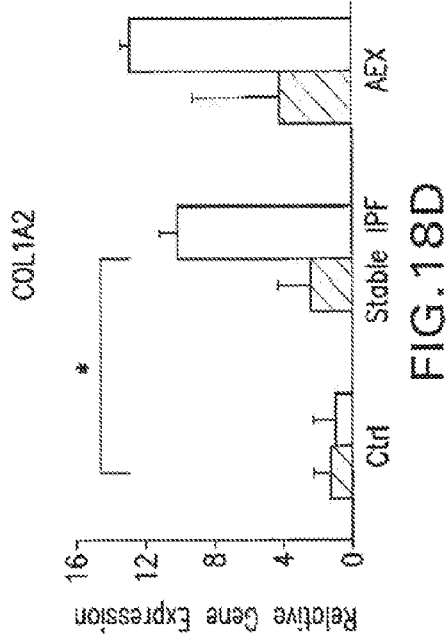
Figure 18A:
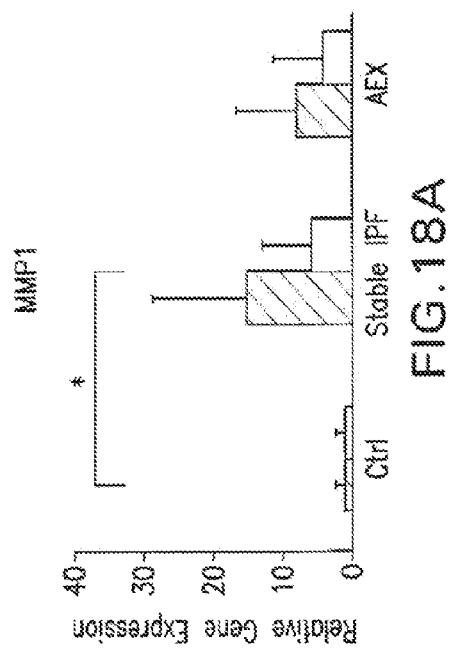
Figure 18B:
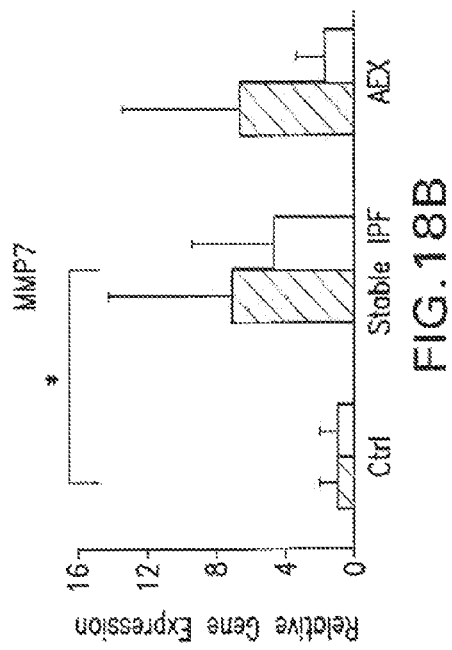

FIG. 17. When compared with control samples, gene expression signatures of acute exacerbation of IPF (IPF-AEx) and IPF are similar, as demonstrated in the heatmap. Every row represents a gene and every column represents a patient. The rectangles with asterisk (*) represent genes expressing similar patterns in IPF and IPF-AEx; the rectangles with double asterisks (**) represent genes expressing different patterns in IPF and IPF-AEx.

FIG. 18A-D. Relative gene expression levels of representative genes that distinguish idiopathic pulmonary fibrosis (IPF) from control samples, and their behavior in acute exacerbation of IPF (IPF-AEx). Gene expression levels of (A) MMP1, (B) MMP1, (C) AGER, and COL1A2 (D) were measured by microarray (hatched bars) and real-time quantitative reverse transcription-polymerase chain reaction (qRTPCR) (solid bars) (*q<5 by microarray and P<0.05 by qRT-PCR).

FIG. 19A-D. Signature of acute exacerbation of IPF (IPF-AEx) and validation of up-regulation of CCNA2. A. Direct comparison of stable IPF with IPF-AEx reveals 579 differentially expressed genes between these two groups, as shown in the heatmap. B. Among them CCNA2 was one of the most up-regulated genes in the IPF-AEx group. C. CCNA2 gene expression as determined by (hatched bars) microarray was confirmed by (solid bars) real-time quantitative reverse transcriptionpolymerase chain reaction (qRT-PCR). D. CCNA2 protein expression was determined by Western blot (*q<5 for microarray and P<0.05 for qRT-PCR).

Figure 20:
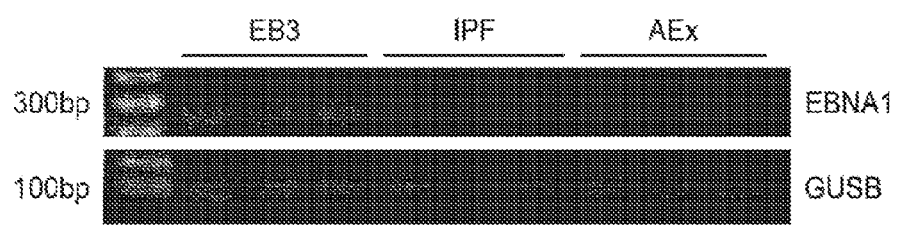

FIG. 20. RT-PCR for EBNA1 showed negative for both stable IPF and IPF-AEx. EB3 B-cell lymphoma cell line was used for positive control.

Figure 21:
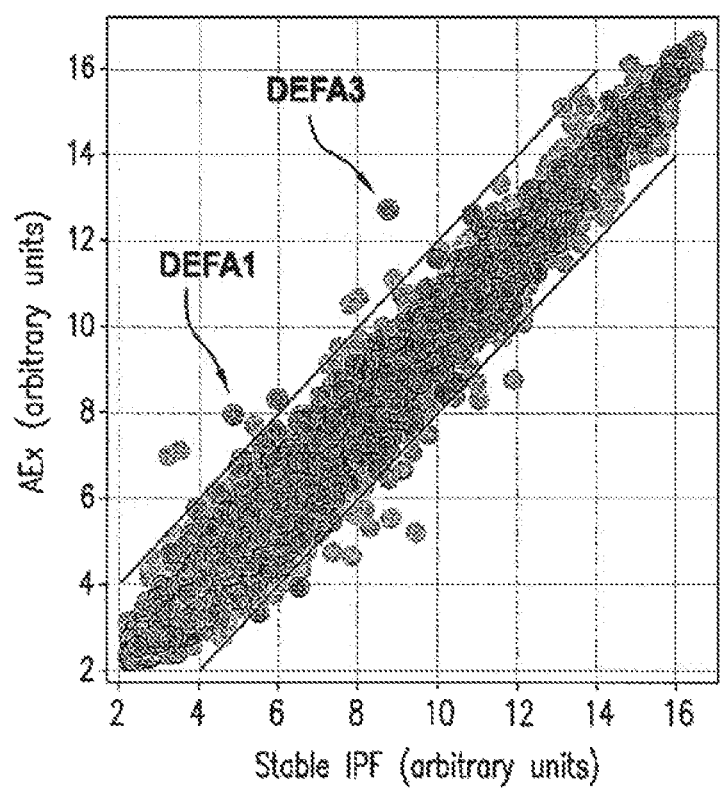

FIG. 21. A scatter plot of the genes involved in viral infections annotated by the gene ontology (GO) database. X axis represents average gene expression in IPF; Y axis represents average gene expression in IPF-AEx. The two solid lines indicate two-fold-change difference between the groups. Except for α-defensins, most of the highlighted spots are within two solid lines that indicate 2-folds change.

FIG. 22A-L. A-C. Localization of CCNA2 in tissue obtained from patients with IPF-AEx (original magnifications: A, 320; B, 320; C, 320 merge): CCNA2 (green) is co-localized with cytokeratin (red). D-F. CCNA2 (green) does not co-localize with vimentin (red) (original magnifications: D, 320; E, 320; F, 320 merge). G and H. Confocal microscopy of CCNA2 and cytokeratin. CCNA2 (green) and cytokeratin are co-localized in the basal portion of bronchial epithelium (G; original magnification, 340). Co-expression of CCNA2 and cytokeratin is also observed in the alveolar epithelium (H; original magnification, 360). Co-expression of CCNA2 (green) and Ki-67 (red), a proliferation marker, is observed in IPF-AEx tissue (I; original magnification, 340). In situ terminal deoxynucleotidyltransferase dUTP nick end-labeling (TUNEL) reveals positive stains in hyaline membranes (arrows in J; original magnification, 340) and alveolar epithelium (arrows in K; original magnification, 340) in lung tissues with diffuse alveolar damage superimposed on the usual interstitial pneumonia pattern. In lungs with normal morphology, TUNEL-positive structures are observed predominantly in the alveolar macrophages (arrows in L; original magnification, 340).

FIG. 23A-F. A. Gene expression of α-defensins (DEFA1-3) observed by microarray (hatched bars) or real-time quantitative reverse transcription-polymerase chain reaction (solid bars). Gene expression levels of α-defensins were significantly higher in patients with IPF-AEx compared with patients with stable IPF or control subjects. B. ELISA for α-defensins in plasma obtained from control subjects, patients with stable IPF, and patients with IPF-AEx. Plasma levels of α-defensins in patients with IPF-AEx were significantly higher (*q<5 for microarray and P<0.05 for ELISA). C-E. Histological localization of α-defensins in tissues from patients with IPF-AEx (original magnification, 360). C. (green) α-Defensins were present in cells expressing surfactant protein C (D, red and E, merge), suggesting type II pneumocytes as one of the cellular sources for α-defensins. F. α-Defensins are elevated in the peripheral blood of patients with IPF-Aex. The panel shows the result of ELISA with plasma obtained from IPF-Aex patients. α-Defensin levels also showed the tendency to elevate in the pre- and post-acute exacerbations groups.

Figure 24:
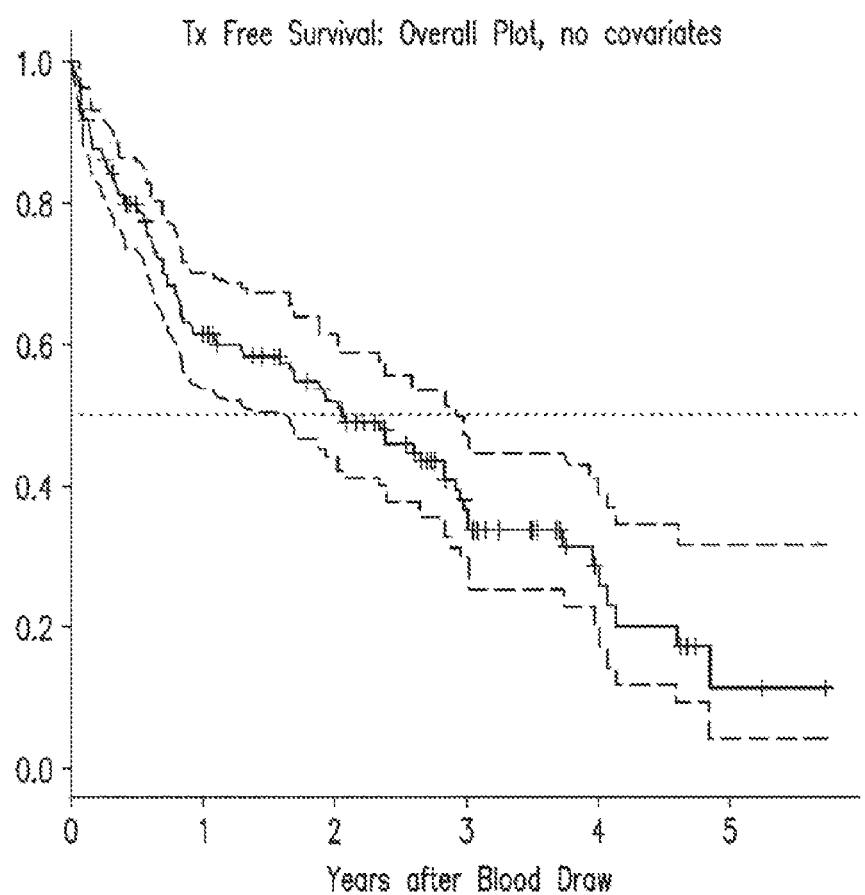

FIG. 24. Transplant-free survival for IPF patients (see Table 11). Median interval from blood draw to lung transplant or death was 2.1 years, 95% C.I. 1.6 to 2.9 years FIG. 25. Transplant-free survival with respect to plasma concentration of MMP7 for IPF patients. The median interval from blood draw to lung transplant or death for patients whose plasma concentrations of MMP7 were at least 4426 pg/mL, was 1.1 years, and the median interval to lung transplant or death for patients whose plasma concentrations of MMP7 were less than 4426 pg/mL, was 3.0 years. The p value for comparing the interval to lung transplant or death with respect to plasma concentrations of MMP7 was 0.003.

Figure 26:
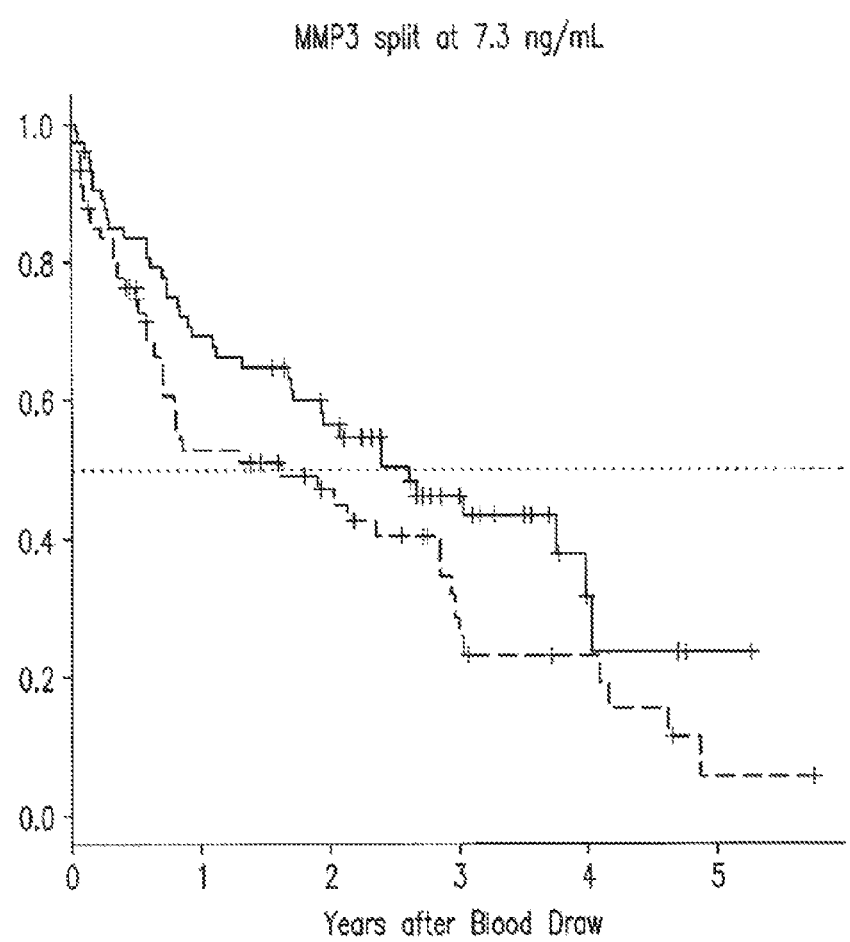

FIG. 26. Transplant-free survival with respect to plasma concentration of MMP3 for IPF patients. The median interval from blood draw to lung transplant or death, for patients whose plasma concentrations of MMP3 were at least 7.3 ng/mL, was 1.6 years, and the median interval to lung transplant or death for patients whose plasma concentrations of MMP3 were less than 7.3 ng/mL, was 2.6 years. The p value for comparing the interval to lung transplant or death with respect to plasma concentrations of MMP3 was 0.05.

Figure 27:
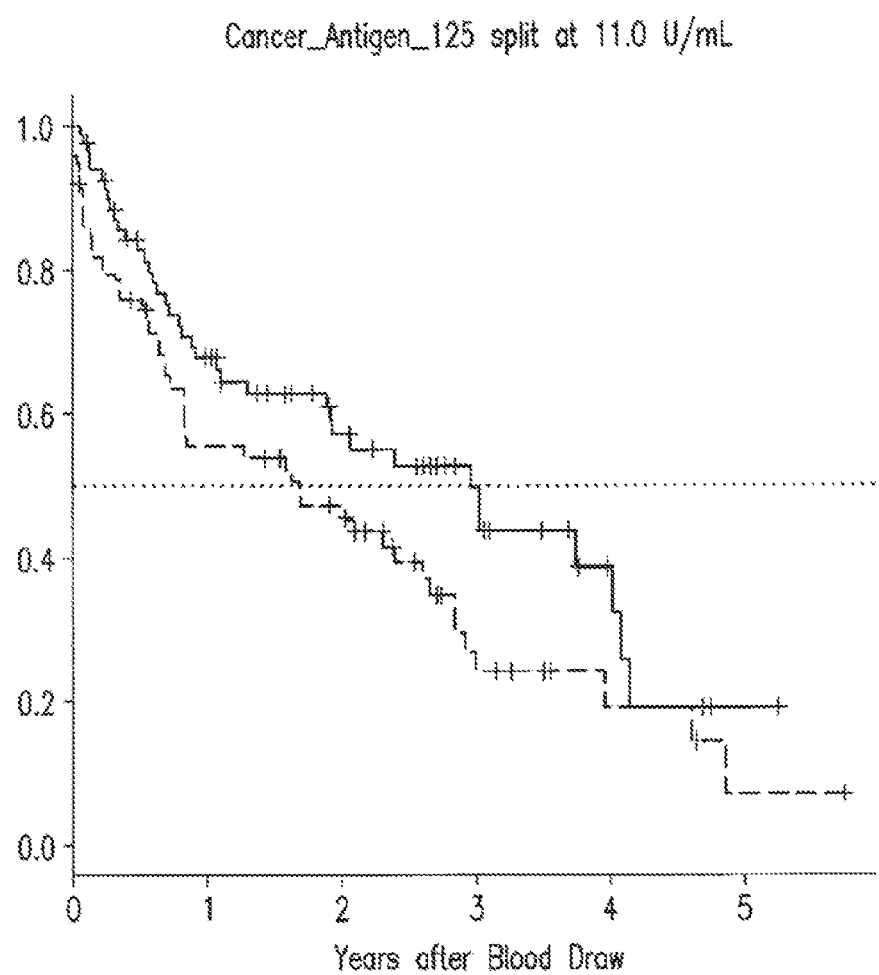

FIG. 27. Transplant-free survival with respect to plasma concentration of Cancer_Antigen_125 (CA125) for IPF patients. The median interval from blood draw to lung transplant or death for patients whose plasma concentrations of CA125 were at least 11.0 U/mL, was 1.7 years, and the median interval to lung transplant or death for patients whose plasma concentrations of CA125 were less than 11.0 U/mL, was 3.0 years. The p value for comparing the interval to lung transplant or death with respect to plasma concentrations of CA125 was 0.048.

Figure 28:
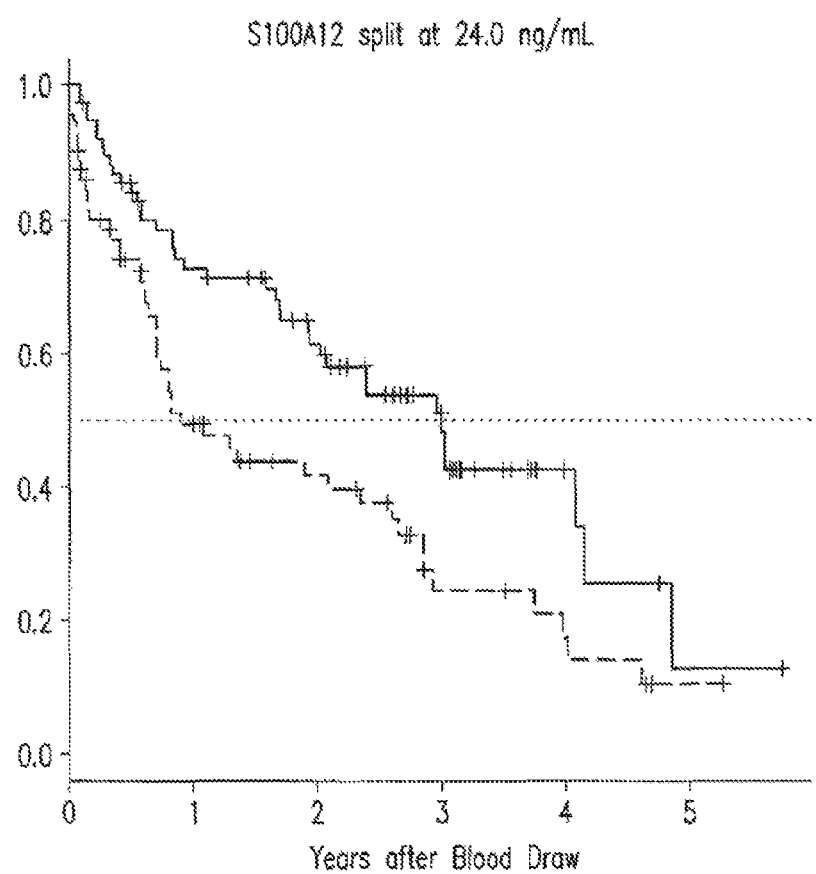

FIG. 28. Transplant-free survival with respect to plasma concentration of S100A12 for IPF patients. The median interval from blood draw to lung transplant or death for patients whose plasma concentrations of S100A12 were at least 24.0 ng/mL, was 0.9 years, and the median interval to lung transplant or death for patients whose plasma concentrations of S100A12 were less than 24.0 ng/mL, was 3.0 years. The p value for comparing the interval to lung transplant or death with respect to plasma concentrations of S100A12 was 0.005.

Figure 29:
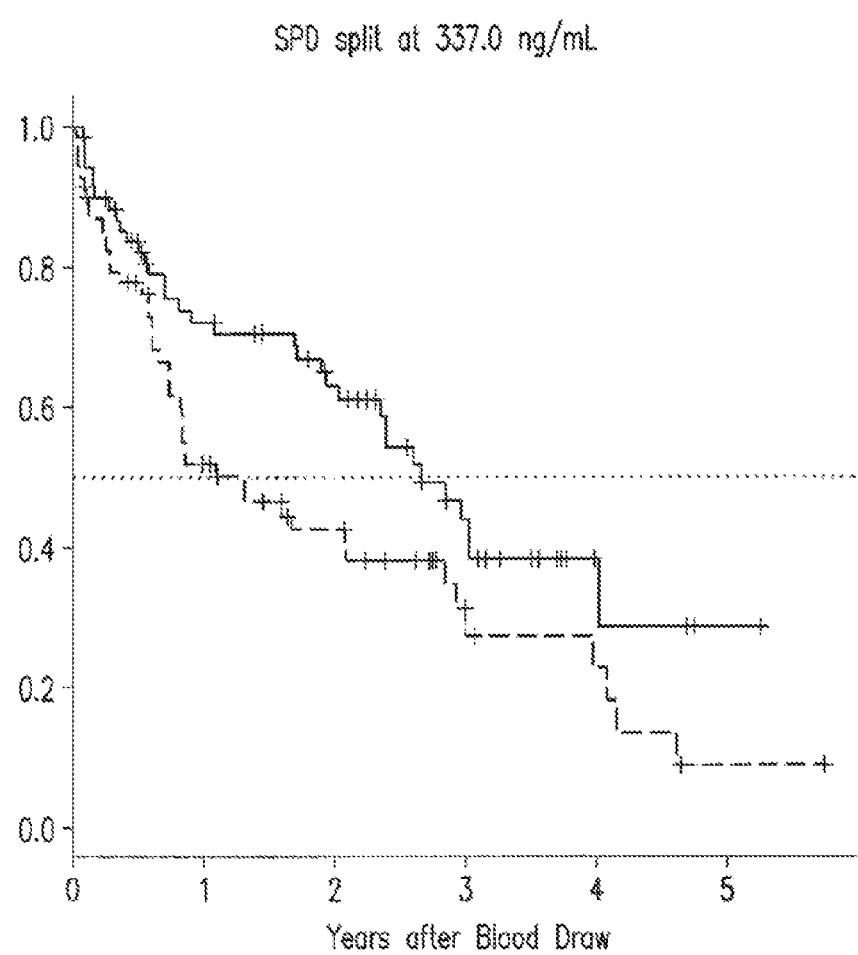

FIG. 29. Transplant-free survival with respect to plasma concentration of SPD for IPF patients. The median interval from blood draw to lung transplant or death for patients whose plasma concentrations of SPD were at least 337.0 ng/mL, was 1.3 years, and the median interval to lung transplant or death for patients whose plasma concentrations of SPD were less than 337.0 ng/mL, was 2.7 years. The p value for comparing the interval to lung transplant or death with respect to plasma concentrations of SPD was 0.03.

Figure 30:
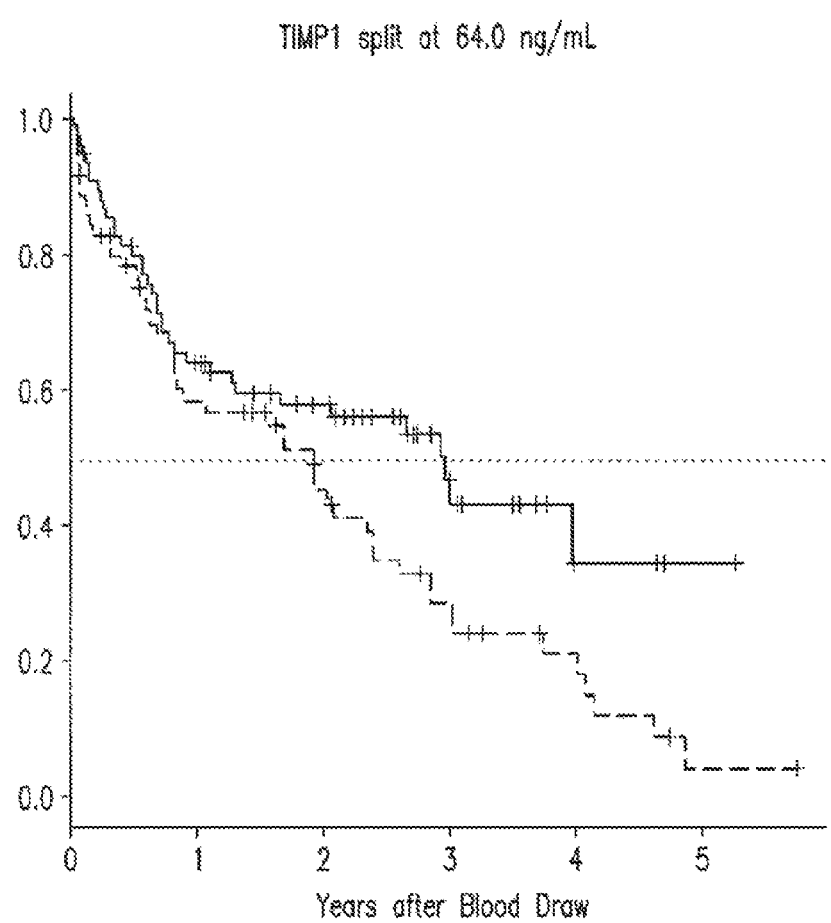

FIG. 30. Transplant-free survival with respect to plasma concentration of TIMP1 for IPF patients. The median interval from blood draw to lung transplant or death for patients whose plasma concentrations of TIMP1 were at least 64.0 ng/mL was 1.9 years, and the median interval to lung transplant or death for patients whose plasma concentrations of TIMP1 were less than 64.0 ng/mL, was 3.0 years. The p value for comparing the interval to lung transplant or death with respect to plasma concentrations of TIMP1 was 0.037.

Figure 31:
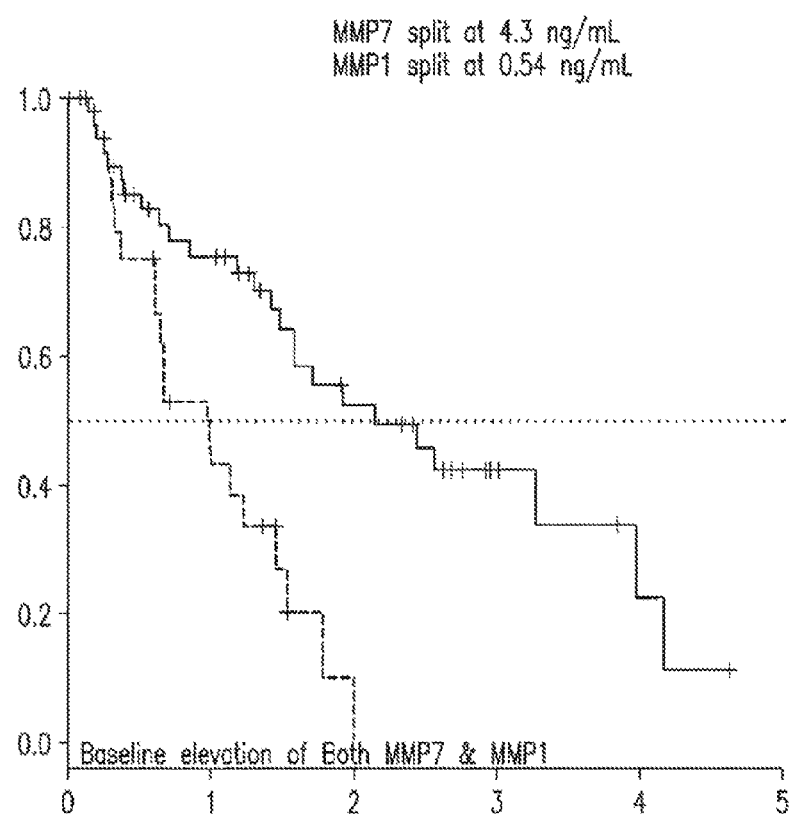

FIG. 31. Progression-free survival with respect to plasma concentrations of MMP7 and MMP1 for patients who did receive lung transplant. The median interval from blood draw to 10% or greater decline in FVC % predicted within one year, for patients whose plasma concentrations of MMP7 and MMP1 were at least 4.3 ng/mL and 0.54 ng/mL, respectively, was 0.98 years, and the median interval from blood draw to 10% or greater decline in FVC % predicted within one year for patients whose plasma concentrations of MMP7 and MMP1 did not both exceed 4.3 ng/mL and 0.54 ng/mL, respectively, was 2.0 years. The p value for comparison of progression-free survival with respect to plasma concentrations of MMP7 and MMP1 was 0.016.

Figure 32:
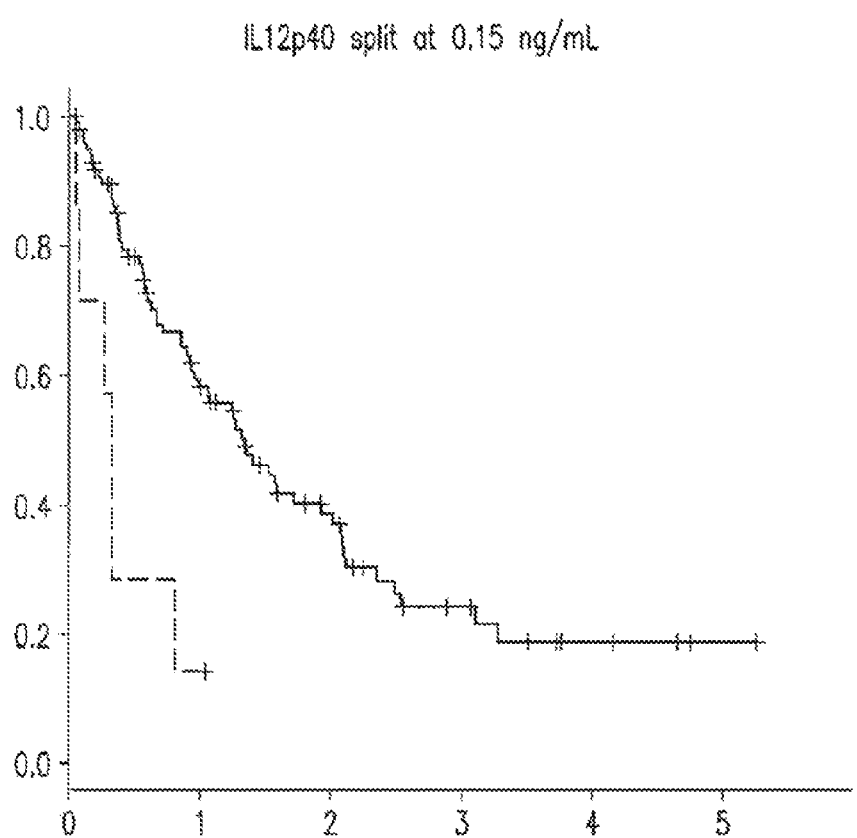

FIG. 32. Progression-free survival with respect to plasma concentration of IL12p40 for patients who did not receive lung transplant. The median interval from blood draw to 10% or greater decline in FVC % predicted within one year, for patients whose plasma concentrations of IL12p40 were at least 0.15 ng/mL, was 0.3 years, and the median interval from blood draw to 10% or greater decline in FVC % predicted within one year, for patients whose plasma concentrations of IL12p40 were less than 0.15 ng/mL was 1.3 years. The p value for comparison of progression-free survival with respect to plasma concentrations of IL12p40 was 0.0003.

Figure 33:
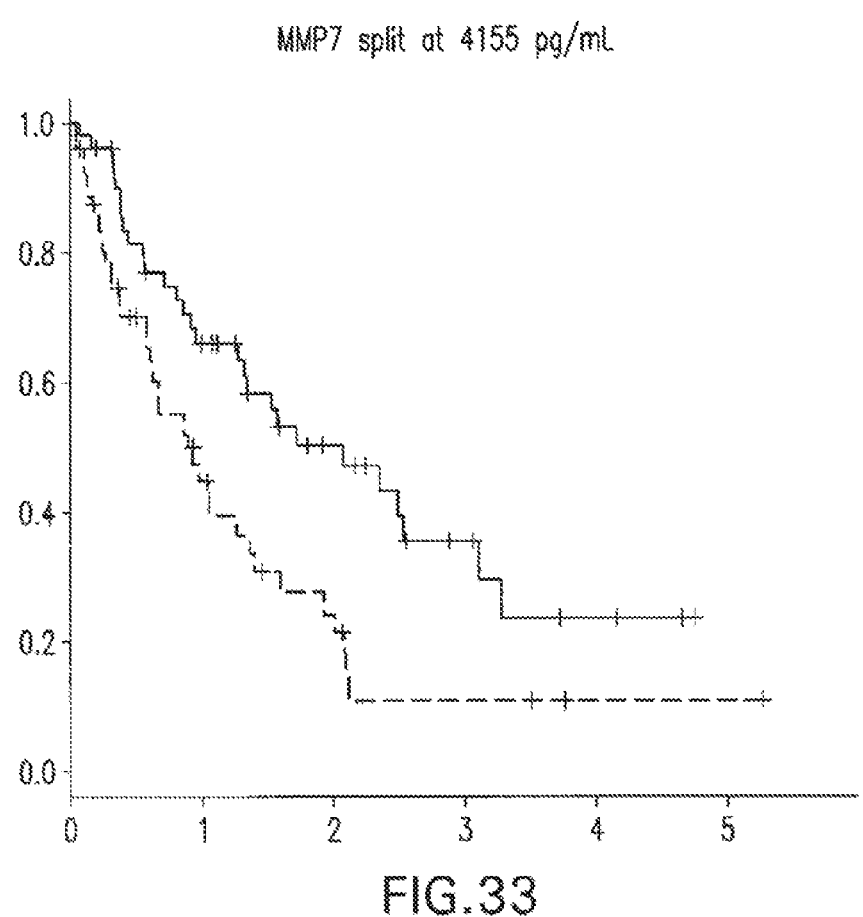

FIG. 33. Progression-free survival with respect to plasma concentration of MMP7 for patients who did not receive lung transplant. The median interval from blood draw to 10% or greater decline in FVC % predicted within one year, for patients whose plasma concentrations of MMP7 were at least 4155 pg/mL, was 0.9 years, and the median interval from blood draw to 10% or greater decline in FVC % predicted within one year, for patients whose plasma concentrations of MMP7 were less than 4155 pg/mL, was 2.1 years. The p value for comparison of progression-free survival with respect to plasma concentrations of MMP7 was 0.006.

Figure 34:
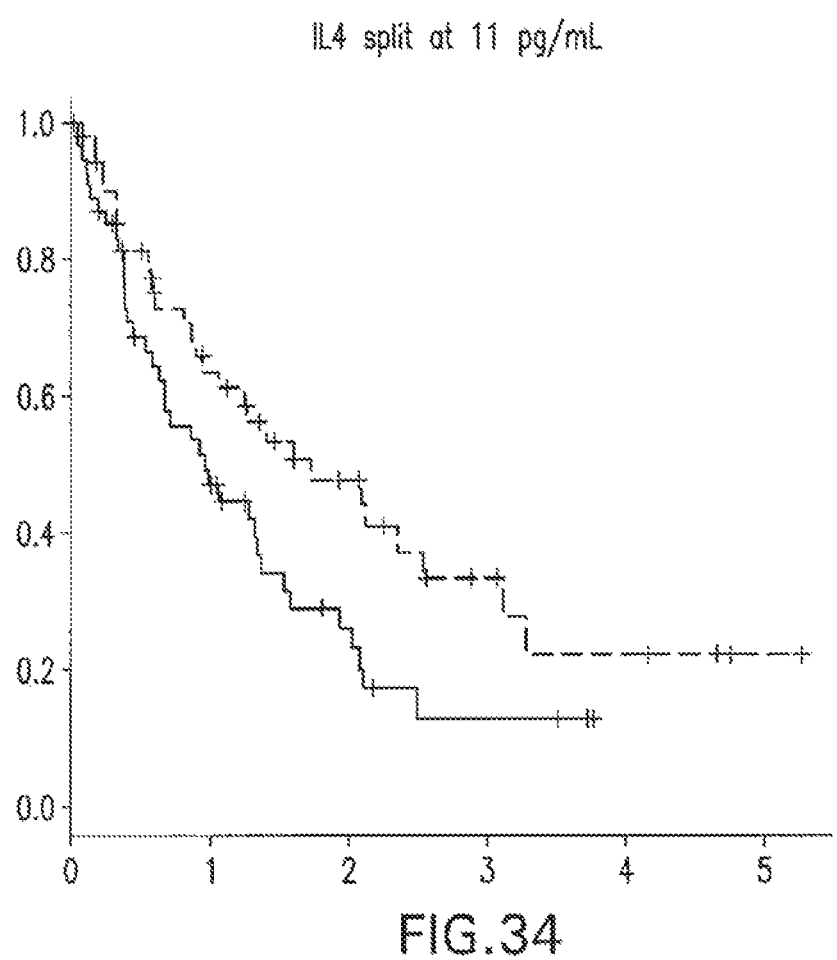

FIG. 34. Progression-free survival with respect to plasma concentration of IL4 for patients who did not receive lung transplant. The median interval from blood draw to 10% or greater decline in FVC % predicted within one year, for patients whose plasma concentrations of IL4 were at least 11 pg/mL, was 0.9 years, and the median interval from blood draw to 10% or greater decline in FVC % predicted within one year, for patients whose plasma concentrations of IL4 was less than 11 pg/mL was 1.7 years. The p value for comparison of progression-free survival with respect to plasma concentrations of IL4 was 0.04.

Figure 35:
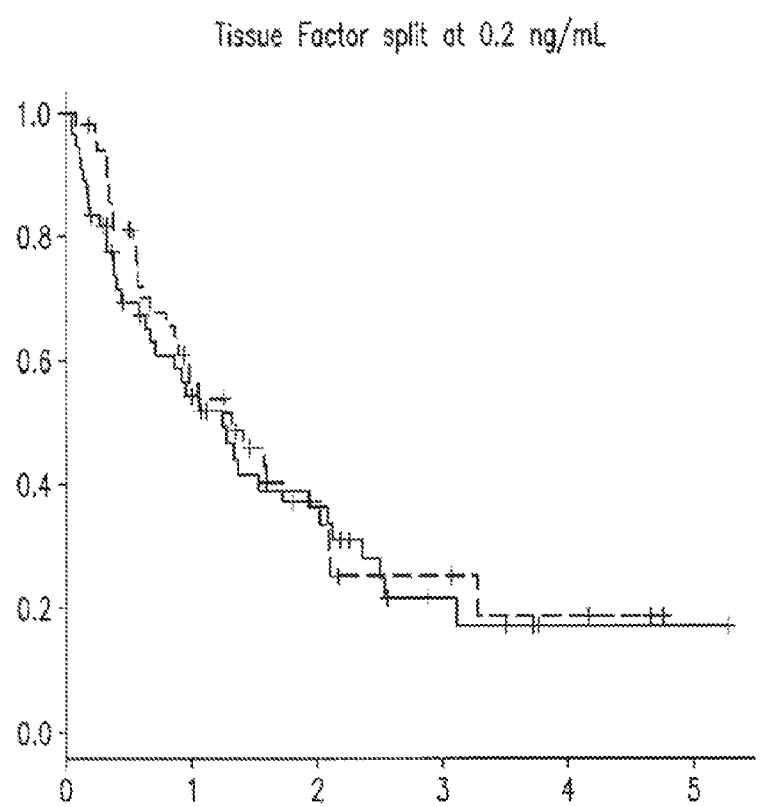

FIG. 35. Progression-free survival with respect to plasma concentration of Tissue Factor for patients who did not receive lung transplant. The median interval from blood draw to 10% or greater decline in FVC % predicted within one year, for patients whose plasma concentrations of Tissue Factor were at least 0.2 ng/mL, was 1.3 years, and the median interval from blood draw to 10% or greater decline in FVC % predicted within one year, for patients whose plasma concentrations of Tissue Factor was less than 0.2 nng/mL was 1.3 years. The p value for comparison of progression-free survival with respect to plasma concentrations of Tissue Factor was 0.69.

Figure 36:
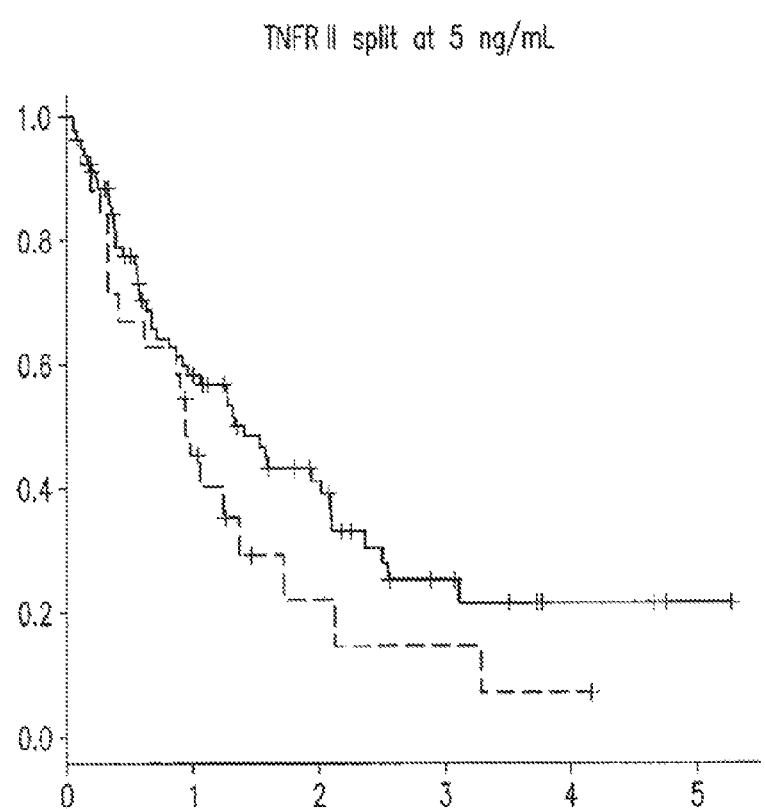

FIG. 36. Progression-free survival with respect to plasma concentration of TNFRII for patients who did not receive lung transplant. The median interval from blood draw to 10% or greater decline in FVC % predicted within one year, for patients whose plasma concentrations of TNFRII were at least 5 ng/mL, was 0.94 years, and the median interval from blood draw to 10% or greater decline in FVC % predicted within one year, for patients whose plasma concentrations of TNFRII were less than 5 ng/mL was 1.33 years. The p value for comparison of progression-free survival with respect to plasma concentrations of TNFRII was 0.13.

5. DETAILED DESCRIPTION OF THE INVENTION

The present invention relates to methods and kits for diagnosing or evaluating the progression of IPF.

For clarity of description, and not by way of limitation, the detailed description of the invention is divided into the following subsections:
(i) markers for IPF diagnosis;
(ii) markers for IPF progression;
(iii) methods of use; and
(iv) kits.

5.1 Markers for IPF Diagnosis

The present invention provides for panels of plasma markers which may be used to establish a diagnosis of IPF and to distinguish this condition from other lung diseases with substantial confidence (preferably, but not by limitation, a sensitivity and specificity each of which are at least 90 percent and more preferably at least 95 percent).

In one set of non-limiting embodiments, the panel comprises MMP7, MMP1, and MMP8 as well as either or both of IGFBP1 and TNFRSF1A. In particular non-limiting embodiments, if there are additional markers included in the panel, MMP7, MMP1, MMP8 and IGFBP1 and/or TNFRSF1A constitute at least 20 percent, at least 30 percent, at least 40 percent, at least 50 percent, at least 60 percent, at least 70 percent, at least 80 percent, at least 90 percent or at least 95 percent of the total markers present in the panel.

In another set of non-limiting embodiments, the panel comprises MMP7, MMP1, MMP8 and AGER as well as either or both of IGFBP1 and TNFRSF1A. In particular non-limiting embodiments, if there are additional markers included in the panel, MMP7, MMP1, MMP8, AGER and IGFBP1 and/or TNFRSF1A constitute at least 20 percent, at least 30 percent, at least 40 percent, at least 50 percent, at least 60 percent, at least 70 percent, at least 80 percent, at least 90 percent or at least 95 percent of the total markers present in the panel.

In another set of non-limiting embodiments, the panel comprises MMP7, MMP1, MMP8 and at least two, at least three, at least four, at least five, at least six, at least seven, at least eight, at least nine, or at least ten, or at least fifteen, or at least twenty, markers selected from the group consisting of IGFBP1, TNFRSF1A, TNFRSF1B, MMP2, MMP3, AGER, CXCL10, CCL11, CCL2, FAS, IL12B, IL1RA, S100A12, B2M, MPO, ICAM-1, TF, VWF, SPA, SPD, MUC1 (KL-6), SFTPD, ID1, MEG-3, IL4, CCR7, ICOS, CA125, TIMP1, and IL12P40. In particular non-limiting embodiments, if there are additional markers included in the panel, MMP7, MMP1, MMP8 and the at least two at least three, at least four, at least five, at least six, at least seven, at least eight, at least nine, or at least ten, or at least fifteen, or at least twenty, of IGFBP1, TNFRSF1A, TNFRSF1B, MMP2, MMP3, AGER, CXCL10, CCL11, CCL2, FAS, IL12B, IL1RA, S100A12, B2M, MPO, ICAM-1, TF, VWF, SPA, SPD, MUC1 (KL-6), SFTPD, ID1, MEG3, IL4, CCR7, ICOS, CA125, TIMP1, and IL12P40 constitute at least 20 percent, at least 30 percent, at least 40 percent, at least 50 percent, at least 60 percent, at least 70 percent, at least 80 percent, at least 90 percent or at least 95 percent of the total markers present in the panel.

5.2 Markers for IPF Progression

The present invention provides for one or more marker of IPF progression.

In a first non-limiting embodiment, the marker of IPF progression is DEFA-1.

In a second non-limiting embodiment, the marker of IPF progression is DEFA-2.

In a third non-limiting embodiment, the marker of IPF progression is DEFA-3.

In a fourth non-limiting embodiment, the marker of IPF progression is S100A12.

In a fifth non-limiting embodiment, the marker of IPF progression is CCNA2.

In a sixth non-limiting embodiment, the marker of IPF progression is MMP7.

In a seventh non-limiting embodiment, the marker of IPF progression is IL12P40. In further non-limiting embodiments, the invention provides for a panel or markers correlating with IPF progression comprising at least two of the aforelisted markers of IPF progression, namely DEFA1, DEFA2, DEFA3, S100A12, CCNA2, MMP7, and IL12P40. In particular non-limiting embodiments, if there are additional markers included in the panel, the at least two of DEFA-1, DEFA-2, DEFA-3, S100A12, CCNA2, MMP7, and IL12P40 constitute at least 20 percent, at least 30 percent, at least 40 percent, at least 50 percent, at least 60 percent, at least 70 percent, at least 80 percent, at least 90 percent or at least 95 percent of the total markers present in the panel.

In further non-limiting embodiments, the invention provides for a panel of markers of IPF progression, comprising a marker selected from at least two, at least three, at least four, or at least five of the categories set forth in FIG. 10. In particular non-limiting embodiments, if there are additional markers included in the panel, said at least two, at least three, at least four, or at least five of the categories set forth in FIG. 10 constitute at least 20 percent, at least 30 percent, at least 40 percent, at least 50 percent, at least 60 percent, at least 70 percent, at least 80 percent, at least 90 percent or at least 95 percent of the total markers present in the panel.

5.3 Methods of Use

In a first set of non-limiting embodiments, the present invention provides for a method of diagnosing IPF in a subject, comprising measuring the plasma levels of a plurality of markers comprising the panel of markers MMP7, MMP1, and MMP8 as well as either or both of IGFBP1 and/or TNFRSF1a, wherein increases (relative to control values) in the levels of MMP7, MMP1, and MMP8 as well as either or both of IGFBP1 and TNFRSF1A collectively indicate a diagnosis of IPF (collectively meaning that these changes (here, increases) in the expression levels of all the genes in the panel together indicate a diagnosis of IPF, as opposed to change in a single gene level correlating with IPF).

In a second set of non-limiting embodiments, the present invention provides for a method of diagnosing IPF in a subject, comprising measuring the plasma levels of a plurality of markers comprising the panel MMP7, MMP1, MMP8 and AGER as well as either or both of IGFBP1 and TNFRSF1A, wherein increases (relative to control values) in the level of MMP7, MMP1, and MMP8 as well as either or both of IGFBP1 and TNFRSF1A, and a decrease (relative to a control value) in the level of AGER, collectively indicate a diagnosis of IPF.

In a third set of non-limiting embodiments, the present invention provides for a method of diagnosing IPF in a subject, comprising measuring the plasma levels of a plurality of markers, wherein changes (relative to control values) in the level of a panel of markers comprising MMP7, MMP1, MMP8 and at least two, at least three, at least four, at least five, at least six, at least seven, at least eight, at least nine, or at least ten, or at least fifteen, or at least twenty, markers selected from the group consisting of IGFBP1, TNFRSF1A, TNFRSF1B, MMP2, MMP3, AGER, CXCL10, CCL11, CCL2, FAS, IL12B, IL1RA, S100A12, B2M, MPO, ICAM-1, TF, VWF, SPA, SPD, MUC1 (KL-6), SFTPD, ID1, MEG3, IL4, CCR7, ICOS, CA125, TIMP1, and IL12P40 collectively indicate a diagnosis of IPF.

In a fourth set of non-limiting embodiments, the present invention provides for a method of diagnosing IPF in a subject, comprising measuring the plasma levels of a plurality of markers, wherein an increase in the plasma level of a plurality of at least two of, at least three of, at least four of or at least five of MMP7, MMP1, MMP8, IGFBP1, TNFRSF1A, SFTPD, ID-1, and/or MEG3, wherein said plurality preferably includes MMP7, indicates a diagnosis of IPF. Identifying a decrease in the plasma level of one or more of AGER, IL-4, ICOS and/or CCR7 further confirms the IPF diagnosis.

With regard to any of the diagnostic methods described in the preceding paragraph, a positive result indicative of the diagnosis of IPF may be followed by a further diagnostic step, including but not limited to bronchioalveolar lavage and/or surgical lung biopsy, to confirm the diagnosis. Where a surgical lung biopsy is performed, an IPF diagnosis is confirmed by showing a histologic pattern of usual interstitial pneumonia.

Plasma levels may be measured by any method known in the art, including but not limited to multiplex analysis as provided by the technology of Luminex Corp., Austin, Tex., as well as antibody array, ELISA (enzyme-linked immunoabsorbent assay), IRMA (two-site immunoradiometric assay), Western blot, flow cytometry, etc. Plasma levels may be evaluated essentially simultaneously or sequentially.

An "increase" as that term is used herein means an increase of at least about 25% or of at least about 50% relative to control (normal plasma/plasma) values or to the mean of a plurality of normal values.

A "decrease" as that term is used herein means a decrease of at least about 25% or of at least about 50% relative to control (normal plasma) values or to the mean of a plurality of normal values.

Table 1 presents a list of non-limiting specific examples of normal plasma values for particular markers. Note that other normal values are also possible according to the invention, for example, depending on sample population or method of measurement.

TABLE 1

| MARKER | MARKER (ABBREV.) | NORMAL PLASMA LEVEL (Interquartile Range) |
|---|---|---|
| Matrix metalloproteinase-7 | MMP7 | 1.0-1.7 ng/mL |
| Matrix metalloproteinase-1 | MMP1 | 0.13-0.36 ng/mL |
| Matrix metalloproteinase-8 | MMP8 | 0.5-1.3 ng/mL |
| Insulin-like growth factor binding protein-1 | IGFBP1 | 0.4-1.7 ng/mL |
| Advanced glycosylation end product-specific receptor | AGER | 1.1-13.5 ng/mL |
| ENRAGE | S100A12 | 5.4-11.0 ng/mL |
| Surfactant Protein D | SFTPD | 41.7-72.2 ng/mL |
| Interleukin 4 | IL4 | 7 pg/mL |

In a fifth set of non-limiting embodiments, the present invention provides for a method of identifying progression of IPF in a subject, comprising measuring the plasma level of MMP7 and optionally MMP1, wherein an increase (relative to a previous value in the subject) in the plasma level of MMP7 and optionally MMP1, indicates progression of IPF.

In a sixth set of non-limiting embodiments, the present invention provides for a method of identifying progression of IPF in a subject, comprising measuring the plasma level of DEFA-1, wherein an increase (relative to a previous value in the subject) in the plasma level of DEFA-1 indicates progression of IPF.

In a seventh set of non-limiting embodiments, the present invention provides for a method of identifying progression of IPF in a subject, comprising measuring the plasma level of DEFA-2, wherein an increase (relative to a previous value in the subject) in the plasma level of DEFA-2 indicates progression of IPF.

In an eighth set of non-limiting embodiments, the present invention provides for a method of identifying progression of IPF in a subject, comprising measuring the plasma level of DEFA-3, wherein an increase (relative to a previous value in the subject) in the plasma level of DEFA-3 indicates progression of IPF.

In a ninth set of non-limiting embodiments, the present invention provides for a method of evaluating prognostics for survival and/or identifying progression of IPF in a subject, comprising measuring the plasma level of S100A12, wherein an increase (relative to a previous value in the subject) in the plasma level of S100A12 indicates a prognostics of survival and progression of IPF.

In a tenth set of non-limiting embodiments, the present invention provides for a method of identifying progression of IPF in a subject, comprising measuring the plasma level of CCNA2, wherein an increase (relative to a previous value in the subject) in the plasma level of CCNA2 indicates progression of IPF.

In an eleventh set of non-limiting embodiments, the present invention provides for a method of identifying progression of IPF in a subject, comprising measuring the plasma level of IL12P40 wherein an increase (relative to a previous value in the subject) in the plasma level of IL12P40 indicates progression of IPF.

In a twelfth set of non-limiting embodiments, the present invention provides for a method of identifying progression of IPF in a subject, comprising measuring the plasma level of at least two markers selected from MMP7, DEFA-1, DEFA-2, DEFA-3, S100A12, CCNA2, and IL12P40, wherein an increase in MMP7, an increase in DEFA-1, an increase in DEFA-2, an increase in DEFA-3, an increase in S100A12, an increase in CCNA2, and an increase in IL12P40 indicate progression of IPF.

In a thirteenth set of non-limiting embodiments, the present invention provides for a method for evaluating the survival prognosis of an IPF patient, comprising determining the plasma concentration of MMP7 in a plasma sample from the patient, wherein if the plasma concentration is greater than or equal to 4426 pg/mL the prognosis for the patient, without transplant, is survival for 1.1 year and, if the plasma concentration is less than 4426 pg/mL, the prognosis for the patient, without transplant, is survival for 3.0 years, with a p value of 0.003. After determining the plasma concentration and the associated prognosis, the patient may then be advised regarding the prognosis and options for treatment (e.g. transplant), and may optionally receive one or more further diagnostic step (e.g., broncheolar lavage or biopsy) and or treatment (e.g., lung transplant).

In a fourteenth set of non-limiting embodiments, the present invention provides for a method for evaluating the survival prognosis of an IPF patient, comprising determining the plasma concentration of MMP3 in a plasma sample from the patient, wherein if the plasma concentration is greater than or equal to 7.3 ng/mL the prognosis for the patient, without transplant, is survival for 1.6 year and, if the plasma concentration is less than 7.3 ng/mL, the prognosis for the patient, without transplant, is survival for 2.6 years, with a p value of 0.05. After determining the plasma concentration and the associated prognosis, the patient may then be advised regarding the prognosis and options for treatment (e.g. transplant), and may optionally receive one or more further diagnostic step (e.g., broncheolar lavage or biopsy) and or treatment (e.g., lung transplant).

In a fifteenth set of non-limiting embodiments, the present invention provides for a method for evaluating the survival prognosis of an IPF patient, comprising determining the plasma concentration of CA125 in a plasma sample from the patient, wherein if the plasma concentration is greater than or equal to 11.0 U/mL the prognosis for the patient, without transplant, is survival for 1.7 year and, if the plasma concentration is less than 11.0 U/mL, the prognosis for the patient, without transplant, is survival for 3.0 years, with a p value of 0.048. After determining the plasma concentration and the associated prognosis, the patient may then be advised regarding the prognosis and options for treatment (e.g. transplant), and may optionally receive one or more further diagnostic step (e.g., broncheolar lavage or biopsy) and or treatment (e.g., lung transplant).

In a sixteenth set of non-limiting embodiments, the present invention provides for a method for evaluating the survival prognosis of an IPF patient, comprising determining the plasma concentration of S100A12 in a plasma sample from the patient, wherein if the plasma concentration is greater than or equal to 24.0 ng/mL the prognosis for the patient, without transplant, is survival for 0.9 year and, if the plasma concentration is less than 24.0 ng/mL, the prognosis for the patient, without transplant, is survival for 3.0 years, with a p value of 0.005. After determining the plasma concentration and the associated prognosis, the patient may then be advised regarding the prognosis and options for treatment (e.g. transplant), and may optionally receive one or more further diagnostic step (e.g., broncheolar lavage or biopsy) and or treatment (e.g., lung transplant).

In a seventeenth set of non-limiting embodiments, the present invention provides for a method for evaluating the survival prognosis of an IPF patient, comprising determining the plasma concentration of SPD in a plasma sample from the patient, wherein if the plasma concentration is greater than or equal to 337.0 ng/mL the prognosis for the patient, without transplant, is survival for 1.3 year and, if the plasma concentration is less than 337.0 ng/mL, the prognosis for the patient, without transplant, is survival for 2.7 years, with a p value of 0.03. After determining the plasma concentration and the associated prognosis, the patient may then be advised regarding the prognosis and options for treatment (e.g. transplant), and may optionally receive one or more further diagnostic step (e.g., broncheolar lavage or biopsy) and or treatment (e.g., lung transplant).

In an eighteenth set of non-limiting embodiments, the present invention provides for a method for evaluating the survival prognosis of an IPF patient, comprising determining the plasma concentration of TIMP1 in a plasma sample from the patient, wherein if the plasma concentration is greater than or equal to 64.0 ng/mL the prognosis for the patient, without transplant, is survival for 1.9 year and, if the plasma concentration is less than 64.0 ng/mL, the prognosis for the patient, without transplant, is survival for 3.0 years, with a p value of 0.037. After determining the plasma concentration and the associated prognosis, the patient may then be advised regarding the prognosis and options for treatment (e.g. transplant), and may optionally receive one or more further diagnostic step (e.g., broncheolar lavage or biopsy) and or treatment (e.g., lung transplant).

In a nineteenth set of non-limiting embodiments, the present invention provides for a method for evaluating the prognosis for disease progression of an IPF patient, comprising determining the plasma concentrations of MMP7 and MMP1 in a plasma sample from the patient, wherein if the plasma concentrations of MMP7 and MMP1, respectively, are greater than or equal to 4.3 ng/mL and 0.54 ng/mL, the prognosis for the patient, without transplant, is an interval of 0.98 year until progression, and, if the plasma concentrations of MMP7 and MMP1, respectively, are less than 4.3 ng/mL and 0.54 ng/ml, the prognosis for the patient, without transplant, is an interval of 2.0 years until progression, with a p value of 0.016. After determining the plasma concentrations and the associated prognosis, the patient may then be advised regarding the prognosis and options for treatment (e.g. transplant), and may optionally receive one or more further diagnostic step (e.g., broncheolar lavage or biopsy) and or treatment (e.g., lung transplant).

In a twentieth set of non-limiting embodiments, the present invention provides for a method for evaluating the prognosis for disease progression of an IPF patient, comprising determining the plasma concentration of IL12P40 in a plasma sample from the patient, wherein if the plasma concentration of IL12P40, is greater than or equal to 0.15 ng/mL, the prognosis for the patient, without transplant, is an interval of 0.3 year until progression, and, if the plasma concentration of IL12P40, is less than 0.15 ng/mL, the prognosis for the patient, without transplant, is an interval of 1.3 years until progression, with a p value of 0.0003. After determining the plasma concentrations and the associated prognosis, the patient may then be advised regarding the prognosis and options for treatment (e.g. transplant), and may optionally receive one or more further diagnostic step (e.g., broncheolar lavage or biopsy) and or treatment (e.g., lung transplant).

In a twenty-first set of non-limiting embodiments, the present invention provides for a method for evaluating the prognosis for disease progression of an IPF patient, comprising determining the plasma concentration of MMP in a plasma sample from the patient, wherein if the plasma concentration of MMP7, is greater than or equal to 4155 pg/mL, the prognosis for the patient, without transplant, is an interval of 0.9 year until progression, and, if the plasma concentration of MMP7, is less than 4155 pg/mL, the prognosis for the patient, without transplant, is an interval of 2.1 years until progression, with a p value of 0.006. After determining the plasma concentrations and the associated prognosis, the patient may then be advised regarding the prognosis and options for treatment (e.g. transplant), and may optionally receive one or more further diagnostic step (e.g., broncheolar lavage or biopsy) and or treatment (e.g., lung transplant).

In a twenty-second set of non-limiting embodiments, the present invention provides for a method for evaluating the prognosis for disease progression of an IPF patient, comprising determining the plasma concentration of IL4 in a plasma sample from the patient, wherein if the plasma concentration of IL4, is greater than or equal to 11 pg/mL, the prognosis for the patient, without transplant, is an interval of 0.9 year until progression, and, if the plasma concentration of IL4, is less than 11 pg/mL, the prognosis for the patient, without transplant, is an interval of 1.7 years until progression, with a p value of 0.04. After determining the plasma concentrations and the associated prognosis, the patient may then be advised regarding the prognosis and options for treatment (e.g. transplant), and may optionally receive one or more further diagnostic step (e.g., broncheolar lavage or biopsy) and or treatment (e.g., lung transplant).

With regard to any of the methods of identifying IPF progression described in the preceding paragraphs, a positive result indicative of progression of IPF may be followed by a further step, including a lung biopsy, broncheoalveolar lavage, and/or a recommendation that the subject receive a lung transplant or by such procedure itself.

5.4 Kits

In one set of non-limiting embodiments, the present invention provides for a kit comprising means for determining the plasma levels of a panel of markers comprising MMP7, MMP1, and MMP8 as well as either or both of IGFBP1 and TNFRSF1A, wherein said kit may be used in the diagnosis of IPF, and wherein, preferably, said aforelisted markers (MMP7, MMP1, MMP8 and IGFBP1 and/or TNFRSF1A) constitute at least 30 percent, at least 40 percent, at least 50 percent, at least 60 percent, at least 70 percent, at least 80 percent or at least 90 percent of the total markers in the panel. This latter phrase referring to preferred embodiments indicates that the means for determining the plasma levels of the listed markers constitute at least 30 percent, at least 40 percent, at least 50 percent, at least 60 percent, at least 70 percent, at least 80 percent or at least 90 percent of the total means for measuring marker levels present in the kit; so that, for example, if the means for measuring the plasma level of each marker is a species of antibody specific for each marker (or fragment thereof) bound to beads, then the number of types of antibody (or fragment thereof)-coated beads corresponding to the listed markers (e.g., in this paragraph MMP7, MMP1, MMP8 and IGFBP1 and/or TNFRSF1A) constitute at least 30 percent, at least 40 percent, at least 50 percent, at least 60 percent, at least 70 percent, at least 80 percent or at least 90 percent of the total number of types of antibody (or fragment thereof)-coated beads present in the kit.

In another set of non-limiting embodiments, the present invention provides for a kit comprising a means for determining the plasma levels of a panel of markers comprising MMP7, MMP1, MMP8 and AGER as well as either or both of IGFBP1 and TNFRSF1A, where said kit may be used in the diagnosis of IPF and wherein, preferably, said aforelisted markers (MMP7, MMP1, MMP8, AGER and IGFBP1 and/or TNFRSF1A) constitute at least 30 percent, at least 40 percent, at least 50 percent, at least 60 percent, at least 70 percent, at least 80 percent or at least 90 percent of the total markers in the panel.

In another set of non-limiting embodiments, the present invention provides for a kit comprising a means for determining the plasma levels of a panel of markers comprising MMP7, MMP1, MMP-8 and at least two, at least three, at least four, at least five, at least six, at least seven, at least eight, at least nine, or at least ten, or at least fifteen, or at least twenty, markers selected from the group consisting of IGFBP1, TNFRSF1A, TNFRSF1B, MMP2, MMP3, AGER, CXCL10, CCL11, CCL2, FAS, IL12B, IL1RA, S100A12, B2M, MPO, ICAM-1, TF, VWF, SPA, SPD MUC1 (KL-6), SFTPD, ID1, MEG3, IL4, CCR7, ICOS, CA125, TIMP1, and IL12P40 where said kit may be used in the diagnosis of IPF, and wherein, preferably, said aforelisted markers (MMP7, MMP1, MMP-8 and at least two, at least three, at least four, at least five, at least six, at least seven, at least eight, at least nine, or at least ten, or at least fifteen, or at least twenty, of IGFBP1, TNFRSF1A, TNFRSF1B, MMP2, MMP3, AGER, CXCL10, CCL11, CCL2, FAS, IL12B, IL1RA, S100A12, B2M, MPO, ICAM-1, TF, VWF, SPA, SPD, MUC1 (KL-6), SFTPD, ID1, MEG3, IL4, CCR7, ICOS, CA125, TIMP1, and IL12P40) constitute at least 30 percent, at least 40 percent, at least 50 percent, at least 60 percent, at least 70 percent, at least 80 percent or at least 90 percent of the total markers in the panel.

In another set of non-limiting embodiments, the present invention provides for a kit comprising a means for determining the plasma levels of one or more of MMP-7, DEFA-1, DEFA-2 DEFA-3, S100A12, CCNA2, and/or IL12P40, wherein said kit may be used to determine the progression of IPF. In a specific, non-limiting embodiment, said kit for determining progression of IPF does not contain means for determining the plasma levels of more than twenty, or more than fifty, or more than one hundred other markers.

In specific non-limiting embodiments said means for determining a plasma level comprises, for each molecule to be tested, a capture agent selected from the group consisting of an antibody, a portion of an antibody, a single chain antibody, a non-immunoglobulin receptor for the molecule, a peptide ligand for the molecule, and an oligonucleotide ligand for the molecule, where said capture agent may, in non-limiting embodiments, be bound to a solid support, which may be, but is not limited to, a bead.

In addition to comprising means for determining the levels of plasma markers indicative of a diagnosis of IPF or its progression, said kits may further comprise means for determining the levels of plasma markers which represent control values of molecules which are not associated with IPF, such as, among many examples, albumin, MMP12, and CRP.

In addition to said means for determining levels of markers and optionally control molecules, said kits may further comprise a reagent necessary or desirable for determining marker/control levels, for example, but not by way of limitation, a labeled secondary antibody, an enzyme, avidin or streptavidin, etc.

In addition to said means for determining levels of markers and optionally control molecules, said kits may further comprise a positive control sample, for example a lyophilized control sample which may be reconstituted to provide levels of markers as may occur in a subject with IPF. For example, such a positive control sample may, when reconstituted, comprise MMP7, MMP1, MMP8, IGFBP1 and/or TNFRSF1A at levels increased relative to normal plasma levels, and optionally AGER at a level decreased relative to its normal plasma level. In a non-limiting embodiment, the positive control sample may be a plasma sample from an IPF patient which has been frozen, lyophilized or otherwise preserved.

Additional markers which may be used in the diagnosis and/or a prognostic evaluation of IPF are set forth in the examples below, the disclosure of which is hereby incorporated into this Detailed Description of the Invention section by reference.

6. EXAMPLES

6.1 Example 1

6.1.1 Materials and Methods

Initial IPF Derivation Cohort:

This study included 74 patients with IPF evaluated at the University of Pittsburgh Medical Center. The diagnosis of IPF was established based on published criteria (*Am J Respir Crit Care Med* (2000); 161: 646-664), and surgical lung biopsy when clinically indicated (Katzenstein A L and Myers J L, *Am J Respir Crit Care Med* (1998); 157: 1301-1315). Clinical data were available through the Simmons Center database. Smoking status was defined as previously described (King T E Jr. et al., *Am J Respir Crit Care Med* (2001); 164: 1171-1181). Fifty-three control subjects were obtained from the pulmonary division sample collection core. Baseline demographic information is detailed in Table 2. The mean FVC % predicted of IPF patients was 61.9+20.8, and the mean DLCO % predicted was 42.1+17.4.

Chronic Obstructive Pulmonary Disease (COPD):

Plasma samples from 73 patients with COPD evaluated at the University of Pittsburgh were available for this study. Individuals were clinically stable at the time of examination, had tobacco exposure of at least 10 pack-years and had no clinical diagnosis of rheumatologic, infectious or other systemic inflammatory disease. Disease severity was measured using the GOLD classification as previously described (Pauwels R A et al., *Am J Respir Crit Care Med* (2001); 163: 1256-1276). The COPD cohort included 13 patients with GOLD class 0-I, 21 patients with GOLD II and 39 patients with GOLD Sarcoidosis:

Plasma samples from 47 patients with sarcoidosis evaluated at the University of Pittsburgh Medical Center were tested. Patients with lung disease (n=29) demonstrated an average FVC % predicted of 76.7±22.1, and average DLCO % predicted of 72.9±25.5. The diagnosis and staging of disease was determined according to American Thoracic Society and European Respiratory Society criteria, as described in Costabel U and Hunninghake G W, *Eur Respir J* (1999); 14: 735-737 and *Am J Respir Crit Care Med* (1999); 160: 736-755.

Hypersensitivity Pneumonitis (HP):

Plasma samples from 41 patients with subacute/chronic HP and 34 patients with IPF evaluated at Instituto Nacional de Enfermedades Respiratorias in Mexico were available for this study. Diagnosis of IPF and HP has been described for this cohort in Bustos M L et al., *Am J Respir Crit Care Med* (2007); 176: 90-95 and Selman M et al., *Am J Respir Crit Care Med* (2006); 173: 188-198. Briefly, HP patients showed the following features: a) antecedent bird exposure and positive plasma antibodies against avian antigens; b) clinical and functional features of ILD; c) HRCT showing diffuse centrilobular poorly defined micronodules, ground glass attenuation, focal air trapping and mild to moderate fibrotic changes and d) greater than 35% lymphocytes in bronchoalveolar lavage (BAL) fluid. Forty-four percent of the patients had a surgical lung biopsy; in all cases lung histology was consistent with the diagnosis of HP. The average FVC % predicted was 60.3±15.3 for HP and 59.1±17.2 for IPF patients.

Independent Validation Cohort:

Plasma samples from 20 control subjects, eight patients with sub-clinical idiopathic ILD, 16 patients with familial pulmonary fibrosis and nine with sporadic IPF, evaluated at the Warren Grant Magnussen Clinical Center of the National Institutes of Health (NIH), were available for this study. Patients with sub-clinical disease were first-degree relatives of patients with familial pulmonary fibrosis; they were asymptomatic, with normal pulmonary function tests but HRCT findings consistent with early ILD. The definition of familial pulmonary fibrosis was described in Steele M P et al. *Am J Respir Crit Care Med* (2005); 172: 1146-1152. Normal volunteers were used as controls.

Each of the above cohorts have been described in Ren P et al. *Am J Respir Crit Care Med* (2007); 175: 1151-1157 and Rosas I O et al. *Am J Respir Crit Care Med* (2007); 176: 698-705. Briefly, the mean FVC % predicted values for patients with sporadic IPF and familial pulmonary fibrosis were 59.4±19.7 and 75.7±16.7, respectively. Eight patients with familial pulmonary fibrosis were diagnosed with early asymptomatic ILD using HRCT (Rosas 10 et al. *Am J Respir Crit Care Med* (2007); 176: 698-705); the mean FVC % predicted in this group was 101.3±10.1. Gender, age, ethnic origin and smoking status for all groups are presented in Table 3.

Lung tissue samples for microarray analysis were obtained through the University of Pittsburgh Health Sciences Tissue Bank as described in Pardo A et al. PLoS Med (2005); 2(9): e251. Twenty-three samples were obtained from surgical remnants of biopsies or lungs explanted from patients with IPF who underwent pulmonary transplant and 14 control normal lung tissues obtained from the disease free margins with normal histology of lung cancer resection specimens. The morphologic diagnosis of IPF was based on typical microscopic findings consistent with usual interstitial pneumonia (Katzenstein A L and Myers J L, *Am J Respir Crit Care Med* (1998); 157: 1301-1315; *Am J Respir Crit Care Med* (2001); 165: 277-304). All patients fulfilled the diagnostic criteria for IPF outlined by the American Thoracic Society and European Respiratory Society (*Am J Respir Grit Care Med* (2000); 161: 646-664).

All studies were approved by the Institutional Review Board at the University of Pittsburgh, the National Heart, Lung, and Blood Institute or the National Institute of Respiratory Diseases, Mexico. Informed consent was obtained from all patients.

Blood Samples:

45 ml of blood was drawn from subjects using standardized phlebotomy procedures. Plasma or plasma was separated by centrifugation, and all specimens were immediately aliquoted and frozen.

Bronchoalveolar Lavage (BAL):

BAL was performed through flexible fiberoptic bronchoscopy as part of the diagnostic process, as described in Selman M et al. *Am J Respir Crit Care Med* (2006); 173: 188-198; Pardo A et al. *PLoS Med* (2005); 2(9): e251; Selman M et al. (2007) PLoS ONE; 2(5): e482. Supernatants were kept at −70° C. until use. BAL samples from 22 IPF patients (age 62.2+7.2 years) and 10 normal controls (age 41.5+5 years) were available for this study.

Multiplex Analysis:

Assays were performed using Luminex xMAP technology (Luminex Corp., Austin, Tex.) in 96-well microplate format according to appropriate manufacturers' protocols (Invitrogen, Camarillo, Calif., and R&D Systems, Minneapolis, Minn.), as described in Gorelik E et al. Cancer Epidemiol Biomarkers Prey (2005); 14: 981-987.

Bead-Based Immunoassays:

A 34-plex assay was performed for IL1A, IL1RA, IL1B, IL2, IL2R, IL4, IL5, IL6, IL7, IL8, IL10, IL12B, IL13, IL15, IL17, TNFA, IFNA, IFNG, GMCSF, EGF, VEGF, GCSF, FGF2, HGF, CXCL9, CXCL10, CCL2, CCL3, CCL4, CCL5, CCL11, TNFRS1A, TNFRS1B and TRAIL-R2 (Invitrogen). MMPs assays included MMP1, MMP2, MMP3, MMP7, MMP8, MMP9, MMP12, and MMP13 (R&D Systems).

Assays for FAS, EGFR, FASL, Cyfra 21-1 (CKRT19 fragment), IGFBP1, KLK10, were developed in the Pittsburgh Luminex Core Facility. The assays were validated as described in Gorelik E et al. Cancer Epidemiol Biomarkers Prev (2005); 14: 981-987.

ELISA:

Quantitative sandwich enzyme immunoassay for human MMP1, MMP7 and AGER was performed as recommended by the manufacturer (R&D Systems, Minneapolis, Minn.).

Oligonucleotide Microarray Experiments:

Briefly, total RNA was used as a template for synthesis of cDNA as recommended by the manufacturer of the arrays (Agilent Technologies, Santa Clara, Calif.). The cDNA was used as a template to generate Cy3 labeled cRNA that was used for hybridization on Agilent Whole Human Genome 4×44K multi pack arrays (Agilent Technologies, Santa Clara, Calif.). After hybridization, scanning and feature extraction, data files were imported into a microarray database and linked with updated gene annotations using SOURCE (http://genome-www5.stanford.edukgi-bin/SMD/source/source-Search) and then normalized using cyclic LOESS (Wu W et al. BMC Bioinformatics (2005); 6:309). Differentially expressed genes were identified using Significant Analysis of Microarrays (SAM) (Tusher V G et al., Proc Natl Acad Sci USA (2001); 98: 5116-5121. Probes corresponding to the 49 protein markers were identified through their gene symbols. Expression levels for the probes that corresponded to these markers were extracted. In the case of redundant probes, those with the highest expression level and with the lowest Q-value were selected for presentation.

Statistical Analysis:

A protein was considered differentially expressed when there was a change of at least 25% in concentration and statistical significance at p-value<0.05 corrected for multiple testing. Data were reported as mean±standard deviation. The Wilcoxon rank-sum test was used to identify potential biomarkers that univariately distinguish IPF samples from controls. For multiple testing the Bonferroni method was used to control the family-wise error rate at 5%. Data were analyzed using the R language for statistical computing (Ihaka R and Gentleman R, *Journal of Computational and Graphical Statistics* (1996); 5: 299-314; http://www.r-project.org). Classification and Regression Trees (CART) methodology was used to identify potential combinations of peripheral blood biomarkers that could be used to distinguish IPF from controls. CART was performed using the rpart package for recursive partitioning. Classification performance was assessed using the ROCR package (http://rocr.bioinf.mpi-sb.mpg.de). SAM was applied for oligonucleotide data analysis (Tusher V G et al., *Proc Natl Acad Sci USA* (2001); 98: 5116-5121). Data visualization and clustering were performed using Genomica (http://genomica.weizmann.acil/index.html) (Novershtern N et al., *Am J Respir Cell Mol Biol.* (2008); 38(3):324-36) and Spotfire Decision Site 9 (TIBCO, Palo-Alto, Calif.).

Entrez Gene IDs of Mentioned Proteins:

The Entrez Gene IDs for AGER, CCL11, CXCL10, IL12B, IGFBP1, MMP1, MMP3, MMP1, MMP8, MMP9, TNFRSF1A, and TNFRSF1B are 177, 6356, 3627, 3593, 3484, 4312, 4314, 4316, 4317, 5318, 7132, and 7133, respectively.

6.1.2 Results

Plasma Proteins Distinguished IPF Patients from Controls in Derivation Cohort:

Forty eight of 49 markers analyzed were detectable in plasma (FIG. 1A); univariate analysis identified 12 proteins that were differentially expressed in IPF compared to controls (Table 4). Five MMPs (MMP7, MMP1, MMP3, MMP8, MMP9), two chemokines (CXCL10, CCL11), FAS, IL12B, and the soluble TNF receptors (TNFRSF1A, TNFRSF1B) were found to be significantly over-expressed; AGER was found to be significantly under-expressed in plasma of patients with IPF compared to controls. MMP7 and MMP1, which have previously been shown to play a role in IPF pathogenesis, were the top-ranked proteins in univariate analysis (Table 4). Significant differences persisted when age, gender, or smoking status was statistically controlled.

To determine whether combinations of these plasma proteins correctly classify IPF patients, recursive partitioning was applied to the entire set of 49 markers and it was found that plasma protein profiles clearly distinguished IPF patients from normal controls. CART analysis showed that MMP7 and MMP1, in addition to being the two most significant biomarkers, are key components of a combinatorial classifier that also includes MMP8, IGFBP-1 and TNFRS1A (FIG. 1B). Sensitivity and specificity of the classifier were 98.6% (95% C.I. of 92.7% to 100%) and 98.1% (95% C.I. of 89.9% to 100%), respectively. High concentrations of MMP7 alone (>1.99 ng/ml) correctly classified 69 of 74 IPF patients (93.2%) but incorrectly classified five normal samples as IPF and five IPF samples as controls, whereas the combination of high plasma concentrations of both MMP7 (≥1.99 ng/ml) and MMP1 (≥2.15 ng/ml) excluded all controls. Thus the combination of high MMP7 and high MMP1 concentrations can distinguish IPF patients from controls. Receiver operating characteristic curves (ROCs) (FIG. 1C) has confirmed that MMP7 is the best univariate classifier although the combination of five markers performs somewhat better (FIG. 1C), as does the combination of MMP7 and MMP1.

MMP7 and MMP1 were Increased in the Lung and BAL Fluid of Patients with IPF:

To determine whether protein concentration differences in peripheral blood reflect gene expression differences present in the lung, gene expression patterns were analyzed in 23 IPF and 14 control lungs using oligonucleotide microarrays (FIG. 2A). Of the five plasma proteins in the CART plasma signature (FIG. 1B), only the genes for MMP7 and MMP1 were found to be significantly over-expressed in IPF lungs compared to controls (SAM Q value=0 for both genes; 7.3- and 15.7-fold increase, respectively). Of the 10 other proteins that were significantly different in the plasma of patients with IPF (Table 4), the genes for MMP3, AGER and IL12B were also significantly differentially expressed in IPF lungs (FIG. 2A).

To determine whether MMP7 and MMP1 proteins are secreted into the alveolar microenvironment, their concentrations were measured in bronchoalveolar lavage fluid (BAL) obtained from 22 patients with IPF and 10 control subjects. MMP7 and MMP1 BAL concentrations were observed to be significantly higher in IPF patients compared to controls ($p<0.00001$ and =0.018, respectively) (FIGS. 2B and 2C). Hence, elevated MMP7 and MMP 1 levels in the lung microenvironment are the most likely source for their increased concentrations in peripheral blood.

Figure 3A:
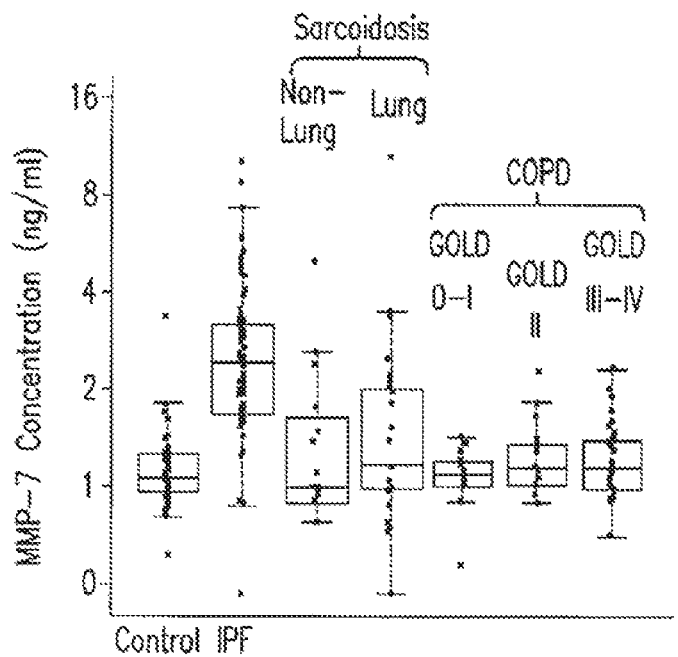
Figure 3B:
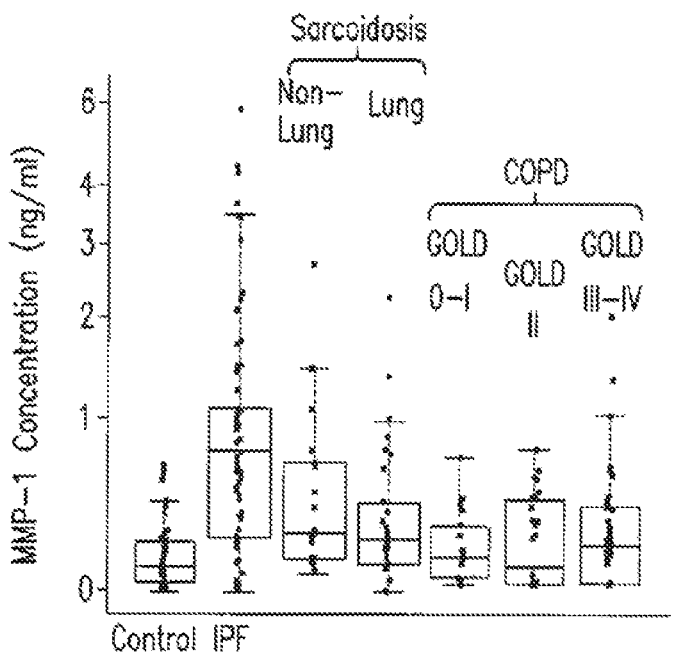

MMP7 and MMP1 were not Increased in Patients with COPD or Sarcoidosis:

To determine whether concentrations of MMP7 and MMP1 are increased in other common chronic lung diseases, plasma concentrations were measured in patients affected with sarcoidosis or COPD. The 47 sarcoidosis patients were stratified into those with evidence for parenchymal lung disease (stage 2 or greater; n=29) and those with no lung parenchymal involvement (n=18). As shown in FIG. 3A-B, no significant differences were found in plasma concentrations of MMP7 ($p=0.78$) (FIG. 3A) or MMP1 ($p=0.27$) (FIG. 3B) between the sarcoidosis groups with or without lung abnormalities when compared to controls. COPD subjects were grouped by GOLD class, into 0-I (n=13), II (n=21), and III-IV (n=39). No significant differences were found in plasma concentrations of MMP7 ($p=0.21$) or MMP1 ($p=0.85$) between groups of COPD patients stratified by GOLD class (FIGS. 3A-B, respectively).

Figure 4A:
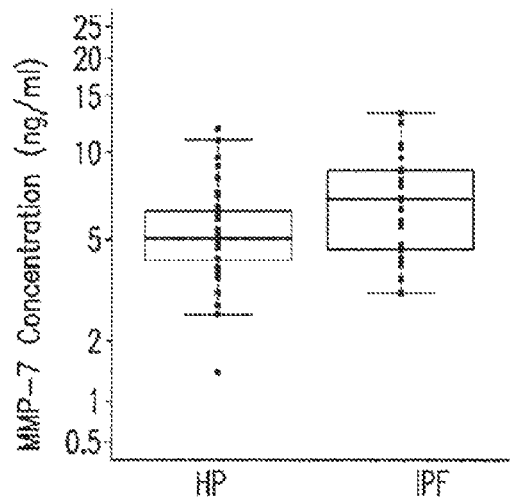
Figure 4B:
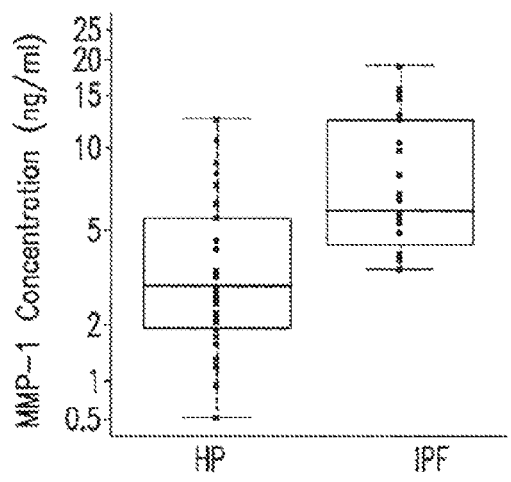

The Plasma Concentrations of MMP7 and MMP1 were Significantly Higher in Patients with IPF Compared to Patients with HP:

To determine whether peripheral blood concentrations of MMP7 and MMP1 distinguish IPF from other common forms of ILD, their levels were measured in 41 patients with HP and 34 patients with IPF. Univariately, plasma concentrations of MMP7 ($p=0.01$) and MMP1 ($p=<0.001$) were significantly higher in IPF compared to HP; fold changes for MMP1 and MMP7 were 2.3 and 1.31, respectively (FIGS. 4A and 4B).

Figure 4C:
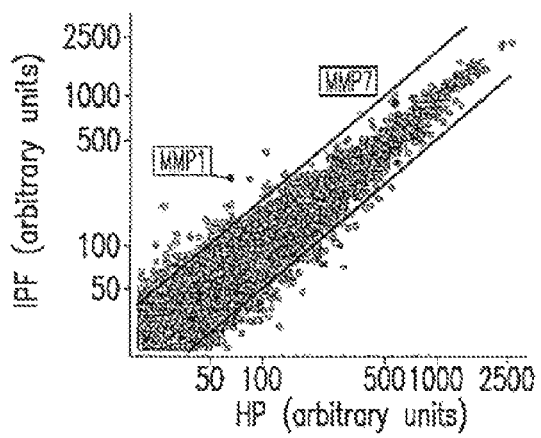

Similar results were observed in a re-analysis of a published DNA microarray dataset (Selman M et al., *Am J Respir Grit Care Med* (2006); 173: 188-198) comparing gene-expression in lung tissue obtained from IPF and HP patients. In this re-analysis, MMP7 and MMP1 levels were significantly higher in IPF compared to HP (FDR<5%), however, as observed in the peripheral blood, the change in MMP7 levels was moderate when compared to the increase in MMP1 (FIG. 4C).

Figure 4D:
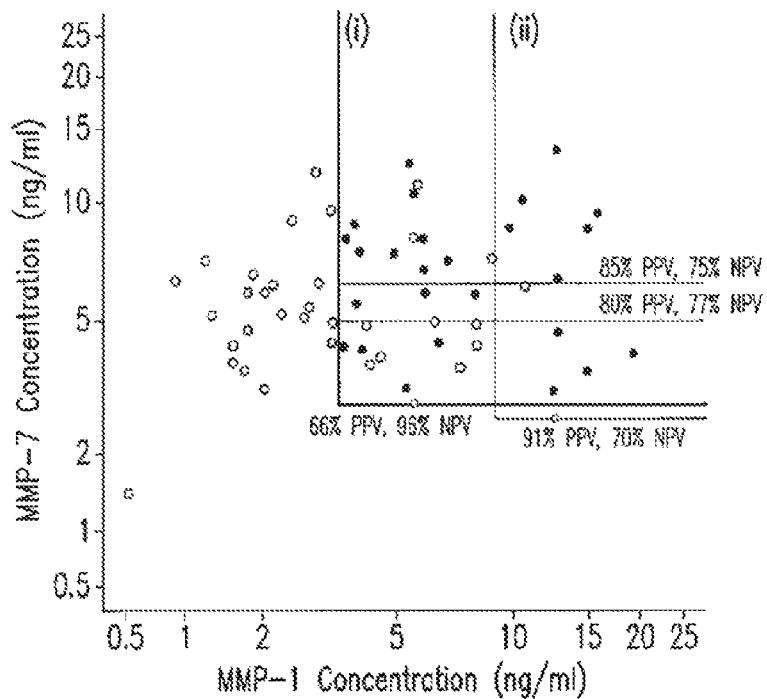
Figure 4E:
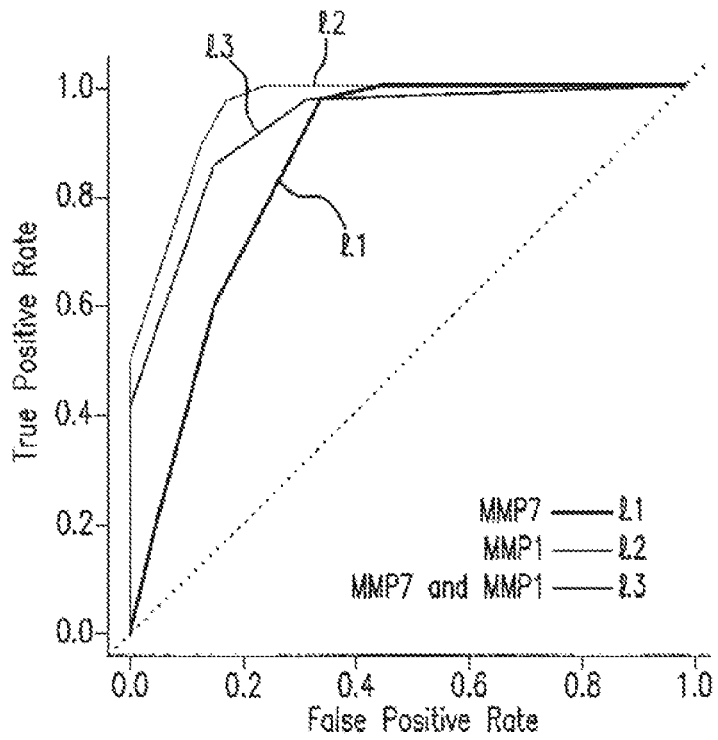

Combinations of plasma MMP1 and MMP7 concentrations had positive predictive values for determining that a patient had IPF ranging from 91% (MMP7>2.6 ng/ml and MMP1>8.9 ng/ml) to 66%, and negative predictive value (ruling out IPF) ranging from 96% (MMP7<2.9 ng/ml and MMP1>3.5 ng/ml) to 70% (FIG. 4D). Additionally, the combination of high MMP7 and high MMP1 peripheral blood concentrations distinguished IPF from HP with 96.3% sensitivity (95% C.I. of 81.0% to 100%) and 87.2% specificity (95% C.I. of 72.6% to 95.7%) (FIG. 4E), further supporting that MMP1 in combination with MMP7 distinguish IPF from HP.

The Plasma Concentrations of MMP7 and MMP1 were Significantly Higher in an Independent Validation Cohort:

To verify the above findings, plasma concentrations of MMP7 and MMP1 were measured in an independent validation cohort comprised of patients affected with IPF, familial pulmonary fibrosis or sub-clinical ILD, and control subjects. This cohort has been described in Rosas I O et al., *American Journal of Respiratory and Critical Care Medicine* (2007); 176:698-705. Even though concentrations were measured in plasma and not plasma, significantly higher concentrations of MMP7 and MMP1 were found in patients with pulmonary fibrosis compared to controls ($p<0.001$ and =0.01, respectively). Notably, plasma concentrations of MMP1 in patients with sub-clinical ILD were significantly higher compared to control subjects ($p=0.019$) and significantly lower compared to patients with full-blown IPF ($p<0.0001$) (FIG. 5A), suggesting that MMP7 may serve as a biomarker for disease progression. There was no significant difference in MMP7 concentrations between patients with familial or sporadic IPF, consistent with the findings of Yang et al (Yang I V et al., *Am J Respir Crit Care Med* (2007); 175: 45-54).

Figure 5A:
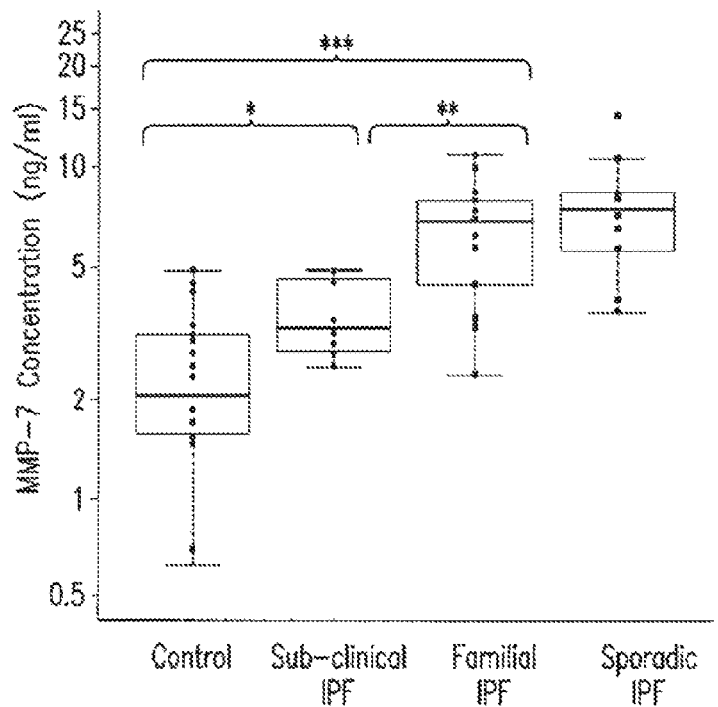
Figure 5B:
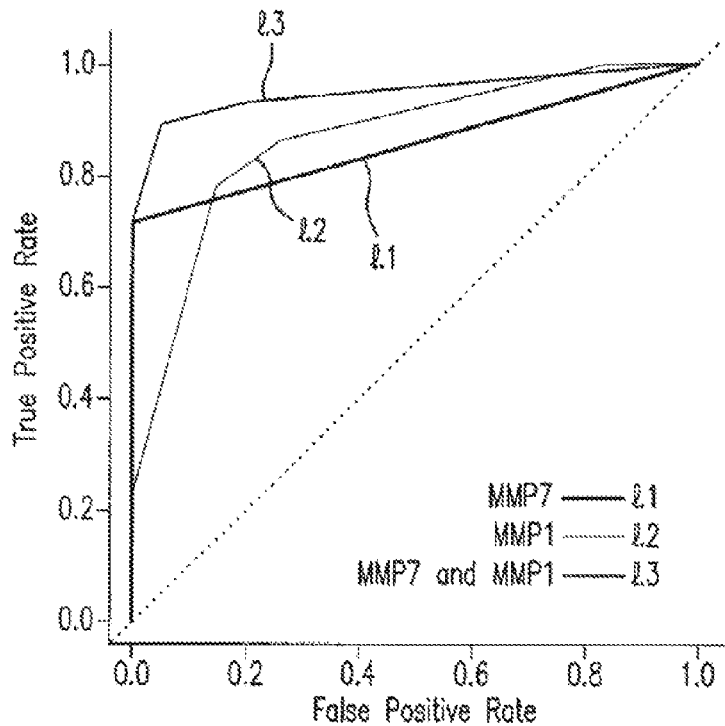
Figure 5C:
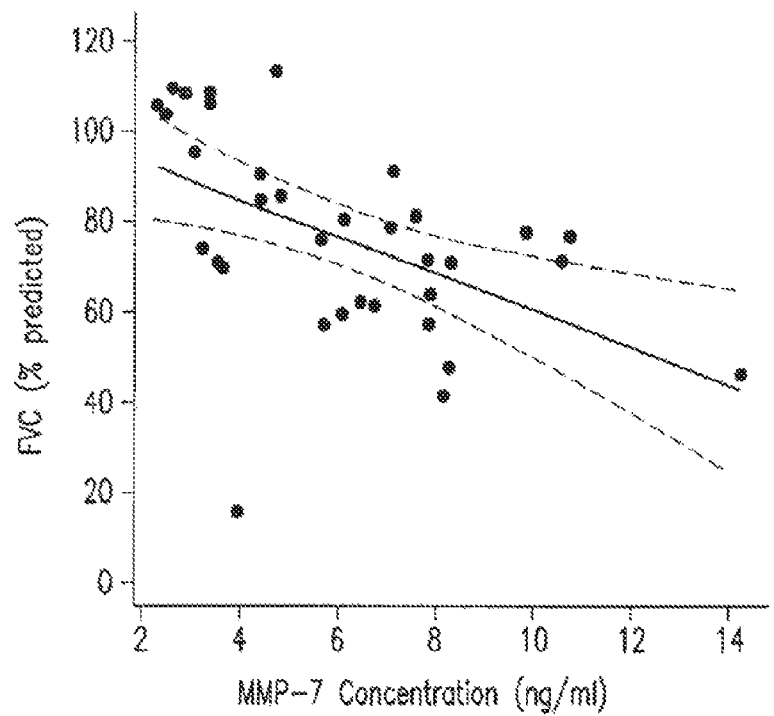

In this cohort elevated plasma concentrations of MMP1 combined with high plasma concentrations of MMP7, can distinguish IPF from controls with 89.2% sensitivity (95% C.I. of 71.8% to 91.7%) and 95.0% specificity (95% C.I. of 75.1% to 99.9%), supporting the findings in the derivation cohort (FIG. 5B).

Figure 5D:
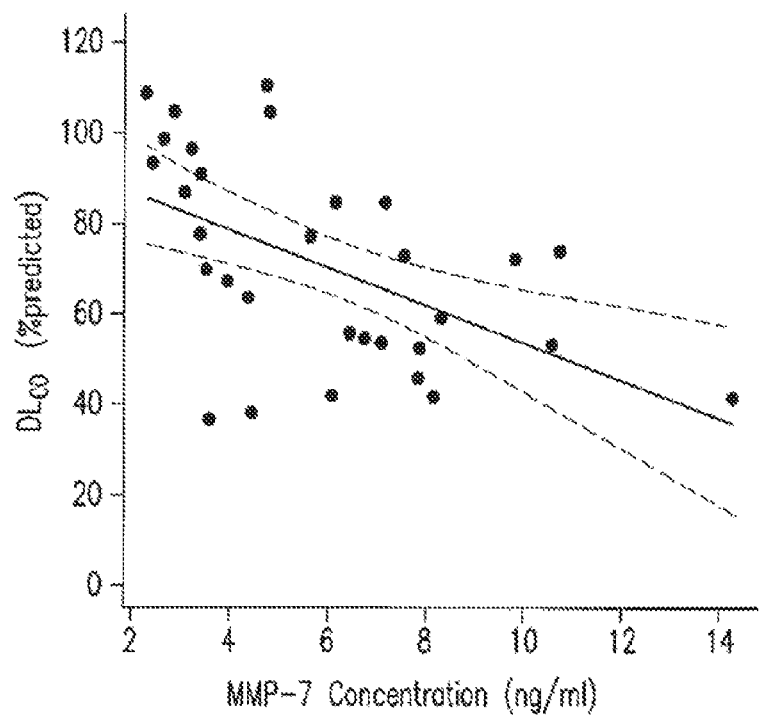

The Plasma Concentrations of MMP7 Correlated Moderately with Disease Severity:

To determine whether concentrations of MMP7 or MMP1 correlate with disease severity, pulmonary function measurements were compared with plasma concentrations of MMP7 and MMP1 in the validation cohort. A significant correlation was found between higher plasma concentrations of MMP7 and disease severity as measured by FVC % predicted (FIG. 5C) and DLCO % predicted (FIG. 5D). Fitted models predict a decline of 4.1% in DLCO % predicted ($p=0.002$, $r=-0.53$) and 4.0% in FVC % predicted ($p=0.002$, $r=-0.51$) for each increment of 1 ng/ml in plasma MMP7. No statistically significant correlation was found between MMP1 concentrations and pulmonary function measurements.

TABLE 2

Derivation Cohort Patient Characteristics

| | | IPF (N = 74) | Control (N = 53) |
|---|---|---|---|
| Sex | Male | 49 (66.2%) | 22 (41.5%) |
| | Female | 25 (33.8%) | 31 (58.5%) |
| Race | Caucasian | 73 (98.6%) | 47 (88.7%) |
| | African-American | 1 (1.4%) | 4 (7.5%) |
| | Unknown | 0 (0.0%) | 2 (3.8%) |

TABLE 2-continued

Derivation Cohort Patient Characteristics

|  |  | IPF (N = 74) | Control (N = 53) |
|---|---|---|---|
| Smoking | Current | 2 (2.7%) | 3 (5.7%) |
|  | Former | 56 (75.7%) | 22 (41.5%) |
|  | Never | 16 (21.6%) | 26 (49.1%) |
|  | Unknown | 0 (0.0%) | 2 (3.8%) |
| Age (yrs) | Mean ± SD | 65.9 ± 9.4 | 50.5 ± 15.7 |

TABLE 3

Validation Cohort Patient Characteristics

|  | Sporadic IPF (N = 9) | Control (N = 20) | Sub-clinical ILD (N = 8) | Familial IPF (N = 16) |
|---|---|---|---|---|
| Sex |  |  |  |  |
| Male | 2 (22%) | 9 (45%) | 6 (75%) | 7 (44%) |
| Female | 7 (78%) | 11 (55%) | 2 (25%) | 9 (56%) |
| Race |  |  |  |  |
| Caucasian | 7 (78%) | 15 (75%) | 7 (87%) | 15 (94%) |
| Hispanic | 0 (0%) | 1 (5%) | 1 (13%) | 1 (6%) |
| Asian | 2 (22%) | 1 (5%) | 0 (0%) | 0 (0%) |
| AA | 0 (0%) | 3 (15%) | 0 (0%) | 0 (0%) |
| Smoking |  |  |  |  |
| Current | 0 (0%) | 0 (0%) | 2 (24%) | 2 (18%) |
| Former | 3 (33%) | 6 (30%) | 1 (13%) | 6 (35%) |
| Never | 6 (67%) | 14 (70%) | 5 (63%) | 8 (47%) |
| Age (yrs) |  |  |  |  |
| Mean ± SD | 66 ± 8 | 39 ± 17 | 49 ± 11 | 64 ± 11 |

TABLE 4

Plasma proteins that distinguish IPF from controls

| Symbol | Fold | p-value |
|---|---|---|
| MMP1 | 4.6 | <0.000001 |
| MMP7 | 3.2 | <0.000001 |
| MMP8 | 2.6 | <0.000001 |
| CXCL10 | 2.3 | <0.000001 |
| MMP9 | 2 | <0.000001 |
| TNFRSF1A | 1.8 | <0.000001 |
| MMP3 | 1.8 | <0.000001 |
| AGER | 0.66 | <0.000001 |
| FAS | 1.7 | <0.001 |
| CCL11 | 1.7 | <0.001 |
| TNFRSF1B | 1.4 | <0.001 |
| IL12B | 1.3 | <0.001 |

6.1.3 Discussion

Overall, the first evidence for a peripheral blood protein signature in IPF patients has been demonstrated. MMP7 and MMP1, two matrix metalloproteases, previously implicated in the pathogenesis of IPF (Pardo A and Selman M, *Proc Am Thorac Soc* (2006); 3: 383-388) were significantly increased in plasma, BAL fluid and lung tissue of IPF patients suggesting that increased levels of MMP7 and MMP1 in the peripheral blood are indicative of the pathologic changes that characterize the IPF alveolar microenvironment. Used in combination, blood levels of MMP1 and MMP7 can distinguish IPF patients from diverse types of chronic lung disease including HP, a common interstitial pneumonia that can sometimes be indistinguishable from IPF (Perez-Padilla R et al. Am Rev Respir Dis (1993); 148: 49-53; Ohtani Y et al., Thorax (2005); 60: 665-671; Churg A et al., Am J Surg Pathol (2006); 30: 201-208). Increases in blood concentrations of MMP7 were observed in patients with sub-clinical familial pulmonary fibrosis and higher levels of MMP7 were associated with disease severity. Taken together these findings support the use of MMP1 and MMP7 as IPF biomarkers and suggest that their role in diagnosis, early detection and monitoring of disease progression should be further investigated.

Multiple MMPs are among the 12 proteins significantly increased in the blood of IPF patients. The roles of MMPs have been intensively studied and debated in IPF (Gadek J E et al., N Engl J Med (1979); 301: 737-742). While multiple and often contrasting roles have been proposed for MMPs in regulating abnormal epithelial response to injury, fibroblast proliferation, extracellular matrix accumulation and aberrant tissue remodeling, the consensus is that this family of matrix degrading enzymes is involved in disease pathogenesis (Pardo A and Selman M, *Proc Am Thorac Sac* (2006); 3: 383-388; Suga M et al., *Am J Respir Crit Care Med* (2000); 162: 1949-1956; Selman M et al., *Am J Physiol Lung Cell Mol Physiol* (2000); 279: L562-574; Fukuda Y et al., *Lab Invest* (1998); 78: 687-698; Zuo F et al., *Proc Natl Acad Sci USA* (2002); 99: 6292-6297; Pardo A et al., *Int J Biochem Cell Biol* (2008); 40(6-7):1141-55). Thus, it is noteworthy that the two top-ranked proteins, MMP7 and MMP1, are the MMPs known to be significantly over-expressed in the activated alveolar epithelium in IPF lungs. MMP1, a matrix metalloprotease that primarily degrades fibrillar collagen, is rarely expressed under normal conditions, but is highly over-expressed in reactive alveolar epithelial cells in IPF lungs (Zuo F et al., *Proc Natl Acad Sci USA* (2002); 99: 6292-6297). MMP7, a matrix metalloprotease with multiple local inflammatory regulatory roles (Li Q et al., *Cell* (2002); 111: 635-646; McGuire J K et al., *Am J Pathol* (2003); 162: 1831-1843), is also highly up-regulated in alveolar epithelial cells in IPF (Zuo F et al., *Proc Natl Acad Sci USA* (2002); 99: 6292-6297; Cosgrove P et al., Chest (2002); 121: 25S-26S). Furthermore, MMP7 knockout mice are relatively protected from bleomycin-induced fibrosis (Zuo F et al., *Proc Natl Acad Sci USA* (2002); 99: 6292-6297) suggesting that MMP7 may have a pro-fibrotic effect in IPF. Taken in the above context, the above results strongly suggest that activated epithelial cells in IPF lungs are the likely source of elevated peripheral blood concentrations of MMP1 and MMP7, thus supporting their use as biomarkers for disease detection and progression.

It has been shown that neither patients with COPD, a chronic progressive lung disease, nor patients with sarcoidosis, a chronic granulomatous ILD, expressed significantly increased peripheral blood concentrations of MMP7 or MMP1. Further, elevated peripheral blood concentrations of MMP1, in the presence of elevated concentrations of MMP7 distinguished IPF from HP. A similar trend in gene expression of MMP7 and MMP1 was found in the lungs of patients with IPF and HP also supporting the notion that the changes in peripheral blood concentrations of MMP7 and MMP1 are reflective of the lung gene environment and constitute a disease specific signal. This may be very important clinically, because sub-acute HP is frequently misdiagnosed as idiopathic nonspecific interstitial pneumonia (NSIP), and in its chronic advanced form HP can be undistinguishable from IPF (Perez-Padilla R et al., *Am Rev Respir Dis* (1993); 148: 49-53;

Ohtani Y et al., *Thorax* (2005); 60: 665-671; Churg A et al., *Am J Surg Pathol* (2006); 30: 201-208). In fact, recent studies have demonstrated that histopathologic and HRCT abnormalities observed in chronic HP often overlap with those of usual interstitial pneumonia (UIP), representing an important challenge to the differential diagnosis of these conditions (Perez-Padilla R et al., *Am Rev Respir Dis* (1993); 148: 49-53; Ohtani Y et al., *Thorax* (2005); 60: 665-671; Churg A et al., *Am J Surg Pathol* (2006); 30: 201-208). Thus, the elevated peripheral blood concentrations of MMP7 and MMP1 observed in IPF are not due to a systemic stress response to a chronic lung disease and distinguish COPD, sarcoidosis, and HP from IPF.

It is important to note that IPF was not compared to other idiopathic interstitial pneumonias such as NSIP, so that the usefulness of MMP7 and MMP1 in distinguishing IPF from these conditions is not evaluated in this example section. In fact, the finding of elevated MMP7 in patients with subclinical ILD may be indicative that this increase may be present in other idiopathic ILDs. Furthermore, gene expression patterns were found to be extremely similar in IPF and NSIP (Yang IV et al., Am J Respir Crit Care Med (2007); 175: 45-54; Rosas 10 and Kaminski N, Am J Respir Crit Care Med (2007); 175: 5-6) and BAL MMP7 levels were also recently found to be similar in patients with IPF and NSIP (Vuorinen K et al., Apmis (2007); 115: 969-975). The major limitation in these studies was the small number of cases with NSIP because of the significant rarity of isolated NSIP.

6.2. Example 2

Samples were collected for a cross-sectional study, and 199 patients with IPF were enrolled, including one American Indian, four African Americans, 62 females and 137 males. 73 of these 199 patients were enrolled before the planning phase of the project. For the longitudinal study 65 IPF patients (41 males and 24 females) were recruited. Of them 63 are Caucasian, one is African American and one is American Indian. Twenty-eight patients have currently more than three visits (follow up longer than a year) 14 patients two visits and 23 one visit. The average age of patients upon enrollment to the longitudinal study is 67.2 (+/−10), FVC % 71.5% (+/−17), DLCO % 48.5 (+/−18). So far eight patients have died and eight had a lung transplant. Of the patients who have more than three visits, 14 are currently stable as can be judged by no change in PFT or clinical presentation. Fourteen others experienced a decrease of 10% in PFTs (FIG. 6). These results suggest that as there is a high enough event rate to identify patterns that characterize disease deterioration. Samples were separated into plasma, plasma, PBMC, aliquoted and snap frozen. On the average there were 2 mL of plasma per blood draw, 6 mL of Plasma and two trizol aliquotes. RNA was extracted from 142 samples at a quality and level sufficient for microarray analysis (85% of samples yielded>1.5 microgram). A database was developed for sample allocation and tracking and for patient follow-up. A tablet PC application has been created to improve patient intake in the clinic. In addition, an early disease cohort was aliquoted and initially analyzed. Outcome was analyzed in a Simmons Center cohort. Greater than 120 microarrays of PBMC were analyzed considering more than 100 protein markers in cross sectional analysis of serum and plasma as well as 15 markers in longitudinal analysis.

Cross Sectional Analysis of Proteins in Plasma or Serum of Patients with IPF.

The concentrations of 49 proteins in the plasma of 74 patients with IPF and in the plasma of 53 control individuals were analyzed. A combinatorial signature of five proteins, MMP7, MMP1, MMP8, IGFBP1, and TNFRSF1A, was identified—that was sufficient to distinguish patients from controls with a sensitivity of 98.6% (95% confidence interval (C.I.) 92.7%-100%) and specificity of 98.1% (95% C.I. 89.9%-100%). Additional proteins which were significantly increased in plasma of IPF patients were MMP2, MMP3 and MMP8, CXCL10, CCL11, FAS, IL12B, and TNFRSF1B. Only one protein, AGER, was found to be significantly decreased in plasma of patients with IPF. Eight of the IPF patients were treated with prednisone, three with interferon-γ (TFN-γ), 16 with IFN-γ and Prednisone, and 47 were untreated at the time of sampling. Patients on IFN-γ had substantially higher levels of CXCL10, IGFBP1 and IFNG though only CXCL10 passed the Bonferroni criterion for multiple testing. No effect of prednisone treatment on plasma protein concentrations was observed.

The significant differences in plasma protein concentrations between IPF and controls persisted in a patient population controlled statistically for age, gender, and smoking status. Increases in levels of MMP1 and MMP7 were also observed in lung tissue and bronchoalveolar lavage fluid obtained from IPF patients. The plasma concentrations of MMP7 and MMP1 were not increased in patients with chronic obstructive pulmonary disease or sarcoidosis and distinguished IPF compared to subacute/chronic hypersensitivity pneumonitis, a disease that may mimic TPF, with a sensitivity of 96.3% (95% CI 81.0%-100%) and specificity of 87.2% (95% CI 72.6%-95.7%). These results were verified in an independent validation cohort composed of patients with IPF, familial pulmonary fibrosis, subclinical interstitial lung disease (ILD), as well as with control individuals (FIG. 5). The concentrations of MMP7 and MMP1 were significantly higher in IPF patients compared to controls in this cohort. Furthermore, the plasma concentrations of MMP7 were elevated in patients with subclinical ILD and negatively correlated with percent predicted forced vital capacity (FVC %) and percent predicted carbon monoxide diffusing capacity (DLCO %). These results provided the first evidence for a peripheral blood protein signature in IPF. The two main components of this signature, MMP7 and MMP1, were overexpressed in the lung microenvironment and distinguished IPF from other chronic lung diseases.

In order to identify additional markers, an additional panel of 83 markers (Rules By Medicine) was evaluated in 153 plasma samples from patients with IPF and 70 from controls. The initial 74 patients and 53 controls were included in this cohort. These markers overlapped in cytokines with previous markers but lacked MMPs and IGFBs. CCL2 and TNFRSF1B that showed up in the previous analysis were also higher in plasma of patients with IPF in this cohort. Additional molecules included S100A12, B2M, MPO, TF, ICAM-1, IL1RA. These results indicate the diagnostic utility of a plasma marker panel comprised of MMP7, MMP1, MMP8, IGFBP1, TNFRSF1A, TNFRSF1B, MMP2, MMP3, AGER, CXCL10, CCL11, CCL2, FAS, IL12B, IL1RA, S100A12, B2M, MPO, ICAM-1, TF, VWF, and the previously reported surfactant proteins (SPA and SPD) and MUC1 (KL-6).

Protein Signatures During Disease Progression:

Protein expression was analyzed in sera of 28 patients that had more than three visits (follow up longer than a year), of which 11 had four visits, five had five visits and four had six visits (two years follow-up). Two patients died. One had an acute exacerbation after the sixth visit. Fifteen proteins were analyzed (CCL2, CCL11, CXCL12, CXCL11, CXCL10, MMP1, MMP7, MMP8, IGFBP1, AGER, SPP1, SAA1, TGFB1, SPC, SPD). Ten controls were included in the analysis.

PBMC signatures were used to confirm the reproducibility of the results (FIG. 7). Interestingly, longitudinal analysis suggested that IGFBP1 was significantly increased with time in IPF patients regardless of disease progression (FIG. 8) while MMP7 was increased only when disease progressed.

PBMC Gene Expression Signatures During Disease Progression.

For PBMC gene expression, 25 patients were analyzed, 22 of whom had more than three visits. Only three patients had two visits. Two Patients died, one died from acute exacerbation. One patient was followed over the time and in the sixth visit developed an acute exacerbation. Twenty-four analysis arrays of control subjects were prepared. Agilent whole genome arrays were used. Gene expression patterns were found to be dramatically different between PBMC from IPF patients and controls (FIG. 9). To determine how gene expression patterns changed over time, the samples were analyzed without the controls. Cluster analysis was performed to identify gene expression patterns that corresponded with time and to identify clusters that were significantly enriched with functional gene annotations, using gene ontology annotation database. Significant enrichment was determined by Fisher Exact and corrected for multiple testing. This analysis indicated that genes increased in PBMC were enriched for developmental pathways, while genes decreased in PBMC were enriched with response to stimulus and immune function.

6.3 Example 3

Gene Expression Patterns of Peripheral Blood Mononuclear Cells in Patients with IPF Patients Diagnosed with IPF were enrolled in two independent cohorts. Table 5 describes the patient population. Blood and pulmonary function tests (FVC/DLCO) were obtained in each IPF patient and in healthy donors. Mononuclear cells were extracted by centrifugation, and RNA was processed by using the Trizol protocol (Invitrogen). Gene expression microarrays were performed on Oligo DNA microarray System from Agilent Technologies (Santa Clara, Calif.) in the samples from the University of Pittsburgh and with DNA Microarrays System from Affymetrix in the samples from the University of Chicago. Microarray data normalizations were performed by using Bioconductor package for R (www.r-project.org) and Scoregene (fgusheba.cs.huji.ac.il/software.htm). Statistically significant genes were identified by using R, SAM (www-stat.stanford.edut/~tibs/SAM/) and Spotfire (TIBCO Spotfire, Somerville, Mass.). Microarray significance was defined as FDR<5%. Analysis of the up-regulated (increased) genes was performed by using Ingenuity Pathway Analysis Software (Ingenuity Systems, Reedwood City, Calif.). qRT-PCR was performed to validate the microarray data and for a time course analysis of the biomarker candidates genes by using Taqman gene expression assays from Applied Biosystems (Foster City, Calif.). ddCT method was applied to calculate gene expression levels of qRT-PCR and significance was define as a p-value<0.05 by unpaired two tailed T-Test.

TABLE 5

Description of the study population used for the Microarrays and qRT-PCR validation

|  | IPF - University of Pittsburgh | IPF - University of Chicago |
| --- | --- | --- |
| Number of patients | 25 | 23 |
| Average of Age | 65.32 | 67.95 |
| Average FVC % | 66.29 (+/−13.9) | 64.39 (+/−12.61) |
| Average DLCO % | 45.68 (+/−13.36) | 45.08 (+/−16.48) |
| Deaths | 4 | 4 |
| Male/Female | 15/10 | 17/6 |

PBMC Gene Expression Patterns Distinguished IPF Patients from Controls from the University of Pittsburgh Cohort:

A comparison between 10 IPF patients and 10 controls from the U of Pittsburgh cohort showed a difference of 1019 genes with FDR<5%. If a fold change>2 is added, the difference is reduced to 318 genes including 162 up-regulated (increased) genes which were found to be over-expressed, and 156 down-regulated (decreased) genes which were found to be under-expressed in plasma of patients with IPF compared to controls. (FIG. 11). Furthermore, it was found that among these 318 genes, ID1, SFTPD and MEG3 were found to be significantly over-expressed, and CCR7 and IL4 were found to be significantly under-expressed (FIG. 12).

Figure 13:
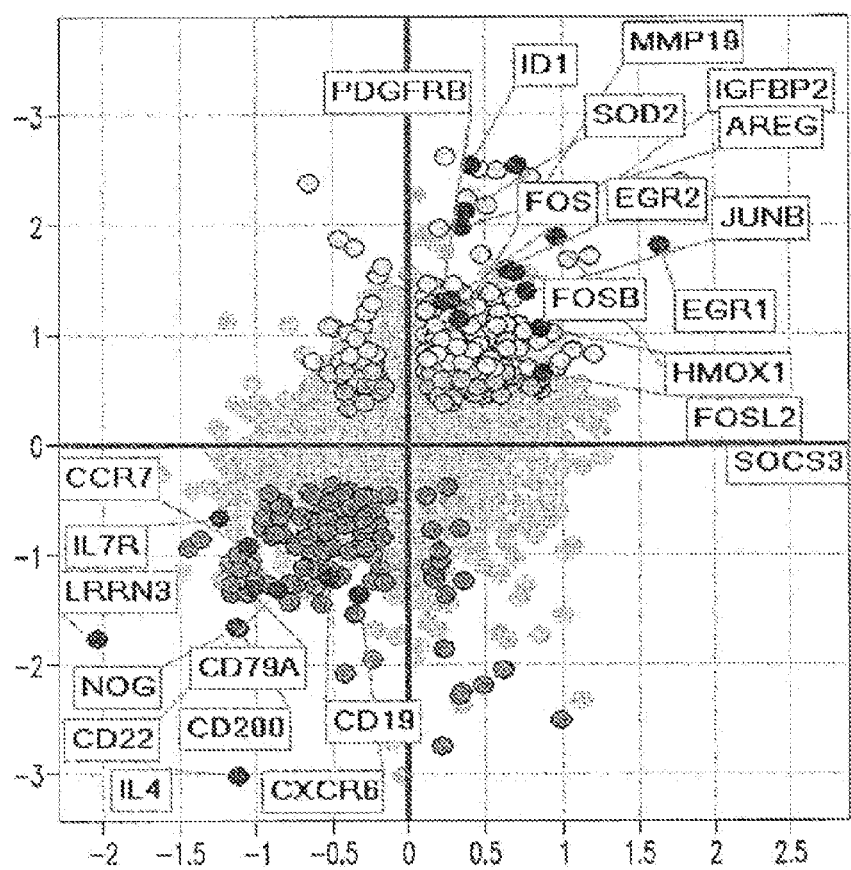

Gene Expression Between IPF University of Pittsburgh and University of Chicago Cohorts Showed Similar Patterns:

The commonly expressed genes between University of Pittsburgh and University of Chicago cohorts were compared as in FIG. 13. 14 genes: PDGFRB, FOS, FOSB, ID1, EGR1, EGR2, HMOX1, FOSL2, SOCS3, SOD2, MMP19, IGFBP2, AREG, and JUNB were the commonly over-expressed (up-regulated) genes, and 10 genes: CCR7, IL7R, LRRN3, NOG, CD22, IL4, CD200, CD79A, CD19 and CXCR6 were commonly under-expressed (down-regulated) genes in both University of Pittsburgh and University of Chicago cohorts.

Figure 14A:
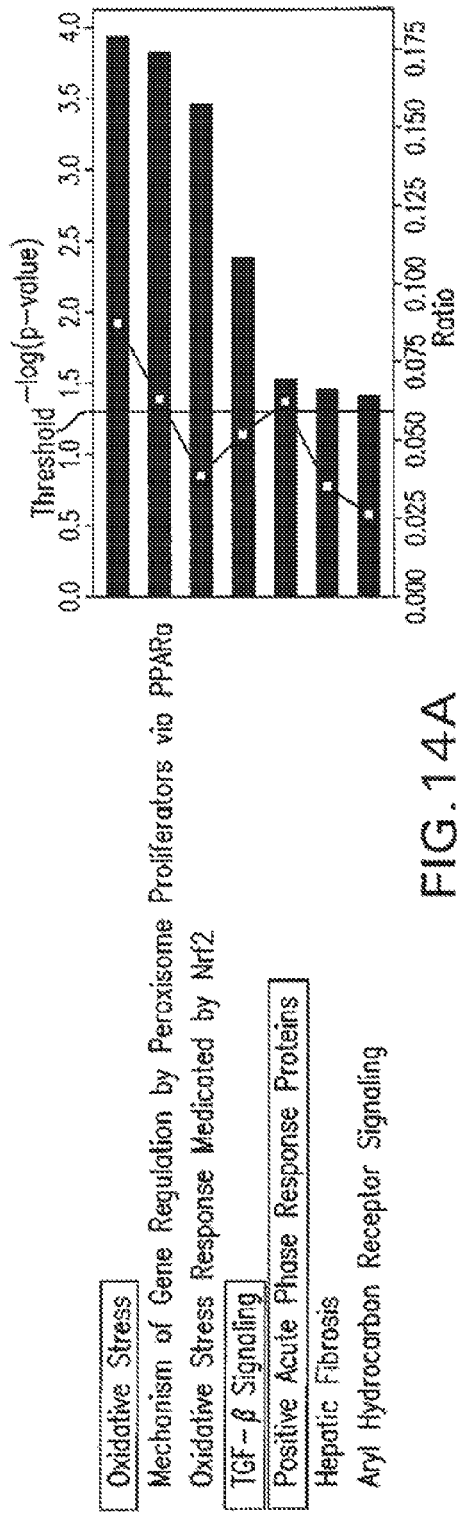
Figure 14B:
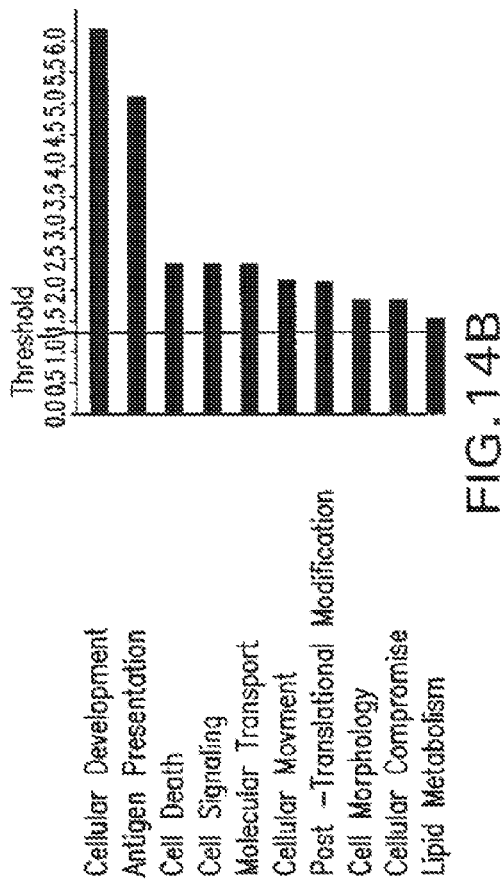

Protein Signature was Associated with Known Mechanisms of IPF:

A Tox list generated by Ingenuity of the top over-expressed (up-regulated) genes in IPF showed gene enrichment for known mechanisms involved in the disease such as the TGF-B signaling and oxidative stress pathways (FIG. 14A). These genes were also enriched with annotations related to cellular growth proliferation and morphology. The enrichment analysis of the top under-expressed (down-regulated) gene in IPF showed annotations related to cellular development, antigen presentation and cell death. The Ingenuity Tox list didn't show gene enrichment in these under-expressed (down-regulated) genes (FIG. 14B).

qRT-PCR Results Showed that SFPTD, ID1, and MEG3 were Significantly Increased in PBMC from Patients with IPF and IL-4, CCR7 and ICOS Were Significantly Decreased Compared to Controls:

qRT-PCR was performed to validate the microarray data in the two independent cohorts (FIG. 15). Validation was performed in commonly expressed genes in the two cohorts by microarray (ID1, IL4, CCR7, ICOS), and in the differentially expressed genes with probes unique to the Agilent microarray platform (SFTPD and MEG3). Similar values were found for all the validated genes in the two independent cohorts with statistically significant difference when compare to controls.

Time Course Analysis by qRT-PCR of SFTPD and IL-4 in 20 IPF Patients Showed Consistent Values:

A biomarker filter performed on the top over-expressed (up-regulated) and under-expressed (down-regulated) genes by Ingenuity showed SFTPD and IL-4 as candidate biomarkers in PBMC. 20 patients with IPF were followed during an period of 10 months with an average interval of five months between visits. qRT-PCR average showed consistent increase of SFTPD at each time point with statistically significant values when compare to controls, and the opposite phenomenon was found with the expression of IL-4 (FIG. 16).

Conclusion:

PBMC gene expression distinguished IPF from controls. There is an overall signal of reduced immune activity. The findings were corroborated in two independent cohorts of IFP patients from University of Pittsburgh and from University of Chicago. 1019 genes were significantly different (q<5). Genes increased in PBMC were enriched for annotations associated with oxidative stress, TGF-B signaling and positive acute phase response proteins. A decrease in B and T cell markers was found in the PBMC in IPF patients. SFPTD and IL4 were shown as candidate genes by a biomarker filter from Ingenuity. The qRT-PCR results showed that SFTPD, ID1 and MEG3 were significantly increased in PBMC from patients with IPF and Interleukin-4, CCR7, and ICOS were significantly decreased compared to controls. Increased levels of SFTPD in the serum of patients with IPF have been previously demonstrated and proposed as a possible biomarker at the protein level. The above studies demonstrates that there is also an over expression of SFTPD with consistent values across time at the mRNA level in PBMC, the opposed phenomenon happens with the expression of IL4.

6.4 Example 4

Gene Expression Profiles of Acute Exacerbations of IPF Methods

IRB:

The studies were approved by the Institutional Review Board at the University of Pittsburgh Medical Center (Pittsburgh, Pa., USA) and Asan Medical Center (Seoul, South Korea) as well as the Institutional local Committee for Oversight of Research Involving the Dead (CORID) of the University of Pittsburgh. Informed consent was obtained in all cases it was required.

Study Population:

Lung tissue samples for microarray analysis were obtained through the University of Pittsburgh Health Sciences Tissue Bank (Pittsburgh, Pa.) as described in Pardo A et al., *PLoS Med* 2005; 2:e251. Those included 23 lungs from patients whose clinical course did not suggest the occurrence of acute exacerbations (Demedts M et al., Eur Respir J (2002); 19:794-796) (stable IPF), 8 lungs from patients with acute exacerbation of IPF (IPF-AEx; obtained from explanted lungs or via the warm autopsy protocol) (Lindell K O et al., *PLoS Med* (2006); 3: e234; Akira M et al., *AJR Am J Roentgenol* (1997); 168:79-83; Collard H R et al., *Am J Respir Grit Care Med* (2007); 176:636-643), and normal lung histology samples from control subjects. The stable IPF samples were surgical remnants of biopsies or lungs explanted from patients with IPF undergoing pulmonary transplant, two IPF-AEx tissues were obtained from explanted lungs and six from the warm autopsy protocol (Lindell K O et al., *PLoS Med* (2006); 3: e234). Controls were normal histology tissues obtained from normal disease free margins of lung cancer resection specimens. The control lungs and stable IPF samples were the same samples as used in Rosas J O et al., *PLoS Med* (2008); 5:e93. The lung tissues were obtained from UPMC Tissue Bank. The tissues were snap frozen in liquid nitrogen, embedded in OCT polymer, or fixed in 5% formaldehyde then embedded in paraffin blocks. Plasma samples of patients with stable IPF (n=10), patients with IPF-AEx (n=16), and healthy control subjects (n=12) were obtained from Asan Medical Center (Seoul, South Korea). The diagnosis of IPF was based on the American Thoracic Society and European Respiratory Society definition (*Am J Respir Crit Care Med* (2000); 161: 646-664). The definition of IPF-AEx was based on criteria provided by Collard and colleagues (Collard H R et al., *Am J Respir Crit Care Med* (2007); 176:636-643) or Akira and colleagues (Akira M, et al., *AJR Am J Roentgenol* (1997); 168: 79-83). All cases were reviewed by expert pulmonologists and pathologists. Detailed clinical information about the subjects with IPF-AEx is provided in Tables 6 and 7.

The mean forced vital capacity (expressed as a percentage of the normal expected value) (FVC %) and diffusing capacity for carbon monoxide (expressed as a percentage of the normal expected value) (DLCO %) of patients with stable IPF and patients with IPF-AEx are provided in Tables 8A and 8B. All studies were approved by the Institutional Review Boards at the University of Pittsburgh and Asan Medical Center,

TABLE 6

Acute exacerbation cases from University of Pittsburgh

| Patient | Age | Gender | Race | Clinical | Pathology | Sampling method | FVC % | DLCO % |
|---------|-------|--------|-----------|----------|-----------|-----------------|-------|--------|
| AEx1 | 60-69 | F | caucasian | IPF | UIP + DAD | autopsy | 45.73 | 36.54 |
| AEx2 | 40-49 | M | caucasian | IPF | UIP + DAD | autopsy | 48.37 | 33.89 |
| AEx3 | 60-69 | M | caucasian | IPF | UIP + DAD | autopsy | 36.00 | 32.00 |
| AEx4 | 60-69 | M | caucasian | IPF | UIP + DAD | autopsy | 40.71 | 25.00 |
| AEx5 | 80-89 | F | caucasian | IPF | UIP + DAD | autopsy | 90.00 | na |
| AEx6 | 60-69 | M | caucasian | IPF | UIP + DAD | autopsy | 83.68 | 56.82 |
| AEx7 | 80-89 | M | caucasian | IPF | UIP + DAD | explant | 41.00 | na |
| AEx8 | 60-69 | M | caucasian | IPF | UIP + DAD | explant | 60.32 | 32.83 |

TABLE 7

Acute exacerbation cases from Asan medical Center

| patient | age | gender | race | biopsy confirmed | Initial CT UIP pattern | Initial FVC % | Initial DLCO % | CT*:AEx. | FVC %: AEx |
|---|---|---|---|---|---|---|---|---|---|
| AEx1 | 60-69 | M | asian | no | Typical | 78 | 83 | GGO:diffuse | |
| AEx2 | 70-79 | F | asian | no | Typical | 80 | 56 | GGO:subpleural | 61 |
| AEx3 | 70-79 | M | asian | yes | Atypical | 94 | 73 | GGO:diffuse | 54 |
| AEx4 | 60-69 | M | asian | no | Typical | 89.5 | na | GGO:subpleural | 59 |
| AEx5 | 70-79 | F | asian | no | Typical | 102 | 77 | GGO:multifocal | 66 |
| AEx6 | 50-59 | M | asian | yes | Atypical | 52 | 65 | GGO:diffuse | |
| AEx7 | 60-69 | M | asian | no | Typical | 63 | 60 | GGO:diffuse | |
| AEx8 | 80-89 | F | asian | no | Typical | 78 | 70 | GGO:multifocal | |
| AEx9 | 40-49 | F | asian | yes | Atypical | 66 | 62 | GGO:diffuse | 40 |
| AEx10 | 50-59 | M | asian | yes | Atypical | 47 | 47 | GGO:diffuse | |
| AEx11 | 60-69 | M | asian | yes | Atypical | 84 | 60 | GGO:multifocal | |
| AEx12 | 50-59 | F | asian | yes | Atypical | 51 | 33 | GGO:multifocal | |
| AEx13 | 70-79 | M | asian | no | Typical | 73 | 82 | GGO:multifocal | |
| AEx14 | 50-59 | M | asian | yes | Atypical | 73 | 66 | GGO:Subpleural | 54 |
| AEx15 | 70-79 | F | asian | yes | Atypical | 63 | 63 | GGO:diffuse | 51 |
| AEx16 | 70-79 | M | asian | no | Typical | 86 | 86 | GGO:diffuse | |

*GGO—ground glass opacities

TABLES 8A and 8B

Characteristics of patients with stable IPF and patients with acute exacerbation of IPF

| Variable | Stable IPF | IPF-AEx |
|---|---|---|
| A. Patients from University of Pittsburgh Medical Center | | |
| Number of subjects | 23 | 8 |
| Average age, yr | 61.71 (±5.51) | 68.25 (±10.22) |
| Average FVC % | 51.49 (±11.29) | 55.73 (±15.85)* |
| Average $D_{LCO}$ % | 40.26 (±16.19) | 36.61 (±12.06)* |
| Male/female | 19/4 | 6/2 |
| B. Patients from Asan Medical Center | | |
| Number of subjects | 10 | 16 |
| Average age, yr | 63.60 (±9.94) | 65.50 (±10.30) |
| Average FVC % | 81.1 (±11.97) | 55.0 (±8.3)† (n = 7) |
| Average $D_{LCO}$ % | 66.40 (±12.77) | 38.9 (±13.3)† (n = 7) |
| Male/female | 10/0 | 9/7 |

Definition of abbreviations: $D_{LCO}$ = diffusing capacity of carbon monoxide; IPF = idiopathic pulmonary fibrosis; IPF-AEx = acute exacerbation of idiopathic pulmonary fibrosis.
*Last before IPF-AEx.
†At the time of IPF-AEx.

Oligonucleotide Microarray Experiments:

Total RNA extracted from snap-frozen lung tissue was used as template for the generation of labeled cRNA that was hybridized to Agilent 4×44 k whole human genome microarrays and scanned with an Agilent scanner (Agilent Technologies, Santa Clara, Calif.) as recommended and previously described in Rosas, I. O. et al., PLoS Med (2008); 5, e93. The complete data set is available in the Gene Expression Omnibus database (http://www.ncbi.nlm.nih.gov/geo/; accession number GSE10667).

The details for extraction of total RNA from lung tissue are as follows: 25-50 µg of snap frozen lung tissue were homogenized in 1 mL of TRIZOL (15596-026, Invitrogen Corporation, Carlsbad, Calif.) with an electric homogenizer. Manufacturer's protocol for RNA isolation was followed in order to extract total RNA (Chomczynski P and Sacchi N, Analytical biochemistry (1987); 162:156-159). Extracted total RNA was then purified with RNeasy Mini spin columns (74104, Qiagen, Germantown, Md.) using the manufacturer's protocol for RNA cleanup. The yields and the quality of extracted RNA were assayed using NanoDrop and Bioanalyzer (Agilent Technologies, Santa Clara, Calif.).

Lung samples were lysed in ice cold Trizol (Invitrogen) and total RNA was extracted and used as a template for double stranded cDNA synthesis. RNA quantity was determined by NanoDrop at 260 nm and RNA integrity by Bioanalyzer (Agilent Technologies). Labeling was performed using the Agilent Low RNA Input Linear Amplification Kit PLUS, one color (5184-3523, Agilent Technologies). Briefly, first strand cDNA synthesis was performed using an oligo (dT)24 primer containing a T7 RNA polymerase promoter site. The cDNA was used as a template to generate Cy3 labeled cRNA that was used for hybridization. After purification and fragmentation aliquots of each sample were hybridized to Agilent Whole Human Genome 4×44K arrays (G4112F, Agilent Technologies). After hybridization, each array was sequentially washed and scanned by Agilent Microarray Scanner. Arrays were individually visually inspected for hybridization defects and quality control procedures were applied, as recommended by the manufacturer of the arrays. For array readout we used Agilent Feature Extraction 9.5.3 Software. Bioconductor for R was used to normalize the Processed Signal (Zhang J et al., Bioinformatics (Oxford, England) (2003); 19:155-156). Probes with annotations for Entrez Gene ID were extracted, and cyclic LOESS was applied to normalize the gene expression signals. In case of redundant probes we took the average over the values representing the gene expression levels. Differentially expressed genes were identified using Significant Analysis of Microarrays (14) (SAM) (http://www-stat.stanford.edu/~tibs/SAM). A q-value of 5 that corresponds to a false discovery rate (FDR) of 5% was set as the threshold for significance.

Blood Samples:

8 ml of blood was drawn from subjects using standardized phlebotomy procedures. Plasma or plasma was separated by centrifugation, and all specimens were immediately aliquoted and frozen at −80° C.

Antibodies:

The antibodies and the optimal dilutions used in this study were as follows; Rabbit polyclonal cyclin-A antibody raised against the C-terminal domain of CCNA2 was used at a dilution of 1:200 for immunofluorescence (IF), 1:1000 for western blots (ab 7956; Abcam™, Cambridge, Mass.). The following mouse monoclonal antibodies were used for IF at dilutions as described: Ki-67 nuclear antigen at a dilution of 1:200 (ab6526; Abcam), HNP 1-3 (α-defensins) at a dilution of 1:100 (HM2058; Hycult Biotechnologies, Uden, The Netherlands), cytokeratin (clone AE1/AE3) at a dilution of 1:100 (VP-C419; Vector Labs, Burlingame, Calif.) and vimentin (clone VIM 3B4) (VP-V683; Vector Labs) at a dilution of 1:100. Biotinylated secondary antibody against rabbit IgG, or mouse IgG were obtained (BA-1000 or BA-9200, Vector Labs) and was used at a dilution of L500 for IF. Mouse Monoclonal antibodies against beta-actin was obtained (P/N A2228; Sigma-Aidrich, St, Louis, Mo.) and used at a dilution of 1:3000 for western blots. HRP conjugated secondary antibody rabbit IgG, or mouse IgG were obtained (A0545, A9044; Sigma Aldrich) and used at a dilution of 1:10000 for western blots.

Real-time Quantitative Reverse Transcription-Polymerase Chain Reaction:

The same RNA samples used for microarray experiments were used to run real-time quantitative reverse transcription-polymerase chain reaction (qRT-PCR) on TaqMan system (Applied Biosystems, Foster City, Calif.). PCR was performed with TaqMan universal PCR master mix (Applied Biosystems) for the following genes: CCNA2, DEFA1-3, AGER, COL1A2, MMP1, MMP7, and GUSB. 1 µg of total RNA was primed with random hexamer and Superscript II (Invitrogen) was used to obtain first strand cDNA in each 20 uL reaction. PCR was performed with TaqMan Universal PCR Master Mix (P/N 4370048, Applied Biosystems) with the following inventoried forward and reverse primers/probes at optimized concentrations; CCNA2 (assay ID Hs00153138_m1), DEFA1-3 (Hs00414018_m1), AGER (Hs00153957_m1), MMP1 (Hs00233958_m1), MMP7 (Hs01042795_m1), COL1A2 (Hs01028970_m1) and GUSB (4333767F). Reactions were performed in a total volume of 10 µl and the PCR plates were run at University of Pittsburgh Genomics and Proteomics Core Laboratories. Conditions for the PCR were: 95° C. for 10 min followed by 40 cycles of 95° C. for 15 s and 60° C. for 1 min in the ABI 7900 real-time PCR system. The results were analyzed by the $\Delta\Delta C_t$ method and (GUSB, encoding β-glucuronidase) was used as a housekeeping gene. Fold change was calculated by taking the average over all the control samples as the baseline.

Immunohistochemistry:

OCT-embedded sections of normal and IPF-AEx samples were used for fluorescence immunohistochemistry. Rabbit polyclonal antibody against cyclin A2 (CCNA2; Abcam, Cambridge, Mass.), prosurfactant protein C (Abcam), and mouse monoclonal antibodies for cytokeratin (Vector Laboratories, Burlingame, Calif.), vimentin (Vector Laboratories), Ki-67 (Abcam), and α-defensins (Hycult Biotechnology, Uden, The Netherlands) were used. OCT embedded frozen tissues were subject to immunohistochemistry/confocal microscopy to study the histological properties of the following proteins; CCNA2, Ki67, prosurfactant protein C, α-defensins, cytokeratin. The sectioned tissues were fixed in ice-cold acetone for 15 minutes and air-dried, then rinsed in Tris-buffer-saline (TBS) twice for 5 minutes. Endogenous avidin and biotin were blocked using the Avidin/Biotin blocking kit (SP-2001; Vector Labs). Sections were incubated with avidin solution for 15 minutes, followed by another 15 minutes of incubation in the biotin solution. Non-specific binding blocking was performed by incubating sections for 20 minutes with TBS containing 5% normal goat plasma (NS). For labeling the first antigen, primary antibodies were diluted at optimal dilutions in 5% goat plasma/TBS and incubated at 4° C. overnight. The sections were then washed with TBS and incubated with secondary antibody for 30 minutes at room temperature. The sections were rinsed with TBS again, and labeled with FITC green. The labeling-visualization process was repeated for the second antigens and visualized with Texas Red. As a negative control, normal mouse or rabbit IgG were used instead of the primary antibodies. The sections were subjected to mounting and observation under Olympus Provis fluorescent microscope or Olympus Fluorview 1000 confocal microscope. Therefore, each antigen-antibody complex was labeled with biotinylated antibody against mouse or rabbit IgG, and visualized with fluorescein green or Texas red (Vector Laboratories). Nuclei were counterstained with 49,6-diamidino-2-phenylindole (Sigma-Aldrich, St. Louis, Mo.).

ELISA: Plasma concentrations of α-defensins were determined with an ELISA kit for α-defensins (DEFA1-3) (Hycult Biotechnology). Enzyme-Linked ImmunoSorbent Assay (ELISA) for human neutrophil peptides (HNP 1-3) was performed as recommended by the manufacturer (HK317; Hycult Biotechnology). Patient samples were prepared by diluting 1:3 in the plasma diluents provided with the kit. The HNP 1-3 standard was reconstituted as recommended by the manufacturer. Standards assembled on the plate ranged from 41 to 10000 pg/mL, with appropriate calibrator diluent. All samples and standards were run in duplicate and incubated for one hour at room temperature. Following four washes, Conjugate was added to each well and incubated. After one hour at room temperature, the reagents were aspirated and the plate was washed an additional four times. Shielded from light, the samples were incubated with substrate solution at room temperature for 30 minutes. After color development, the reaction was stopped and the optical density of the samples measured at 450 nm on a microplate reader.

Western Blot:

Total protein was denatured by adding Laemmli sample buffer (Bio-Rad, Hercules, Calif.) 2-mercaptoethanol and boiling. Fifteen micrograms of total protein was used in the immunoblotting process. Western blotting for CCNA2 was done as follows: 15 µg of total protein lysates were subject to 10% SDS-PAGE. Transfer was carried out at 300 mA for 90 minutes at 4 C in a buffer of Trizma base (3 g/L)-glycine (14.4 g/L)-methanol on PVDF membranes. Blots were blocked with 5% skim milk buffer in TBS-0.1% Tween20 (block buffer) for 1 hour at room temperature. Primary antibody was prepared at optimal dilution in block buffer and applied to the membranes at 4° C. overnight. Blots were rinsed with TBS-0.1% Tween20 for 5 minutes, 3 times, and incubated with HRP-conjugated secondary antibodies prepared in block buffer for 1 hour at room temperature. Blots were processed with Advance ECL (RPN2135, GE Amersham™, Piscataway, N.J.) for 3 minutes, and exposed to film for 1 to 10 minutes.

Terminal Deoxynucleotidyltransferase dUTP Nick End Labeling:

Formalin-fixed, paraffin-embedded tissue samples were used for the terminal deoxynucleotidyltransferase dUTP nick end labeling (TUNEL) assay, done with an in situ cell death detection kit (Roche Applied Sciences, Indianapolis, Ind.). After proteinase digestion the sections were incubated in a mixture containing terminal deoxynucleotidyltransferase and fluorescein isothiocyanate-labeled dUTP. The TUNEL conjugates were labeled with alkaline phosphatase, visualized with Vector red, and counterstained with hematoxylin. The samples were observed under a light microscope.

Statistical Analysis:

Array images were processed according to the Agilent Feature Extraction protocol (Zahurak M et al., *BMC Bioinformatics* (2007); 8:142). All arrays were cyclic-LOESS normalized, using the Bioconductor package as described in Wu W et al., BMC Bioinformatics (2005); 6: 309. For statistical analysis, significance analysis of microarrays (SAM) was applied (Segal E et al., *Nat Genet* (2005); 37:S38-S45). A q value of 5, which corresponds to a 5% false discovery rate, was used as a cutoff of statistical significance in microarray data. Data visualization and clustering were performed with Genomica (Segal E et al., *Nat Genet* (2005); 37:S38-S45), Scoregene (Dave NB and Kaminski N, Methods Mol Med (2005); 117:333-358), and Spotfire DecisionSite 9 (TIBCO, Palo Alto, Calif.). For qRT-PCR, the Student t test was used and significance was defined as P<0.05.

Results

Global Gene Expression Patterns of IPF-AEx and IPF were Similar Compared with Control Samples:

When compared with control samples, the global gene expression patterns of IPF-AEx were almost identical to those of stable IPF (FIG. 17A). To better characterize this similarity, genes that characterized IPF lungs (FIG. 17B) were studied and compared their expression in IPF-AEx with that in stable IPF (FIG. 17C). Impressively, all the highlighted genes were not significantly different between IPF and IPF-AEx (FIG. 17C; see also Table 9). These results indicate that compared with control samples, IPF-AEx exhibits a fibrosis signature that is identical to that of stable IPF.

TABLE 9

Genes that distinguish stable IPF from control samples did not significantly distinguish IPF from acute exacerbation of IPF

| Probe ID | Gene Symbol | q Value Stable IPF/ Control | q Value IPF-AEx/ Stable | Direction Stable IPF/ Control | Direction IPF-AEx/ Stable |
| --- | --- | --- | --- | --- | --- |
| A_23_P2492 | C1S | 0 | 50.81235685 | Up | Up |
| A_23_P119943 | IGFBP2 | 0 | 65.54015605 | Up | Up |
| A_23_P100660 | SERPINF1 | 0 | 51.91200838 | Up | Up |
| A_23_P142533 | COL3A1 | 0 | 76.39075568 | Up | Down |
| A_23_P207520 | COL1A1 | 0 | 63.33144534 | Up | Down |
| A_23_P52761 | MMP7 | 0 | 22.96815416 | Up | Down |
| A_23_P27133 | KRT15 | 0 | 42.91521282 | Up | Down |
| A_23_P201706 | S100A2 | 0 | 68.1759329 | Up | Up |
| A_23_P213745 | CXCL14 | 0 | 11.47868805 | Up | Down |
| A_23_P7313 | SPP1 | 0 | 75.66331514 | Up | Up |
| A_23_P1691 | MMP1 | 0 | 63.33144534 | Up | Down |
| A_23_P108062 | LGALS7 | 0 | 70.79949555 | Up | Down |
| A_23_P218047 | KRT5 | 0 | 74.65137647 | Up | Down |
| A_23_P85209 | IL13RA2 | 0 | 4.219172327 | Up | Down |
| A_23_P13907 | IGF1 | 0 | 61.75314131 | Up | Down |
| A_23_P501010 | COL17A1 | 0 | 15.70941508 | Up | Down |
| A_23_P87653 | KRT6A | 0 | 61.75314131 | Up | Up |
| A_23_P13094 | MMP10 | 0 | 55.98632176 | Up | Up |
| A_23_P153571 | IGFL2 | 0 | 7.018853253 | Up | Down |
| A_23_P93360 | AGER | 0 | 42.91521282 | Down | Down |
| A_24_P12626 | CAV1 | 0 | 24.69547444 | Down | Down |
| A_23_P70398 | VEGFA | 0 | 31.68574174 | Down | Down |

To confirm this observation, qRT-PCR was performed for MMP1, MMP7, COL1A2, and AGER, which are among the genes that consistently distinguish patients with IPF from control subjects (Rosas, I O et al. *PLoS Med* (2008); 5, e93; Zuo F et al., *Proc Natl Acad Sci USA* (2002); 99: 6292-6297) (FIG. 18A-D). As expected, COL1A2, MMP1, and MMP7 were significantly higher and AGER was significantly lower in IPF and IPF-AEx compared with control samples, but there was no significant difference in their expression between IPF and IPF-AEx.

Figures 19A, 19B:
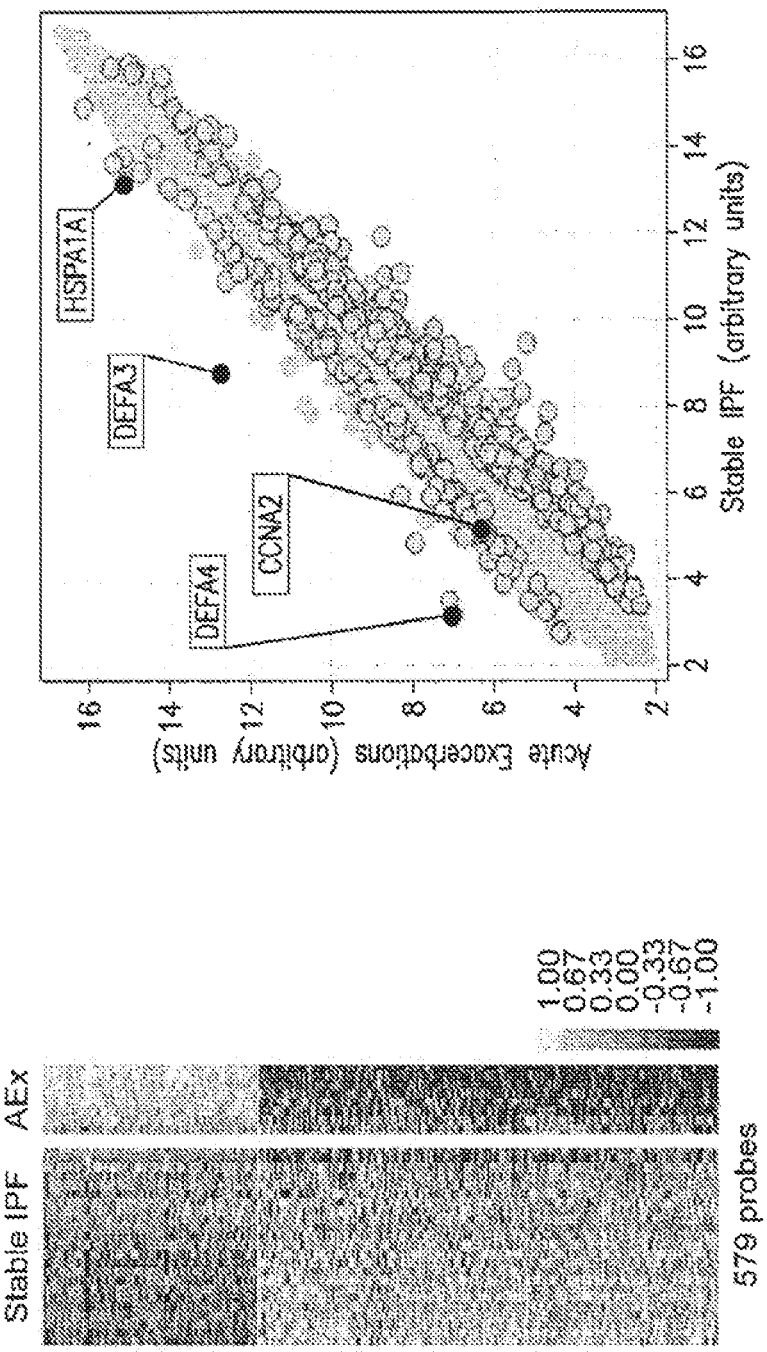
Figure 19C:
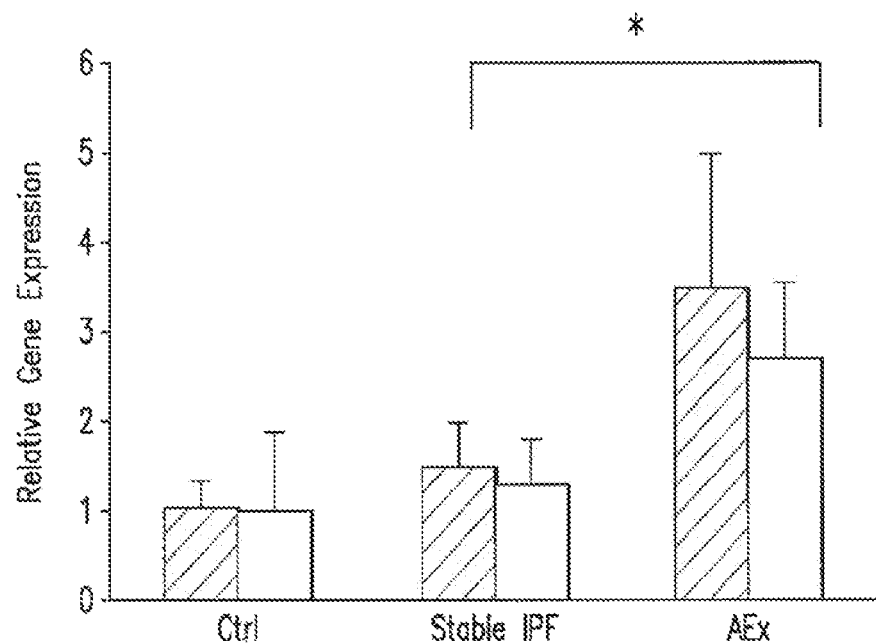

Direct Comparison of IPF-AEx and Stable IPF:

To identify the subtler gene expression changes that distinguish IPF-AEx from stable IPF, and to focus on clusters of genes that seemed differentially expressed in IPF and IPF-AEx (rectangles with double asterisks (**); FIG. 17A), a direct comparison of IPF-AEx and stable IPF was performed. 579 significantly differentially expressed genes (q<5) were identified (FIG. 19A). Among them were genes related to stress response such as heat shock proteins and α-defensins and mitosis-related genes including histones and CCNA2 (FIG. 19B and Table 10).

TABLE 10

Top 20 up-regulated probes that distinguish IPF-AEx from stable IFF

| Probe ID | Gene Symbol | q Value IPF-AEx/ Stable | Fold Ratio AEx/Stable |
| --- | --- | --- | --- |
| A_23_P31816 | DEFA3 | 0 | 15.452 |
| A_23_P326080 | DEFA4 | 0 | 13.436 |
| A_23_P219045 | HIST1H3D | 0 | 5.0072 |
| A_32_P221799 | HIST1H2AM | 0 | 4.1309 |
| A_23_P20022 | HIG2 | 0 | 3.3581 |
| A_23_P74059 | NPPA | 0 | 3.3542 |
| A_24_P123616 | HSPA1A | 0 | 3.3534 |
| A_23_P93258 | HIST1H3B | 0 | 3.0033 |

TABLE 10-continued

Top 20 up-regulated probes that distinguish IPF-AEx from stable IFF

| Probe ID | Gene Symbol | q Value IPF-AEx/ Stable | Fold Ratio AEx/Stable |
| --- | --- | --- | --- |
| A_23_P329593 | SEC24A | 0 | 2.604 |
| A_24_P933565 | PGAP1 | 0 | 2.4868 |
| A_23_P431734 | SLC25A37 | 0 | 2.4823 |
| A_23_P368740 | HDAC10 | 0 | 2.4006 |
| A_23_P381431 | NPL | 0 | 2.3955 |
| A_23_P3643 | DNASE1L2 | 0 | 2.3867 |

TABLE 10-continued

Top 20 up-regulated probes that distinguish
IPF-AEx from stable IFF

| Probe ID | Gene Symbol | q Value IPF-AEx/ Stable | Fold Ratio AEx/Stable |
|---|---|---|---|
| A_23_P48803 | TMOD2 | 0 | 2.3068 |
| A_23_P428184 | HIST1H2AD | 0 | 2.3003 |
| A_23_P111132 | HSPA1A | 0 | 2.29 |
| A_23_P58321 | CCNA2 | 0 | 2.271 |
| A_23_P333484 | HIST1H3H | 0 | 2.1118 |
| A_23_P30799 | HIST1H3F | 0 | 2.0654 |

Impressively, the gene expression signature of IPF-AEx did not exhibit an increase in inflammatory response compared with stable IPF. Genes known to be associated with the general inflammatory response, adaptive or innate immunity, were not significantly enriched in genes that characterize IPF-AEx (see FIG. 20). Similarly, only two (the α-defensins DEFA3 and DEFA4) of the 100 genes on the array that belong to gene ontology (GO) annotations associated with response to viral infection were significantly changed (see FIG. 21).

Figure 19D:
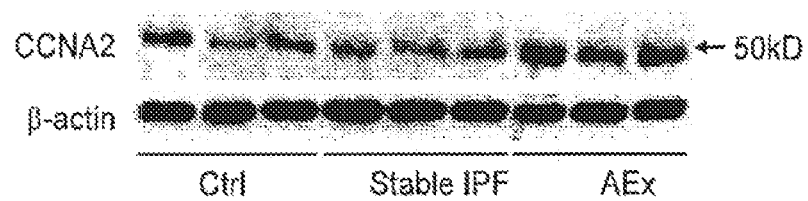
Figure 22A:
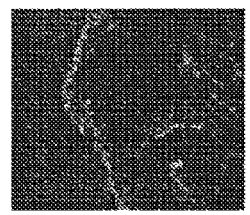
Figure 22B:
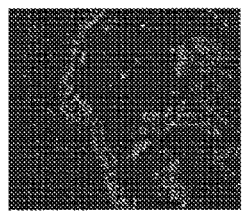
Figure 22C:
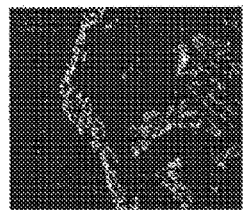
Figure 22D:
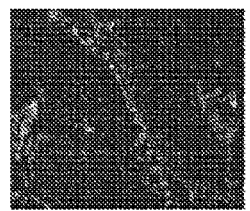
Figure 22E:
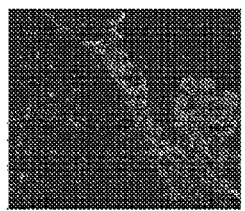
Figure 22F:
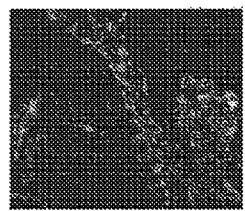
Figure 22G:
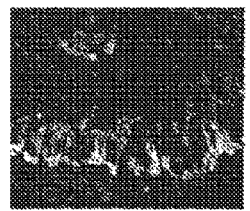
Figure 22H:
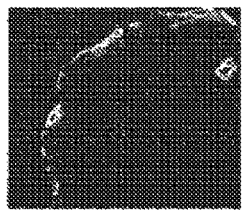
Figure 22I:
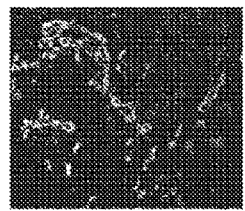

CCNA2 was Over-Expressed in IPF-AEx:

When compared with stable IPF, CCNA2 was one of the top 20 up-regulated genes, with a q value of 0 and a 2.27-fold increase (Table 10). Since this gene is a regulator of the cell cycle, its expression was validated and localized. qRT-PCR confirmed the microarray data (FIGS. 19B and 19C), and Western blots indicated an increase in CCNA2 protein (FIG. 19D). To localize CCNA2 over-expression, double-fluorescence labeling for CCNA2 with either cytokeratin or vimentin was performed. The double labeling demonstrated co-expression of CCNA2 with cytokeratin (FIGS. 22A-C), but not with vimentin (FIGS. 22D-F), indicating that the increase in CCNA2 was localized to epithelial cells and not fibroblasts. Confocal microscopy revealed localization of CCNA2 in the alveolar epithelium as well as the basal portion of the bronchial epithelium (FIGS. 22G-H). To determine whether increases in CCNA2 were associated with cellular proliferation, IPF-AEx tissues were double-labeled with CCNA2 and Ki-67. CCNA2 and Ki-67 co-localized to the pulmonary epithelium (FIG. 22I), suggesting accelerated epithelial cell proliferation, potentially as a compensatory response of the injured epithelium.

Figure 22J:
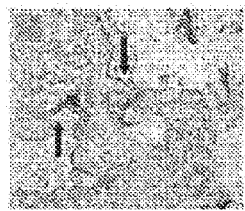
Figure 22K:
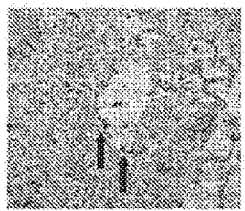
Figure 22L:
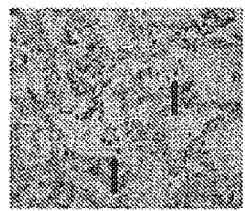
Figure 23A:
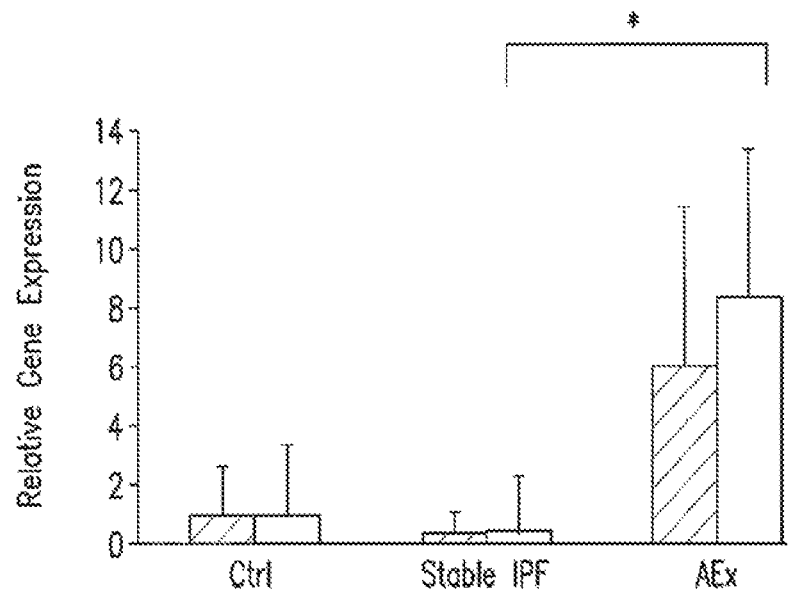
Figure 23B:
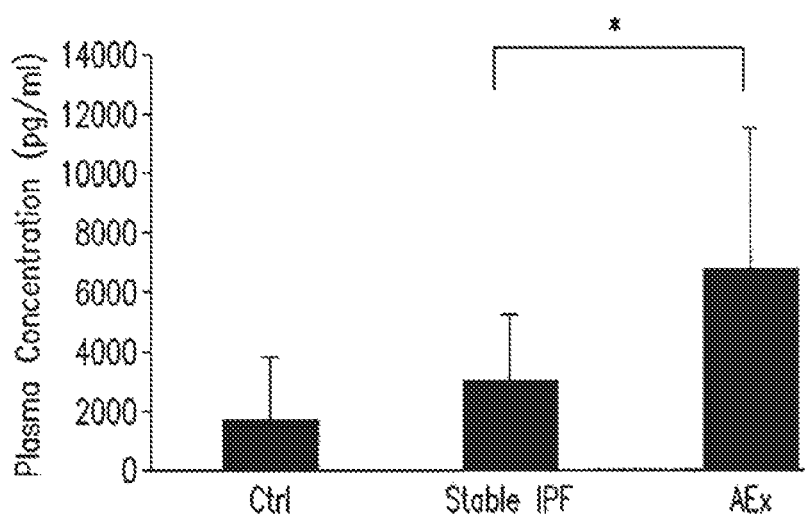
Figure 23C:
Figure 23D:
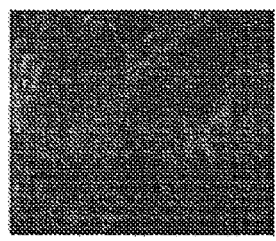
Figure 23E:
Figure 23F:
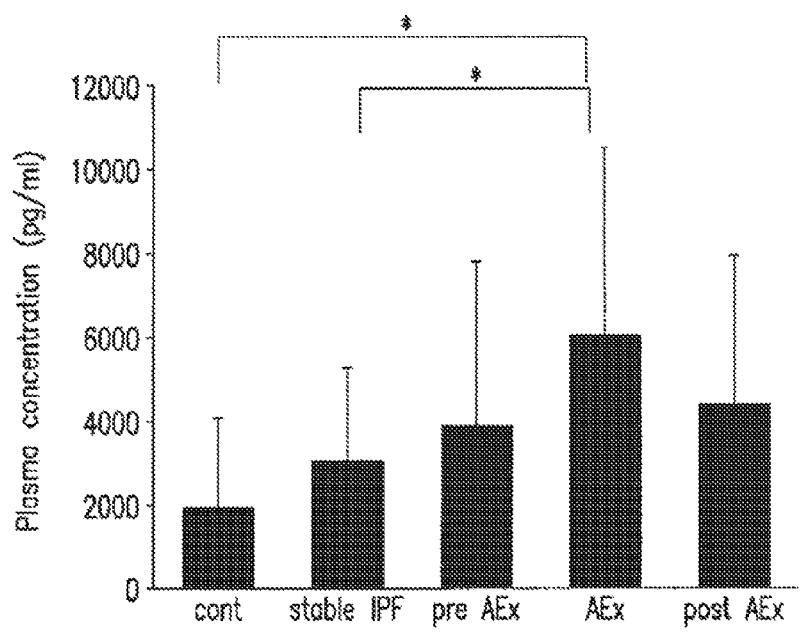

IPF-AEx Lungs Exhibited Widespread Epithelial Apoptosis:

To determine whether increased epithelial proliferation was associated with epithelial cell death in IPF-AEx, apoptosis in IPF-AEx tissues was studied by in situ TUNEL assay. It was observed that significant and widespread positive epithelial TUNEL staining in IPF-AEx tissues (FIG. 22K). This pattern was consistent with previous observations in IPF (Plataki M et al., Chest (2005); 127:266-274). In addition, positive TUNEL stains were also observed in the hyaline membranes typical of diffuse alveolar damage, a pathological hallmark of IPF-AEx (FIG. 22J). In control lungs, rare TUNEL-positive structures were predominantly observed in apoptotic bodies engulfed by alveolar macrophages (FIG. 22L).

α-Defensin Expression is Increased in Lungs and Peripheral Blood of Patients with IPF-AEx:

Gene expression of α-defensins (DEFA3 and DEFA4) was significantly increased in IPF-AEx lungs compared with stable IPF in the microarray data (FIG. 19B), and the increase was confirmed by qRT-PCR (FIG. 23A). To determine whether α-defensins may serve as peripheral blood markers for IPF-AEx, their levels in the plasma of patients with IPF-AEx from Asan Medical Center were analyzed. Plasma concentration of α-defensin were significantly higher in patients with IPF-AEx compared with control subjects (P=0.0007) or patients with stable IPF (P=0.025) (FIG. 23B). The plasma concentration of α-defensins in the controls, IPF, IPF-AEx were 1916.46 (+/−2163.93), 2541.91 (+/−2334.86), 6002.50 (+/−4579.46) pg/mL. The plasma concentrations of α-defensins were also shown the tendency to elevate in pre- and post-acute exacerbations group compared to the stable IPF (FIG. 23F). To determine the cellular origins of α-defensins in IPF-AEx, double labeling on IPF-AEx lung sections with antibodies against α-defensins and against the alveolar type II cell marker surfactant protein C(SFTPC) was performed. These experiments identified alveolar type II cells as the source of α-defensins in IPF-AEx (FIGS. 23C-E).

Discussion

In this study, gene expression microarrays were used to characterize acute exacerbations of IPF. Compared with control samples, IPF and IPF-AEx lungs exhibited similar gene expression signatures. However, on direct comparison of IPF and IPF-AEx, differentially expressed genes were identified and validation on CCNA2 and α-defensins was performed. CCNA2, a general regulator of the cell cycle, was among the most up-regulated genes in IPF-AEx. Increased CCNA2 protein expression was localized to proliferating epithelial cells but not to mesenchymal cells. TUNEL staining was also positive and localized to the epithelium in IPF-AEx. Gene expression levels of α-defensins were up-regulated in IPF-AEx and their protein expression was localized to the alveolar epithelium in IPF-AEx. Plasma α-defensin concentrations were higher in patients with IPF-AEx compared with those with stable IPF or control subjects. Taken together, these results indicate the central role of the pulmonary epithelium in IPF-AEx and suggest a potential role for α-defensins as peripheral blood biomarkers in IPF-AEx.

It is impressive to observe the relative similarity of the gene expression patterns that distinguish IPF or IPF-AEx from control lungs. It has been reported the up-regulation of matrix metalloproteinase-7 (MMP1), matrix metalloproteinase-1 (MMP1), collagens I and III, and osteopontin (Cosgrove G P et al., Am J Respir Crit Care Med (2004); 170:242-251; Pardo A et al., PLoS Med (2005); 2:e251; Rosas 10 et al., PLoS Med (2008); 5:e93; Selman M et al., Am J Respir Crit Care Med (2006); 173:188-198; Selman M et al. PLoS One 2007; 2:e482; Kaminski N et al., Proc Natl Acad Sci USA (2000); 97:1778-1783; Zuo F et al. Proc Natl Acad Sci USA (2002); 99:6292-6297; Yang I V et al., Am J Respir Crit Care Med (2007); 175:45-54.), as well as down-regulation of caveolin-1 (Wang X M et al., J Exp Med (2006); 203:2895-2906) and advanced glycosylation end products-specific receptor (AGER) (Englert J M et al., Am J Pathol (2008); 172:583-591), in IPF. All these genes behaved similarly in stable IPF and IPF-AEx, as did the majority of all other genes that distinguished IPF from control samples. No dramatic shift in gene expression that would indicate a new process or a dramatic shift in lung cellular phenotype or content was detected. Although increases in some genes associated with response to stress (HMOX1 and HSP1A1) were found, no changes in known inflammation-related genes, such as IL-1, IL-6, tumor necrosis factor-a, or NF-kB target genes in the comparison of IPF and IPF-AEx were found. Interestingly, other genes increased in acute lung injury such as AGER, a known marker of generalized inflammation (Uchida T et al., Am J Respir Crit Care Med (2006); 173:1008-1015), were not increased in IPF-AEx lungs. In fact, AGER was significantly decreased in IPFA-Ex compared with control samples, potentially reflecting loss of type I alveolar epithelial cells (Rosas I O et al., *PLoS Med* (2008); 5:e93; Englert J M et al., *Am J Pathol* (2008); 172:583-591). Taken together, these results do not support an overwhelming lung inflammatory response as a potential mechanism for acute exacerbation. It has not been found any gene expression patterns indicative of a response of the lung to viral or bacterial infections, a mechanism observed in animals (McMillan T R et al., *Am J Respir Crit Care Med* (2008); 177:771-780) but not yet confirmed in human IPF-AEx (Tomioka H et al., *Respirology* (2007); 12:700-706; Saydain G et al., *Am J Respir Crit Care Med* (2002); 166:839-842). Although these results do not rule out an occult viral infection or a previous viral infection as the triggering mechanism for IPF-AEx, neither do they support a role for an active infection during the last phase of the syndrome.

Naturally, the analysis is limited by the dependence on tissue harvested at explant or warm autopsy. It is entirely possible that by the time the patients experienced the final deterioration all evidence of response to an infection or infected tissue was destroyed. In this context the finding of increased α-defensin levels and the evidence of epithelial injury may be interpreted as remnants of an infectious process that triggered the acute lung injury but was cleared by the time the lungs were harvested. Although this interpretation cannot be disapproved, the lack of expression of viral response genes is not likely to reduce the likelihood of an active infection. A definite answer regarding the role of infections will require sampling earlier at presentation and longitudinal studies of the same patient, a task impossible with lung tissue but attainable with bronchial lavage or peripheral blood samples.

One of the remarkable features of the study is the localization of increased CCNA2 expression to the alveolar epithelium, rather than to fibroblasts or myofibroblastic foci. CCNA2 is the main A-type cyclin present in somatic cells (Gong D et al., *Curr Biol* (2007); 17:85-91) and a mediator of the cell cycle. The over-expression and localization of CCNA2 to epithelial cells but not to mesenchymal cells suggests that IPF-AEx is probably an extension of the epithelial injury and dysregulation that characterizes IPF (Selman M et al., *Proc Am Thorac Soc* (2006); 3:364-372) and definitely is not a result of uncontrolled fibroblast proliferation. The fact that the majority of CCNA2-expressing cells were also positive for Ki-67, a proliferation marker, suggests that CCNA2 expression represents a proliferative response of the epithelium. In light of the positive TUNEL staining in the epithelium and hyaline membranes, it is tempting to hypothesize that this enhanced proliferation represents a failed compensatory response to injury, localizing the pathogenesis of IPF-AEx to the epithelium.

One use of lung gene expression data is in the identification of differentially expressed genes that encode secreted proteins. Such secreted proteins may be detected in the alveolar fluid or peripheral blood and thus be useful as potential surrogate markers for disease activity (Rosas I O et al., *PLoS Med* (2008); 5:e93). Previous studies suggested that peripheral blood IL-8, KL-6, and most recently circulating fibrocytes may be increased in IPF-AEx (Moeller A et al., *Am J Respir Crit Care Med* (2009); 179:588-594; Tajima S et al., *Chest* (2003); 124:1206-1214; Ziegenhagen M W et al., *Am J Respir Crit Care Med* (1998); 157:762-768.). In this study, the genes encoding α-defensins were significantly increased in IPF-AEx lungs compared with stable IPF or control samples, and their protein expression was increased in the plasma of patients with IPF-AEx. α-Defensins are innate immunity antimicrobial peptides abundant in neutrophil granules and mucosal surfaces (Boman H G, *Annu Rev Immunol* (1995); 13:61-92; Zasloff M, *Nature* (2002); 415:389-395). α-Defensins affect various immune functions. α-Defensins are involved in activation of the classical complement pathway (van den Berg R H et al., *Blood* (1998); 92:3898-3903; Prohaszka Z et al., *Mol Immunol* (1997); 34:809-816). In vitro α-defensins induce the production of heat shock proteins and type I collagens in human lung fibroblasts (Yoshioka S et al., *Life Sci* (2007); 80:1839-1845), and stimulate cytokine production of bronchial epithelial cells (Sakamoto N et al., *Am J Physiol* (2005); 288:L508-L513). Elevation of α-defensins has been described in pulmonary alveolar proteinosis (Mukae H et al., *Respir Med* 2007; 101:715-721), α1-antitrypsin deficiency (Spencer L T et al., Am J Physiol (2004); 286: L514-L520), acute respiratory distress (Ashitani J et al., *Life Sci* (2004); 75:1123-1134), and chronic lung allograft rejection (Nelsestuen G L et al., *Proteomics* (2005); 5:1705-1713) and in patients with IPF but not in the context of acute exacerbation (Mukae H et al., Thorax (2002); 57: 623-628). In this context, it is important to note that it was observed α-defensin expression in surfactant protein C-expressing cells in IPF-AEx lungs—a finding that suggests that the plasma increases in α-defensins may be indicative of the lung microenvironment in IPF-AEx and again highlights the central role of the epithelium in IPF-AEx.

In summary, gene expression patterns indicate that IPF-AEx represents an extension of the molecular process that underlies IPF and not a new process. Although expression patterns that distinguish stable IPF and IPF-AEx lungs from normal lung are similar, genes that are differentially expressed in a direct comparison of IPF and IPF-AEx lungs were identified. The increased expression of CCNA2 and α-defensins is localized to the epithelium of IPF-AEx lungs, where widespread proliferation and apoptosis are detected, suggesting that the central molecular events in IPF-AEx are localized to the alveolar epithelium. Taken together, these results indicate the central role of alveolar epithelial injury in IPF-AEx and thus support the study of agents that protect the epithelium as therapeutic measures in this devastating syndrome. The identification of increases in plasma concentrations of proteins originating from the pulmonary epithelium in patients with IPF-AEx suggests their use as tools for evaluating patients with IPF during the course of the disease.

6.5 Example 5

149 patients with IPF were enrolled, including one American Indian, one African American, 45 females and 105 males. The average age of these 149 patients upon enrollment was 67.0 (+/−8.3). Gender, age, ethnic origin and status for all groups are presented in Table 11. Of these patients 107 patients with IPF with an FVC measurement within 90 days of blood draw were enrolled in the FVC analysis, including one American Indian, one African American, 36 females and 71 males. The average age of these 107 patients upon enrollment was 66.9 (+/−8.0). So far 41 of these 107 patients have died including 4 having had a lung transplant Gender, age, ethnic origin and status for all groups are presented in Table 12.

TABLE 11

| | All 149 patients with IPF | |
|---|---|---|
| Sex | Male | 104 (69.8%) |
| | Female | 45 (30.2%) |
| Race | Caucasian | 146 (98.0%) |
| | African-American | 1 (0.67%) |

TABLE 11-continued

All 149 patients with IPF

|  |  |  |  |
|---|---|---|---|
|  | American Indian |  | 1 (0.67%) |
|  | Unknown |  | 1 (0.67%) |
| Age at | Total |  | 67.0 ± 8.3 |
| blood draw | Male |  | 68.9 ± 8.5 |
| (Mean ± SD) | Female |  | 66.3 ± 8.1 |
| Status | Alive and untransplanted |  | 62 (41.6%) |
|  | Alive and transplanted |  | 19 (12.8%) |
|  | Died without transplant |  | 58 (38.9%) |
|  | Died after transplant |  | 10 (6.7%) |
| baseline FVC within 90 days of blood draw |  | 115 (77.2%) | 62.0 ± 19.6 |
| baseline DLCO within 90 days of blood draw |  | 103 (69.1%) | 45.4 ± 17.0 |

TABLE 12

107 patients in the FVC analysis

|  |  |  |  |
|---|---|---|---|
| Sex | Male |  | 71 (66.4%) |
|  | Female |  | 36 (33.6%) |
| Race | Caucasian |  | 105 (98.1%) |
|  | African-American |  | 1 (0.9%) |
|  | American Indian |  | 1 (0.9%) |
|  | Unknown |  | 0 (0.0%) |
| Age at | Total |  | 66.9 ± 8.0 |
| blood draw | Male |  | 67.5 ± 8.4 |
| (Mean ± SD) | Female |  | 65.9 ± 8.0 |
| Status | Alive and untransplanted |  | 51 (47.7%) |
|  | Alive and transplanted |  | 15 (14.0%) |
|  | Died without transplant |  | 37 (36.6%) |
|  | Died after transplant |  | 4 (3.7%) |
| baseline FVC within 90 days of blood draw |  | 87 (81.3%) | 66.1 ± 18.6 |
| baseline DLCO within 90 days of blood draw |  | 82 (76.6%) | 45.4 ± 17.0 |

Among the 149 patients as described in Table 11, 68 patients died including 10 patents who had a lung transplant and 58 patients who did not receive lung transplant. Nineteen patients are alive after a lung transplant, and 62 patients are alive without a lung transplant. The median interval from blood draw until death or lung transplant was 2.1 years with 95% C.I. 1.6 to 2.9 years (FIG. 24).

Figure 25:
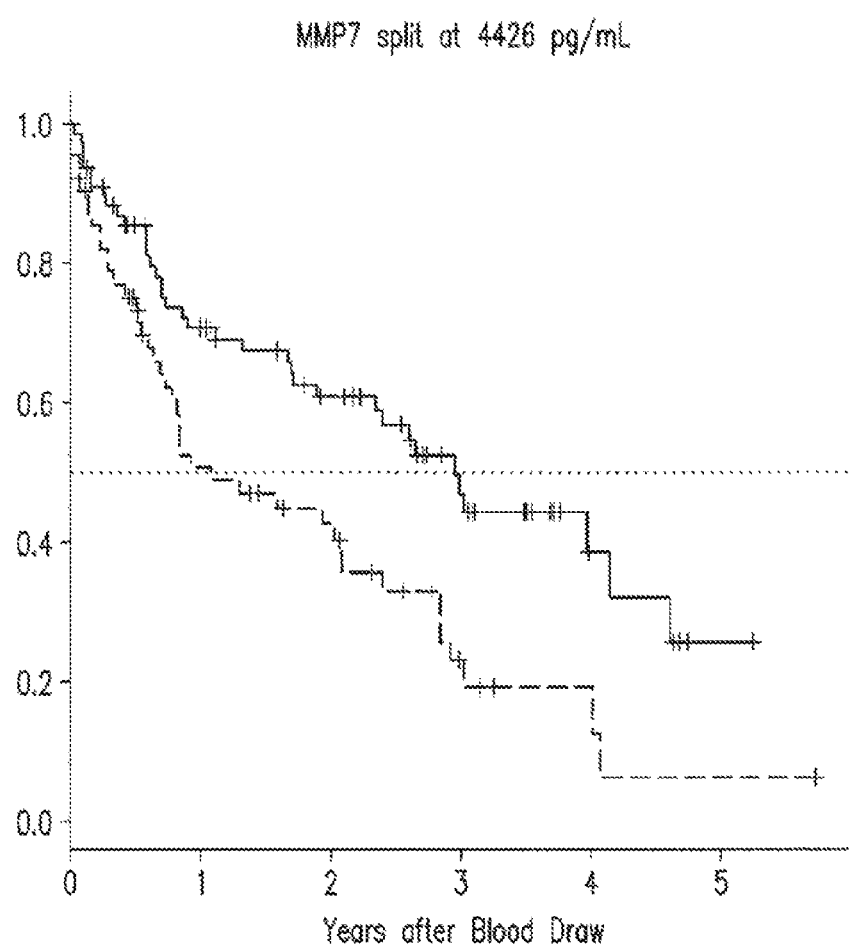

MMP7 and S100A12 are Independent Predictors for Progression of IPF:

MMP7, MMP3, Cancer_Antigen_125 (CA125), 5100A12, SPD, and TIMP1 were studied. The results have shown that the median interval from blood draw to lung transplant or death for patients whose plasma concentrations of MMP7 were at least 4426 pg/mL, was 1.1 years, and the median interval to lung transplant or death for patients whose plasma concentrations of MMP7 were less than 4426 pg/mL, was 3.0 years. The p value for comparing the interval to lung transplant or death with respect to plasma concentrations of MMP7 was 0.003 (FIG. 25). The median interval from blood draw to lung transplant or death, for patients whose plasma concentrations of MMP3 were at least 7.3 ng/mL, was 1.6 years, and the median interval to lung transplant or death for patients whose plasma concentrations of MMP3 were less than 7.3 ng/mL, was 2.6 years. The p value for comparing the interval to lung transplant or death with respect to plasma concentrations of MMP3 was 0.05 (FIG. 26). The median interval from blood draw to lung transplant or death for patients whose plasma concentrations of CA125 were at least 11.0 U/mL, was 1.7 years, and the median interval to lung transplant or death for patients whose plasma concentrations of CA125 were less than 11.0 U/mL, was 3.0 years. The p value for comparing the interval to lung transplant or death with respect to plasma concentrations of CA125 was 0.048 (FIG. 27). The median interval from blood draw to lung transplant or death for patients whose plasma concentrations of S100A12 were at least 24.0 ng/mL, was 0.9 years, and the median interval to lung transplant or death for patients whose plasma concentrations of S100A12 were less than 24.0 ng/mL, was 3.0 years. The p value for comparing the interval to lung transplant or death with respect to plasma concentrations of S100A12 was 0.005 (FIG. 28). The median interval from blood draw to lung transplant or death for patients whose plasma concentrations of SPD were at least 337.0 ng/mL, was 1.3 years, and the median interval to lung transplant or death for patients whose plasma concentrations of SPD were less than 337.0 ng/mL, was 2.7 years. The p value for comparing the interval to lung transplant or death with respect to plasma concentrations of SPD was 0.03 (FIG. 29). The median interval from blood draw to lung transplant or death for patients whose plasma concentrations of TIMP1 were at least 64.0 ng/mL was 1.9 years, and the median interval to lung transplant or death for patients whose plasma concentrations of TIMP1 were less than 64.0 ng/mL was 3.0 years. The p value for comparing the interval to lung transplant or death with respect to plasma concentrations of TIMP1 was 0.037 (FIG. 30).

The observed differences in years of lung transplant free survival for patients with respect to plasma concentrations of MMP7, CA125, S100A12, SPD, or TIMP1, were all statistically significant at p value<0.05, Furthermore, the observed differences in years of lung transplant free survival with respect to plasma concentrations of MMP7 or S100A12 were statistically significant at p value<0.01. Therefore, MMP7 and S100A12 are independent predictors for the progression of IPF. High plasma concentration of MMP7 indicates high risk of death in IPF and indicates progression of IPF. High plasma concentration of S100A12 indicates high risk of death in IPF and indicates progression of IPF.

6.6 Example 6

As illustrated in Example 5, 149 patients with IPF were enrolled, including one American Indian, one African American, 45 females and 105 males. The average age of these 149 patients upon enrollment was 67.0 (+/−8.3). Gender, age, ethnic origin and status for all groups are presented in Table 11. Of these patients 107 patients with IPF with an FVC measurement within 90 days of blood draw were enrolled in the FVC analysis, including one American Indian, one African American, 36 females and 71 males. The average age of these 107 patients upon enrollment was 66.9 (+/−8.0). So far 41 of these 107 patients have died including 4 having had a lung transplant Gender, age, ethnic origin and status for all groups are presented in Table 12.

MMP1 and MMP7 are Predictors for Progression of IPF. The median disease progression free interval, from blood draw to 10% or greater decline in FVC % predicted within one year, for patients whose plasma concentrations of MMP7 and MMP1 were at least 4.3 ng/mL and 0.54 ng/mL, respectively, was 0.98 years, and the median interval from blood draw to 10% or greater decline in FVC % predicted within one year for patients whose plasma concentrations of MMP7 and MMP1 did not both exceed 4.3 ng/mL and 0.54 ng/mL, respectively, was 2.0 years. The p value for comparison of progression-free survival with respect to plasma concentrations of MMP7 and MMP1 was 0.016 (FIG. 31). The median disease progression free interval for patients whose plasma concentrations of MMP7 were at least 4155 pg/mL, was 0.9 years, and the median interval from blood draw to 10% or greater decline in FVC % predicted within one year for patients whose plasma concentrations of MMP7 were less than 4155 pg/mL, was 2.1 years. The p value for comparison of progression-free survival with respect to plasma concentrations of MMP7 was 0.006 (FIG. 33). Thus, high plasma concentration of MMP7 indicates increased risk for IPF disease progression, as determined by decline in pulmonary function measured by FVC % predicted, and simultaneously high plasma concentration of MMP1 increases this risk of IPF disease progression even more.

6.7 Example 7

MMP7 is a Predictor for Progression of IPF:

IL12p40, MMP7, IL4, Tissue Factor, and TNFRII were studied. The median interval from blood draw to 10% or greater decline in FVC % predicted within one year for patients whose plasma concentrations of IL12p40 were at least 0.15 ng/mL, was 0.3 years, and the median interval from blood draw to 10% or greater decline in FVC % predicted within one year for patients whose plasma concentrations of IL12p40 were less than 0.15 ng/mL, was 1.3 years. The p value for comparison of progression-free survival with respect to plasma concentrations of IL12p40 was 0.0003 (FIG. 32). The median interval from blood draw to 10% or greater decline in FVC % predicted within one year, for patients whose plasma concentrations of MMP7 were at least 4155 pg/mL, was 0.9 years, and the median interval from blood draw to 10% or greater decline in FVC % predicted within one year, for patients whose plasma concentrations of MMP7 were less than 4155 pg/mL, was 2.1 years. The p value for comparison of progression-free survival with respect to plasma concentrations of MMP7 was 0.006 (FIG. 33). The median interval from blood draw to 10% or greater decline in FVC % predicted within one year, for patients whose plasma concentrations of IL4 were at least 11 pg/mL, was 0.9 years, and the median interval from blood draw to 10% or greater decline in FVC % predicted within one year, for patients whose plasma concentrations of IL4 was less than 11 pg/mL was 1.7 years. The p value for comparison of progression-free survival with respect to plasma concentrations of IL4 was 0.04 (FIG. 34). The median interval from blood draw to 10% or greater decline in FVC % predicted within one year, for patients whose plasma concentrations of Tissue Factor were at least 0.2 ng/mL, was 1.3 years, and the median interval from blood draw to 10% or greater decline in FVC % predicted within one year, for patients whose plasma concentrations of Tissue Factor was less than 0.2 ng/mL was 1.3 years. The p value for comparison of progression-free survival with respect to plasma concentrations of Tissue Factor was 0.69 (FIG. 35). The median interval from blood draw to 10% or greater decline in FVC % predicted within one year, for patients whose plasma concentrations of TNFRII were at least 5 ng/mL, was 0.94 years, and the median interval from blood draw to 10% or greater decline in FVC % predicted within one year, for patients whose plasma concentrations of TNFRII was less than 5 ng/mL was 1.33 years. The p value for comparison of progression-free survival with respect to plasma concentrations of TNFRII was 0.13 (FIG. 36).

The results have shown that MMP is an independent predictor of progression of IPF. High plasma concentration of MMP1 indicates progression of IPF, as determined by decline in pulmonary function measured by FVC % predicted.

Various publications are cited herein, the contents of which are hereby incorporated by reference in their entireties.

What is claimed is:

1. A method of identifying progression of idiopathic pulmonary fibrosis in a subject, comprising: measuring the serum or plasma levels of MMP7, DEFA-1, DEFA-2, DEFA-3, S100A12, and IL12P40 mRNA by use of a kit comprising a means for determining the serum or plasma levels of MMP7, DEFA-1 DEFA-2, DEFA-3, S100A12, and IL12P40 mRNA, wherein said kit does not contain means for determining the serum or plasma levels of more than twenty other markers, and wherein an increase in the level of MMP7 mRNA, an increase in the level of DEFA-1 mRNA, an increase in the level of DEFA-2 mRNA, an increase in the level of DEFA-3 mRNA, an increase in the level of S100A12 mRNA, and an increase in the level of IL12P40 mRNA indicate progression of idiopathic pulmonary fibrosis.

2. A method of evaluating whether a lung transplant is recommended or should be performed comprising: identifying the progression of idiopathic pulmonary fibrosis in a subject, comprising measuring the serum or plasma levels of MMP7, DEFA-1, DEFA-2, DEFA-3, S100A12, and IL12P40 mRNA by use of a kit comprising a means for determining the serum or plasma levels of MMP7, DEFA-1 DEFA-2, DEFA-3, S100A12, and IL12P40 mRNA, wherein said kit does not contain means for determining the serum or plasma levels of more than twenty other markers, and wherein if an increase in the level of MMP7 mRNA, an increase in the level of DEFA-1 mRNA, an increase in the level of DEFA-2 mRNA, an increase in the level of DEFA-3 mRNA, an increase in the level of S100A12 mRNA, and an increase in the level of IL12P40 mRNA, has been determined, a lung transplant is recommended or performed.

3. A kit for evaluating the progression of idiopathic pulmonary fibrosis in a subject, comprising a means for determining the serum or plasma levels of MMP7, DEFA-1 DEFA-2, DEFA-3, S100A12, and IL12P40, wherein said kit does not contain means for determining the serum or plasma levels of more than twenty other markers.

4. The method of claim 1, wherein the serum or plasma levels of MMP7, DEFA-1, DEFA-2, DEFA-3, S100A12, and IL12P40 mRNA are measured via a nucleic acid hybridization assay.

5. The method of claim 4, wherein the nucleic acid hybridization assay is a microarray hybridization assay.

6. The method of claim 1, wherein the serum or plasma levels of MMP7, DEFA-1, DEFA-2, DEFA-3, S100A12, and IL12P40 mRNA are measured via a nucleic acid amplification assay.

7. The method of claim 6, wherein the nucleic acid amplification assay is a quantitative reverse transcriptase-polymerase chain reaction assay.

8. A method of identifying progression of idiopathic pulmonary fibrosis in a subject, comprising measuring the serum or plasma levels of MMP7, DEFA-1, DEFA-2, DEFA-3, S100A12, and IL12P40 protein by use of a kit comprising a means for determining the serum or plasma levels of MMP7, DEFA-1 DEFA-2, DEFA-3, S100A12, and IL12P40 protein, wherein said kit does not contain means for determining the serum or plasma levels of more than twenty other markers, and wherein an increase in the level of MMP7 protein, an increase in the level of DEFA-1 protein, an increase in the level of DEFA-2 protein, an increase in the level of DEFA-3 protein, an increase in the level of S100A12 protein, and an increase in the level of IL12P40 protein indicate progression of idiopathic pulmonary fibrosis.

9. A method of evaluating whether a lung transplant is recommended or should be performed comprising: identifying the progression of idiopathic pulmonary fibrosis in a subject, comprising measuring the serum or plasma levels of MMP7, DEFA-1, DEFA-2, DEFA-3, S100A12, and IL12P40 protein by use of a kit comprising a means for determining the serum or plasma levels of MMP7, DEFA-1 DEFA-2, DEFA-3, S100A12, and IL12P40 protein, wherein said kit does not contain means for determining the serum or plasma levels of more than twenty other markers, and wherein if an increase in the level of MMP7 protein, an increase in the level of DEFA-1 protein, an increase in the level of DEFA-2 protein, an increase in the level of DEFA-3 protein, an increase in the level of S100A12 protein, and an increase in the level of IL12P40 protein, has been determined, a lung transplant is recommended or performed.

10. The method of claim 8, wherein the means for determining the serum or plasma levels of MMP7, DEFA-1, DEFA-2, DEFA-3, S100A12, and IL12P40 protein comprises an immunoassay.

11. The method of claim 10, wherein the immunoassay is an enzyme-linked immunosorbent assay.

12. The kit of claim 3, further comprising, for each molecule to be tested, a capture agent selected from the group consisting of: an antibody; a portion of an antibody; a single chain antibody; a non-immunoglobulin receptor for the molecule; a peptide ligand for the molecule; and an oligonucleotide ligand for the molecule.

13. The kit of claim 12, wherein the capture agent is bound to a solid support.

14. The kit of claim 13, wherein the solid support is a bead.

15. The kit of claim 3, further comprising a means for determining the level of at least one control serum or plasma marker.

16. The kit of claim 3, further comprising a reagent for determining a marker level, wherein the reagent comprises a labeled secondary antibody; an enzyme; avidin; or streptavidin.

* * * * *